(12) United States Patent
Lo et al.

(10) Patent No.: US 12,247,259 B2
(45) Date of Patent: *Mar. 11, 2025

(54) USING NUCLEIC ACID SIZE RANGE FOR NONINVASIVE CANCER DETECTION

(71) Applicants: The Chinese University of Hong Kong, Shatin (HK); GRAIL, Inc., Menlo Park, CA (US)

(72) Inventors: Yuk-Ming Dennis Lo, Homantin (CN); Rossa Wai Kwun Chiu, Shatin (CN); Kwan Chee Chan, Mei Foo Sun Chuen (CN); Peiyong Jiang, Pak Shek Kok (CN)

(73) Assignees: The Chinese University of Hong Kong, New Territories (HK); GRAIL, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/521,333

(22) Filed: Nov. 8, 2021

(65) Prior Publication Data

US 2022/0064714 A1 Mar. 3, 2022

Related U.S. Application Data

(62) Division of application No. 16/178,378, filed on Nov. 1, 2018, now Pat. No. 11,168,356.

(60) Provisional application No. 62/580,906, filed on Nov. 2, 2017.

(51) Int. Cl.
C12Q 1/6886 (2018.01)
C12Q 1/6809 (2018.01)
C12Q 1/6883 (2018.01)

(52) U.S. Cl.
CPC ......... *C12Q 1/6886* (2013.01); *C12Q 1/6883* (2013.01); *C12Q 1/6809* (2013.01); *C12Q 2600/154* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 8,620,593 B2 | 12/2013 | Lo et al. | |
| 8,706,422 B2 | 4/2014 | Lo et al. | |
| 9,732,390 B2 | 8/2017 | Lo et al. | |
| 11,116,835 B2 * | 9/2021 | McGuire | C12N 15/1133 |
| 2012/0208711 A1 * | 8/2012 | Cortese | C12Q 1/6837 506/2 |
| 2013/0237431 A1 | 9/2013 | Lo et al. | |
| 2014/0080715 A1 | 3/2014 | Lo et al. | |
| 2015/0011403 A1 | 1/2015 | Lo et al. | |
| 2015/0087529 A1 | 3/2015 | Lo et al. | |
| 2016/0017419 A1 | 1/2016 | Chiu et al. | |
| 2017/0220736 A1 | 8/2017 | Lo et al. | |
| 2020/0335215 A1 * | 10/2020 | Rabizadeh | G16H 70/60 |

FOREIGN PATENT DOCUMENTS

| | | | |
|---|---|---|---|
| CN | 105243295 | | 1/2016 |
| CN | 106795562 A | | 5/2017 |
| CN | 106886688 | | 6/2017 |
| WO | 2009013496 | | 1/2009 |
| WO | 2009051842 | | 4/2009 |
| WO | 2014043763 | | 3/2014 |
| WO | 2016008451 | | 1/2016 |
| WO | 2016112850 | | 7/2016 |
| WO | 2016116033 | | 7/2016 |
| WO | WO-2019-085988 | * | 5/2019 |

OTHER PUBLICATIONS

Bartak et al Gastroenterology. May 2014. 146.5, Suppl. 1: S324 (Year: 2014).*
Grunt et al Transl Cancer res. 2018. 7(Suppl 2): S171-S184 (Year: 2018).*
English translation of Office Action mailed Aug. 2, 2022 in JP Patent Application No. 2020-544091. 6 pages.
Jiang, Peiyong et al.; "The Long and Short of Circulating Cell-Free DNA and the Ins and Outs of Molecular Diagnostics"; Trends in Genetics; Jun. 2016; vol. 32, No. 6; pp. 360-371.
Yu, Stephanie C. et al.; "Combined Count- and Size-Based Analysis of Maternal Plasma DNA for Noninvasive Prenatal Detection of Fetal Subchromosomal Aberrations Facilitates Elucidation of the Fetal and/or Maternal Origin of the Aberrations"; Clinical Chemistry; 2017; vol. 63, No. 2; pp. 495-502.
European Application No. EP18874285.2 , Extended European Search Report mailed on Jul. 14, 2021, 10 pages.
Chan et al., Size Distributions of Maternal and Fetal DNA in Maternal Plasma, Clinical Chemistry, vol. 50, No. 1, Jan. 2004, pp. 88-92.
Chiu et al., Noninvasive Prenatal Diagnosis of Fetal Chromosomal Aneuploidy by Massively Parallel Genomic Sequencing of DNA in Maternal Plasma, Proceedings of the National Academy of Sciences, vol. 105, No. 51, Dec. 23, 2008, pp. 20458-20463.

(Continued)

*Primary Examiner* — Carla J Myers
(74) *Attorney, Agent, or Firm* — Kilpatrick Townsend & Stockton LLP

(57) ABSTRACT

Size-band analysis is used to determine whether a chromosomal region exhibits a copy number aberration or an epigenetic alteration. Multiple size ranges may be analyzed instead of focusing on specific sizes. By using multiple size ranges instead of specific sizes, methods may analyze more sequence reads and may be able to determine whether a chromosomal region exhibits a copy number aberration even when clinically-relevant DNA may be a low fraction of the biological sample. Using multiple ranges may allow for the use of all sequence reads from a genomic region, rather than a selected subset of reads in the genomic region. The accuracy of analysis may be increased with higher sensitivity at similar or higher specificity. Analysis may include fewer sequencing reads to achieve the same accuracy, resulting in a more efficient process.

23 Claims, 30 Drawing Sheets

(56) References Cited

OTHER PUBLICATIONS

Fan et al., Analysis of the Size Distributions of Fetal and Maternal Cell-Free DNA by Paired-End Sequencing, Clinical Chemistry, vol. 56, No. 8, Aug. 2010, pp. 1279-1286.
Fan et al., Non-Invasive Prenatal Measurement of the Fetal Genome, Nature, vol. 487, Jul. 19, 2012, pp. 320-326.
Flusberg et al., Direct Detection of DNA Methylation During Single-Molecule, Real-Time Sequencing, Nature Methods, vol. 7, No. 6, Jun. 2010, pp. 461-465.
Jiang et al., Lengthening and Shortening of Plasma DNA in Hepatocellular Carcinoma Patients, Proceedings of the National Academy of Sciences, vol. 112, No. 11, Feb. 2, 2015, pp. E1317-E1325.
Lo et al., Maternal Plasma DNA Sequencing Reveals the Genome-Wide Genetic and Mutational Profile of the Fetus, Science Translational Medicine, vol. 2, No. 61, Dec. 2010, pp. 1-13.
Lo et al., Plasma Nucleic Acid Analysis by Massively Parallel Sequencing: Pathological Insights and Diagnostic Implications, Journal of Pathology, vol. 225, No. 3, Aug. 24, 2011, pp. 318-323.
Lun et al., Noninvasive Prenatal Methylomic Analysis by Genomewide Bisulfite Sequencing of Maternal Plasma DNA, Clinical Chemistry, vol. 59, No. 11, Nov. 2013, pp. 1583-1594.
International Application No. PCT/CN2018/113640, International Search Report and Written Opinion mailed on Feb. 1, 2019, 13 pages.
Schreiber et al., Error Rates for Nanopore Discrimination among Cytosine, Methylcytosine, and Hydroxymethylcytosine along Individual DNA Strands, Proceedings of the National Academy of Sciences, vol. 110, No. 47, Nov. 19, 2013, pp. 18910-18915.
Soto et al., The Impact of Next-Generation Sequencing on the DNA Methylation-Based Translational Cancer Research, Translational Research, vol. 169, Mar. 2016, pp. 1-18.
Vaca-Paniagua et al., Targeted Deep DNA Methylation Analysis of Circulating Cell-Free DNA in Plasma using Massively Parallel Semiconductor Sequencing, Epigenomics, Volume 7, Issue 3, 2015, pp. 353-362.
Yu et al., Size-Based Molecular Diagnostics Using Plasma DNA for Noninvasive Prenatal Testing, Proceedings of the National Academy of Sciences, vol. 111, No. 23, Jun. 10, 2014, pp. 8583-8588.
English translation of Office Action and Search Report mailed Feb. 10, 2023 in TW Patent Application No. 107139084. 6 pages.
English translation of Office Action mailed Apr. 4, 2023 in JP Patent Application No. 2020-544091. 3 pages.
Office Action dated Mar. 6, 2024 in IL Patent Application No. 274097. 4 pages.
Examination Report No. 1 dated Apr. 26, 2024 in AU Patent Application No. 2018359944. 5 pages.
English translation of Office Action mailed Nov. 26, 2024 in JP Patent Application No. 2023-127899. 7 pages.
English translation of Office Action dated Dec. 24, 2024 in KR Patent Application No. 10-2020-7014693. 7 pages.

\* cited by examiner

USING NUCLEIC ACID SIZE RANGE FOR NONINVASIVE CANCER DETECTION

CROSS-REFERENCES TO RELATED APPLICATIONS

The present application is a continuation application of U.S. patent application Ser. No. 16/178,378, entitled "USING NUCLEIC ACID SIZE RANGE FOR NONINVASIVE CANCER DETECTION," filed Nov. 1, 2018, which claims priority from and is a non-provisional application of U.S. Provisional Application No. 62/580,906, entitled "USING NUCLEIC ACID SIZE RANGE FOR NONINVASIVE PRENATAL TESTING AND CANCER DETECTION," filed Nov. 2, 2017, the entire contents of each of which are herein incorporated by reference for all purposes.

BACKGROUND

The demonstration of the presence of circulating cell-free DNA (cfDNA) originating from the fetus in the blood plasma and serum of pregnant women (Lo et al., Lancet 1997; 350:485-487) has completely transformed the practice of prenatal testing through the development of noninvasive prenatal testing (NIPT). NIPT has an advantage in avoiding risks associated with invasive tissue sampling, such as via amniocentesis and chorionic villus sampling (CVS). Thus far, NIPT has been used for fetal RhD blood group genotyping (Finning et al. *BMJ* 2008; 336:816-818; Lo et al. *N Engl J Med* 1998; 339:1734-1738), fetal sex determination for sex-linked disorders (Costa et al. *N. Engl. J. Med.* 2002; 346:1502), chromosomal aneuploidy detection (Chiu et al. *Proc Natl Acad Sci USA* 2008; 105:20458-20463; Fan et al. *Nature* 2012; 487:320-324; Chiu et al. *BMJ* 2011; 342: c7401; Bianchi et al. *N.* Engl. J. Med. 2014; 370:799-808; Yu et al. *Proc. Natl. Acad. Sci. U.S.A.* 2014; 111:8583-8; Norton et al. *N. Engl. J Med.* 2015; 372:1589-1597) and diagnosis of monogenic disorders (Lam et al. *Clin. Chem.* 2012; 58:1467-75; Lo et al. *Sci. Transl. Med.* 2010; 2:61ra91-61ra91; Ma et al. *Gene* 2014; 544:252-258; New et al. *J. Clin. Endocrinol. Metab.* 2014; 99:E1022-E1030). In particular, using massively parallel sequencing of maternal plasma DNA, NIPT for common chromosomal aneuploidies has been rapidly adopted for clinical service in dozens of countries and is used by millions of pregnant women every year (Allyse et al. *Int. J Womens. Health* 2015; 7:113-26; Chandrasekharan et al. *Sci Transl Med* 2014; 6:231fs15).

In early validation studies (Chiu et al. *BMJ* 2011; 342: c7401; Sparks et al. *Am. J. Obstet. Gynecol.* 2012; 206: 319.e1-9), NIPTs were performed on patients at high-risk for aneuploidy, and high positive predictive values (PPVs) have been achieved from 92% to 100%. The relative concentration of fetal DNA in a particular maternal sample, commonly referred to as the fetal DNA fraction, is an important determinant of the accuracy of NIPT (Chiu et al. *BMJ* 2011; 342:c7401; Jiang et al. *Bioinformatics* 2012; 28:2883-2890, *npj Genomic Med.* 2016; 1:16013). The sensitivity of trisomy 21 detection would be significantly decreased with a reduction in the fetal DNA fraction (Chiu et al. *BMJ* 2011; 342:c7401; Canick et al. *Prenat. Diagn.* 2013; 33:667-674). Hence, false negative results for trisomy detection might occur in pregnancies with low fetal DNA fractions. For example, Canick et al reported that among 212 cases with Down syndrome, there were 4 false negatives, all of which had fetal DNA fractions were between 4% and 7% (Canick et al. *Prenat. Diagn.* 2013; 33:667-674).

It is important to note that for in a number of laboratories performing NIPTs, test failures or no-call results would be observed in a proportion of analyses. In some studies, the total laboratory failure rate could be as high as 8.8% (Porreco et al. *Am. J Obstet. Gynecol.* 2014; 211:365.e1-365.e12). One of main reasons for the failure to obtain a result on NIPT is the low fetal DNA fraction in maternal plasma DNA in some samples, usually <4% (Gil et al. *Fetal Diagn. Ther.* 2014; 35:156-73). It was demonstrated that in patients with a fetal DNA fraction below 4%, the prevalence of aneuploidy was reported to be 4.7%, which was significantly higher compared with the prevalence of 0.4% in the overall cohort (Norton et al. *N. Engl. J. Med.* 2015; 372: 1589-1597). Therefore, such test failures can ultimately adversely affect the overall performance of NIPT. For example, it was illustrated that the higher test failure rate would lead to lower actual PPVs (Yaron *Prenat. Diagn.* 2016; 36:391-6). In a theoretical estimation (Yaron *Prenat. Diagn.* 2016; 36:391-6), a failure rate of 0.1% in a laboratory would give an actual PPV of 67%, however a failure rate of 1% would give rise to an actual PPV of 16.7% assuming that all these patients with test failures that were reported to be associated with an increased risk of aneuploidy will undergo invasive testing to ascertain if the fetuses are indeed aneuploid according to recommendations from the American Congress of Obstetricians and Gynecologists (ACOG) recommendation (Yaron *Prenat. Diagn.* 2016; 36:391-6).

It has been shown that approximately 2% of pregnancies have a fetal DNA fraction lower than 4% (Wang et al. *Prenat. Diagn.* 2013; 33:662-666). It is unlikely that the blood redraw for the patients with a first blood sample showing a low fetal DNA fraction would warrant an sufficient fetal DNA fraction because the increase of fetal DNA between 10 and 21 weeks is very subtle (with approximately a 0.1% average weekly increase in fetal DNA fraction) (Wang et al. *Prenat. Diagn.* 2013; 33:662-666). In addition, such low fetal DNA fractions preferentially occur in women with high maternal weights. In some studies, the failure to report a result due to fetal DNA fraction less than 4% could be as high as 5.9% (Hall et al. *PLoS One* 2014; 9:e96677).

Therefore, it would be useful to develop an approach for improving the performance of NIPT for pregnant women with low fetal DNA fractions in maternal plasma (e.g., below 4%), Such improvements would be valuable for the performance of NIPT for common chromosomal aneuploidies (e.g. trisomy 21, trisomy 18, trisomy 13, and sex chromosome aneuploidies) as well as for sub-chromosomal aberrations (e.g. microdeletions and microduplications). In addition, improving accuracy and efficiency of testing for copy number aberrations and cancer can be addressed with similar approaches. These and other needs are addressed below.

SUMMARY

Size-band analysis is used to determine whether a chromosomal region exhibits a copy number aberration or is used to detect cancer. Multiple size ranges may be analyzed instead of focusing on specific sizes. By using multiple size ranges instead of specific sizes, methods may be able to determine whether a chromosomal region exhibits a copy number aberration even when clinically-relevant DNA may be a low fraction of the biological sample. Using multiple ranges may allow for the use of all sequence reads from a genomic region, rather than a selected subset of reads in the genomic region. The accuracy of analysis may be increased with higher sensitivity at similar or higher specificity. Analysis may include fewer sequencing reads to achieve the same accuracy, resulting in a more efficient process. Because analysis may be done with a lower fraction of clinically-relevant DNA, analysis may be done at an earlier stage of pregnancy or cancer.

A better understanding of the nature and advantages of embodiments of the present invention may be gained with reference to the following detailed description and the accompanying drawings.

TERMS

Figure 1:
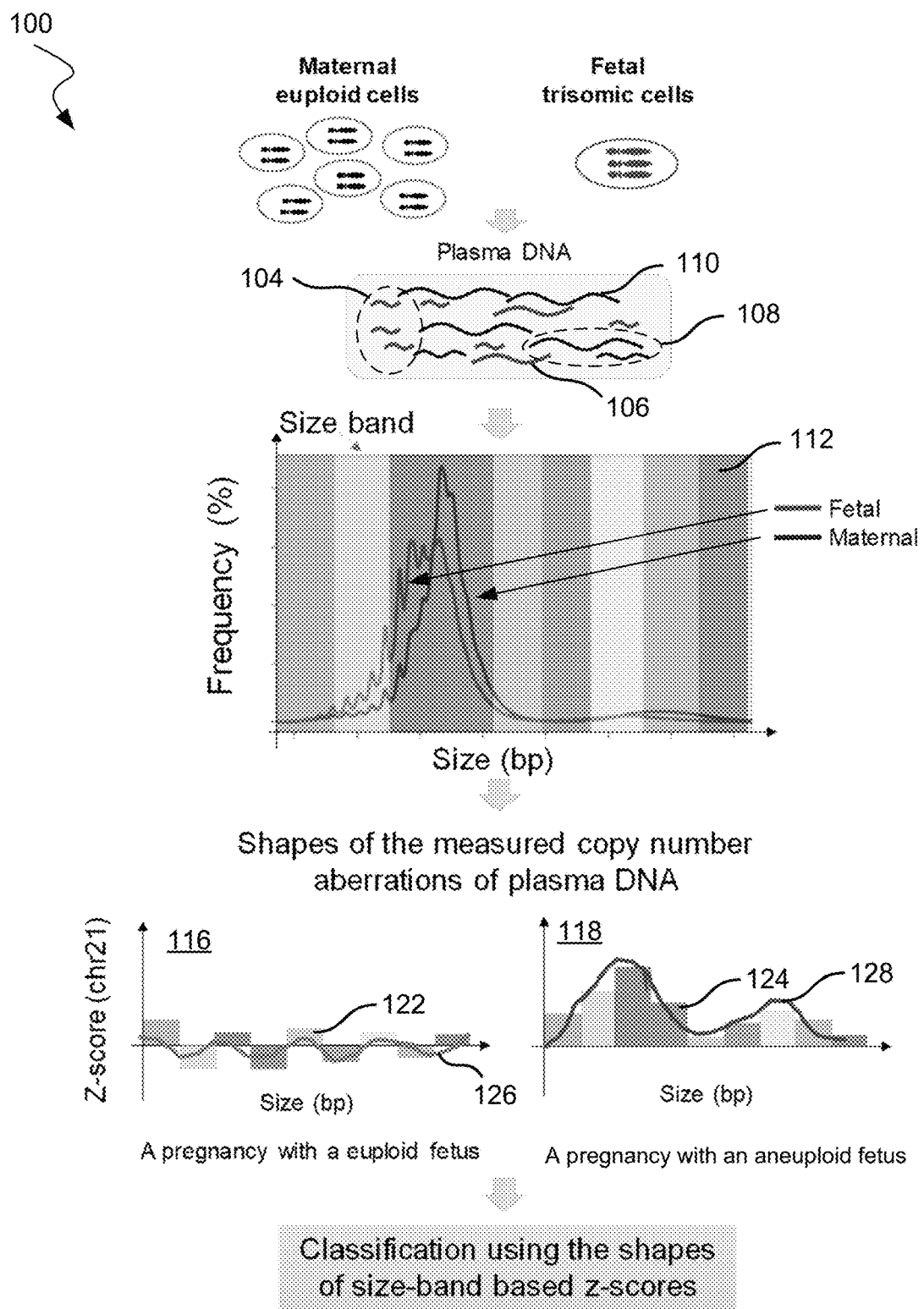
FIG. 1 shows a schematic illustration of the principle of plasma DNA size-band analysis according to embodiments of the present invention.

The term "sample", "biological sample" or "patient sample" is meant to include any tissue or material derived from a living or dead subject. A biological sample may be a cell-free sample, which may include a mixture of nucleic acid molecules from the subject and potentially nucleic acid molecules from a pathogen, e.g., a virus. A biological sample generally comprises a nucleic acid (e.g., DNA or RNA) or a fragment thereof. The term "nucleic acid" may generally refer to deoxyribonucleic acid (DNA), ribonucleic acid (RNA) or any hybrid or fragment thereof. The nucleic acid in the sample may be a cell-free nucleic acid. A sample may be a liquid sample or a solid sample (e.g., a cell or tissue sample). The biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. Stool samples can also be used. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). The centrifugation protocol can include, for example, 3,000 g×10 minutes, obtaining the fluid part, and re-centrifuging at, for example, 30,000 g for another 10 minutes to remove residual cells.

As used herein, the term "locus" or its plural form "loci" is a location or address of any length of nucleotides (or base pairs) which has a variation across genomes. The term "sequence read" refers to a sequence obtained from all or part of a nucleic acid molecule, e.g., a DNA fragment. In one embodiment, just one end of the fragment is sequenced. Alternatively, both ends (e.g., about 30 bp from each end) of the fragment can be sequenced to generate two sequence reads. The paired sequence reads can then be aligned to a reference genome, which can provide a length of the fragment. In yet another embodiment, a linear DNA fragment can be circularized, e.g., by ligation, and the part spanning the ligation site can be sequenced.

The term "fragment" (e.g., a DNA fragment), as used herein, can refer to a portion of a polynucleotide or polypeptide sequence that comprises at least 3 consecutive nucleotides. A nucleic acid fragment can retain the biological activity and/or some characteristics of the parent polypeptide. A nucleic acid fragment can be double-stranded or single-stranded, methylated or unmethylated, intact or nicked, complexed or not complexed with other macromolecules, e.g. lipid particles, proteins. A tumor-derived nucleic acid can refer to any nucleic acid released from a tumor cell, including pathogen nucleic acids from pathogens in a tumor cell.

The term "assay" generally refers to a technique for determining a property of a nucleic acid. An assay (e.g., a first assay or a second assay) generally refers to a technique for determining the quantity of nucleic acids in a sample, genomic identity of nucleic acids in a sample, the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay known to a person having ordinary skill in the art may be used to detect any of the properties of nucleic acids mentioned herein. Properties of nucleic acids include a sequence, quantity, genomic identity, copy number, a methylation state at one or more nucleotide positions, a size of the nucleic acid, a mutation in the nucleic acid at one or more nucleotide positions, and the pattern of fragmentation of a nucleic acid (e.g., the nucleotide position(s) at which a nucleic acid fragments). The term "assay" may be used interchangeably with the term "method". An assay or method can have a particular sensitivity and/or specificity, and their relative usefulness as a diagnostic tool can be measured using ROC-AUC statistics.

The term "random sequencing," as used herein, generally refers to sequencing whereby the nucleic acid fragments sequenced have not been specifically identified or predetermined before the sequencing procedure. Sequence-specific primers to target specific gene loci are not required. In some embodiments, adapters are added to the end of a fragment, and the primers for sequencing attached to the adapters. Thus, any fragment can be sequenced with the same primer that attaches to a same universal adapter, and thus the sequencing can be random. Massively parallel sequencing may be performed using random sequencing.

"Nucleic acid" may refer to deoxyribonucleotides or ribonucleotides and polymers thereof in either single- or double-stranded form. The term may encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs may include, without limitation, phosphorothioates, phosphoramidites, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The term "nucleotide," in addition to referring to the naturally occurring ribonucleotide or deoxyribonucleotide monomers, may be understood to refer to related structural variants thereof, including derivatives and analogs, that are functionally equivalent with respect to the particular context in which the nucleotide is being used (e.g., hybridization to a complementary base), unless the context clearly indicates otherwise.

A "sequence read" refers to a string of nucleotides sequenced from any part or all of a nucleic acid molecule. For example, a sequence read may be the entire nucleic acid fragment that exists in the biological sample. Also as an example, a sequence read may be a short string of nucleotides (e.g., 20-150 bases) sequenced from a nucleic acid fragment, a short string of nucleotides at one or both ends of a nucleic acid fragment, or the sequencing of the entire nucleic acid fragment that exists in the biological sample. A sequence read may be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification, or based on biophysical measurements, such as mass spectrometry. A sequence read may be obtained from a single-molecule sequencing. "Single-molecule sequencing" refers to sequencing of a single template DNA molecule to obtain a sequence read without the need to interpret base sequence information from clonal copies of a template DNA molecule. The single-molecule sequencing may sequence the entire molecule or only part of the DNA molecule. A majority of the DNA molecule may be sequenced, e.g., greater than 50%, 55%, 60%, 65%, 70%, 75%, 80%, 85%, 90%, 95%, or 99%.

The term "universal sequencing" refers to sequencing where adapters are added to the end of a fragment, and the primers for sequencing attached to the adapters. Thus, any fragment can be sequenced with the same primer, and thus the sequencing can be random.

Examples of "clinically-relevant" DNA include fetal DNA in maternal plasma and tumor DNA in the patient's plasma. Another example include the measurement of the amount of graft-associated DNA in the plasma of a transplant patient. A further example include the measurement of the relative amounts of hematopoietic and nonhematopoietic DNA in the plasma of a subject. This latter embodiment can be used for detecting or monitoring or prognosticating pathological processes or injuries involving hematopoietic and/or nonhematopoietic tissues.

The term "level of cancer" (or more generally "level of disease" or "level of condition") can refer to whether cancer exists (i.e., presence or absence), a stage of a cancer, a size of tumor, whether there is metastasis, the total tumor burden of the body, the cancer's response to treatment, and/or other measure of a severity of a cancer (e.g. recurrence of cancer). The level of cancer may be a number (e.g., a probability) or other indicia, such as symbols, alphabet letters, and colors. The level may be zero. The level of cancer may also include premalignant or precancerous conditions (states). The level of cancer can be used in various ways. For example, screening can check if cancer is present in someone who is not known previously to have cancer. Assessment can investigate someone who has been diagnosed with cancer to monitor the progress of cancer over time, study the effectiveness of therapies or to determine the prognosis. In one embodiment, the prognosis can be expressed as the chance of a patient dying of cancer, or the chance of the cancer progressing after a specific duration or time, or the chance of cancer metastasizing. Detection can mean 'screening' or can mean checking if someone, with suggestive features of cancer (e.g. symptoms or other positive tests), has cancer. A "level of pathology" can refer to level of pathology associated with a pathogen, where the level can be as described above for cancer. The level of diseases/condition can also be as described above for cancer. When the cancer is associated with a pathogen, a level of cancer can be a type of a level of pathology.

The term "chromosome aneuploidy" as used herein means a variation in the quantitative amount of a chromosome from that of a diploid genome. The variation may be a gain or a loss. It may involve the whole of one chromosome or a region of a chromosome.

The term "sequence imbalance" or "aberration" as used herein means any significant deviation as defined by at least one cutoff value in a quantity of the clinically relevant chromosomal region from a reference quantity. A sequence imbalance can include chromosome dosage imbalance, allelic imbalance, mutation dosage imbalance, copy number imbalance, haplotype dosage imbalance, and other similar imbalances. As an example, an allelic imbalance can occur when a tumor has one allele of a gene deleted or one allele of a gene amplified or differential amplification of the two alleles in its genome, thereby creating an imbalance at a particular locus in the sample. As another example, a patient could have an inherited mutation in a tumor suppressor gene. The patient could then go on to develop a tumor in which the non-mutated allele of the tumor suppressor gene is deleted. Thus, within the tumor, there is mutation dosage imbalance. When the tumor releases its DNA into the plasma of the patient, the tumor DNA will be mixed in with the constitutional DNA (from normal cells) of the patient in the plasma. Through the use of methods described herein, mutational dosage imbalance of this DNA mixture in the plasma can be detected. An aberration can include a deletion or amplification of a chromosomal region.

"DNA methylation" in mammalian genomes typically refers to the addition of a methyl group to the 5' carbon of cytosine residues (i.e. 5-methylcytosines) among CpG dinucleotides. DNA methylation may occur in cytosines in other contexts, for example CHG and CHH, where H is adenine, cytosine or thymine. Cytosine methylation may also be in the form of 5-hydroxymethylcytosine. Non-cytosine methylation, such as N6-methyladenine, has also been reported.

A "classification" refers to any number(s) or other characters(s) that are associated with a particular property of a sample. For example, a "+" symbol (or the word "positive") could signify that a sample is classified as having deletions or amplifications. The classification can be binary (e.g., positive or negative) or have more levels of classification (e.g., a scale from 1 to 10 or 0 to 1).

The term "cutoff" and "threshold" can refer to a predetermined number used in an operation. A threshold or reference value may be a value above or below which a particular classification applies, e.g., a classification of a condition, such as whether a subject has a condition or a severity of the condition. A cutoff may be predetermined with or without reference to the characteristics of the sample or the subject. For example, cutoffs may be chosen based on the age or sex of the tested subject. A cutoff may be chosen after and based on output of the test data. For example, certain cutoffs may be used when the sequencing of a sample reaches a certain depth. As another example, reference subjects with known classifications of one or more conditions and measured characteristic values (e.g., a methylation level, a statistical size value, or a count) can be used to determine reference levels to discriminate between the different conditions and/or classifications of a condition (e.g., whether the subject has the condition). Any of these terms can be used in any of these contexts. As will be appreciated by one of skilled in the art, a cutoff can be selected to achieve a desired sensitivity and specificity.

A "site" (also called a "genomic site") corresponds to a single site, which may be a single base position or a group of correlated base positions, e.g., a CpG site or larger group of correlated base positions. A "locus" may correspond to a region that includes multiple sites. A locus can include just one site, which would make the locus equivalent to a site in that context.

The "methylation index" for each genomic site (e.g., a CpG site) can refer to the proportion of DNA fragments (e.g., as determined from sequence reads or probes) showing methylation at the site over the total number of reads covering that site. A "read" can correspond to information (e.g., methylation status at a site) obtained from a DNA fragment. A read can be obtained using reagents (e.g. primers or probes) that preferentially hybridize to DNA fragments of a particular methylation status. Typically, such reagents are applied after treatment with a process that differentially modifies or differentially recognizes DNA molecules depending of their methylation status, e.g. bisulfite conversion, or methylation-sensitive restriction enzyme, or methylation binding proteins, or anti-methylcytosine antibodies. In another embodiment, single molecule sequencing techniques that recognize methylcytosines and hydroxymethylcytosines can be used for elucidating the methylation status and for determining a methylation index.

The "methylation density" of a region can refer to the number of reads at sites within the region showing methylation divided by the total number of reads covering the sites in the region. The sites may have specific characteristics, e.g., being CpG sites. Thus, the "CpG methylation density" of a region can refer to the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of cytosines not converted after bisulfite treatment (which corresponds to methylated cytosine) at CpG sites as a proportion of all CpG sites covered by sequence reads mapped to the 100-kb region. This analysis can also be performed for other bin sizes, e.g. 500 bp, 5 kb, 10 kb, 50-kb or 1-Mb, etc. A region could be the entire genome or a chromosome or part of a chromosome (e.g. a chromosomal arm). The methylation index of a CpG site is the same as the methylation density for a region when the region only includes that CpG site. The "proportion of methylated cytosines" can refer to the number of cytosine sites, "C's", that are shown to be methylated (for example unconverted after bisulfite conversion) over the total number of analyzed cytosine residues, i.e. including cytosines outside of the CpG context, in the region. The methylation index, methylation density, and proportion of methylated cytosines are examples of "methylation levels," which may include other ratios involving counts of methylated reads at sites. Apart from bisulfite conversion, other processes known to those skilled in the art can be used to interrogate the methylation status of DNA molecules, including, but not limited to enzymes sensitive to the methylation status (e.g. methylation-sensitive restriction enzymes), methylation binding proteins, single molecule sequencing using a platform sensitive to the methylation status (e.g. nanopore sequencing (Schreiber et al. Proc Natl Acad Sci 2013; 110: 18910-18915) and by the Pacific Biosciences single molecule real time analysis (Flusberg et al. Nat Methods 2010; 7: 461-465)).

"Methylation-aware sequencing" refers to any sequencing method that allows one to ascertain the methylation status of a DNA molecule during a sequencing process, including, but not limited to bisulfite sequencing, or sequencing preceded by methylation-sensitive restriction enzyme digestion, immunoprecipitation using anti-methylcytosine antibody or methylation binding protein, or single molecule sequencing that allows elucidation of the methylation status. A "methylation-aware assay" or "methylation-sensitive assay" can include both sequencing and non-sequencing based methods, such as MSP, probe based interrogation, hybridization, restriction enzyme digestion followed by density measurements, anti-methylcytosine immunoassays, mass spectrometry interrogation of proportion of methylated cytosines or hydroxymethylcytosines, immunoprecipitation not followed by sequencing, etc.

A "separation value" (or relative abundance) corresponds to a difference or a ratio involving two values, e.g., two amounts of DNA molecules, two fractional contributions, or two methylation levels, such as a sample (mixture) methylation level and a reference methylation level. The separation value could be a simple difference or ratio. As examples, a direct ratio of x/y is a separation value, as well as x/(x+y). The separation value can include other factors, e.g., multiplicative factors. As other examples, a difference or ratio of functions of the values can be used, e.g., a difference or ratio of the natural logarithms (ln) of the two values. A separation value can include a difference and/or a ratio. A methylation level is an example of a relative abundance, e.g., between methylated DNA molecules (e.g., at particular sites) and other DNA molecules (e.g., all other DNA molecules at particular sites or just unmethylated DNA molecules). The amount of other DNA molecules can act as a normalization factor. As another example, an intensity of methylated DNA molecules (e.g., fluorescent or electrical intensity) relative to intensity of all or unmethylated DNA molecules can be determined. The relative abundance can also include an intensity per volume.

The terms "control", "control sample", "reference", "reference sample", "normal", and "normal sample" may be interchangeably used to generally describe a sample that does not have a particular condition, or is otherwise healthy. In an example, a method as disclosed herein may be performed on a subject having a tumor, where the reference sample is a sample taken from a healthy tissue of the subject. In another example, the reference sample is a sample taken from a subject with the disease, e.g. cancer or a particular stage of cancer. A reference sample may be obtained from the subject, or from a database. The reference generally refers to a reference genome that is used to map sequence reads obtained from sequencing a sample from the subject. A reference genome generally refers to a haploid or diploid genome to which sequence reads from the biological sample and the constitutional sample can be aligned and compared. For a haploid genome, there is only one nucleotide at each locus. For a diploid genome, heterozygous loci can be identified, with such a locus having two alleles, where either allele can allow a match for alignment to the locus. A reference genome may correspond to a virus, e.g., by including one or more viral genomes.

The phrase "healthy," as used herein, generally refers to a subject possessing good health. Such a subject demonstrates an absence of any malignant or non-malignant disease. A "healthy individual" may have other diseases or conditions, unrelated to the condition being assayed, that may normally not be considered "healthy".

The terms "cancer" or "tumor" may be used interchangeably and generally refer to an abnormal mass of tissue wherein the growth of the mass surpasses and is not coordinated with the growth of normal tissue. A cancer or tumor may be defined as "benign" or "malignant" depending on the following characteristics: degree of cellular differentiation including morphology and functionality, rate of growth, local invasion, and metastasis. A "benign" tumor is generally well differentiated, has characteristically slower growth than a malignant tumor, and remains localized to the site of origin. In addition, a benign tumor does not have the capacity to infiltrate, invade, or metastasize to distant sites. A "malignant" tumor is generally poorly differentiated (anaplasia), has characteristically rapid growth accompanied by progressive infiltration, invasion, and destruction of the surrounding tissue. Furthermore, a malignant tumor has the capacity to metastasize to distant sites. "Stage" can be used to describe how advance a malignant tumor is. Early stage cancer or malignancy is associated with less tumor burden in the body, generally with less symptoms, with better prognosis, and with better treatment outcome than a late stage malignancy. Late or advanced stage cancer or malignancy is often associated with distant metastases and/or lymphatic spread.

The term "false positive" (FP) can refer to subjects not having a condition. False positive generally refers to subjects not having a tumor, a cancer, a pre-cancerous condition (e.g., a precancerous lesion), a localized or a metastasized cancer, a non-malignant disease, or are otherwise healthy. The term false positive generally refers to subjects not having a condition, but are identified as having the condition by an assay or method of the present disclosure.

The terms "sensitivity" or "true positive rate" (TPR) can refer to the number of true positives divided by the sum of the number of true positives and false negatives. Sensitivity may characterize the ability of an assay or method to correctly identify a proportion of the population that truly has a condition. For example, sensitivity may characterize the ability of a method to correctly identify the number of subjects within a population having cancer. In another example, sensitivity may characterize the ability of a method to correctly identify one or more markers indicative of cancer.

The terms "specificity" or "true negative rate" (TNR) can refer to the number of true negatives divided by the sum of the number of true negatives and false positives. Specificity may characterize the ability of an assay or method to correctly identify a proportion of the population that truly does not have a condition. For example, specificity may characterize the ability of a method to correctly identify the number of subjects within a population not having cancer. In another example, specificity may characterize the ability of a method to correctly identify one or more markers indicative of cancer.

The term "ROC" or "ROC curve" can refer to the receiver operator characteristic curve. The ROC curve can be a graphical representation of the performance of a binary classifier system. For any given method, an ROC curve may be generated by plotting the sensitivity against the specificity at various threshold settings. The sensitivity and specificity of a method for detecting the presence of a tumor in a subject may be determined at various concentrations of tumor-derived nucleic acid in the plasma sample of the subject. Furthermore, provided at least one of the three parameters (e.g., sensitivity, specificity, and the threshold setting), and ROC curve may determine the value or expected value for any unknown parameter. The unknown parameter may be determined using a curve fitted to the ROC curve. The term "AUC" or "ROC-AUC" generally refers to the area under a receiver operator characteristic curve. This metric can provide a measure of diagnostic utility of a method, taking into account both the sensitivity and specificity of the method. Generally, ROC-AUC ranges from 0.5 to 1.0, where a value closer to 0.5 indicates the method has limited diagnostic utility (e.g., lower sensitivity and/or specificity) and a value closer to 1.0 indicates the method has greater diagnostic utility (e.g., higher sensitivity and/or specificity). See, e.g., Pepe et al, "Limitations of the Odds Ratio in Gauging the Performance of a Diagnostic, Prognostic, or Screening Marker," Am. J. Epidemiol 2004, 159 (9): 882-890, which is entirely incorporated herein by reference. Additional approaches for characterizing diagnostic utility using likelihood functions, odds ratios, information theory, predictive values, calibration (including goodness-of-fit), and reclassification measurements are summarized according to Cook, "Use and Misuse of the Receiver Operating Characteristic Curve in Risk Prediction," Circulation 2007, 115: 928-935, which is entirely incorporated herein by reference.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term "about" or "approximately" can mean within an order of magnitude, within 5-fold, and more preferably within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to ±10%. The term "about" can refer to ±5%.

The terminology used herein is for the purpose of describing particular cases only and is not intended to be limiting. As used herein, the singular forms "a", "an" and "the" are intended to include the plural forms as well, unless the context clearly indicates otherwise. The use of "or" is intended to mean an "inclusive or," and not an "exclusive or" unless specifically indicated to the contrary. The term "based on" is intended to mean "based at least in part on." Furthermore, to the extent that the terms "including", "includes", "having", "has", "with", or variants thereof are used in either the detailed description and/or the claims, such terms are intended to be inclusive in a manner similar to the term "comprising."

DETAILED DESCRIPTION

Size-based analysis of cell-free DNA has been used in analyzing biological samples for chromosomal aneuploidies and cancer. However, with previous size-based techniques, when the biological sample has a low percentage of clinically-relevant DNA, obtaining a statistically significant result may be difficult. When the fraction of clinically-relevant DNA is low, previous size-based analysis may be used to confirm the results of another type of analysis rather than relied upon as a single analysis technique. Embodiments of the present invention involve using size bands, which may allow for more cell-free DNA to be used in analysis and may allow for patterns of sizes to be analyzed. As a result, size-based analysis may be performed accurately at even low fractions of clinically-relevant DNA.

In this study, we aimed to apply size analysis of cell-free DNA to lower the limit of fetal DNA fraction required for NIPT. We aim to improve the sensitivity of NIPT, without adversely impacting the specificity. Similar techniques may be applied to cancer analysis. Using multiple size ranges instead of specific sizes was found to allow for analysis of biological samples even when the fraction of clinically-relevant DNA is low. Embodiments may include using size bands to determine whether a chromosomal region exhibits a copy number aberration (CNA). The CNA may be related to an aneuploidy or cancer. Embodiments may also include using size bands to determine a level of cancer.

I. Size-Based Analysis

It has been demonstrated that the fetal-derived molecules in maternal plasma are shorter than the maternal DNA molecules (Chan et al. *Clin Chem* 2004; 50:88-92; Lo et al. *Sci. Transl. Med* 2010; 2:61ra91-61ra91). Researchers have made use of such a size difference to enrich for fetal DNA in maternal plasma samples for NIPT (Li et al. *Clin Chem* 2004; 50:1002-1011, JAMA 2005; 293:843-9; Lun et al. *Proc. Natl. Acad Sci. U.S.A.* 2008; 105:19920-5). Yu et al. had illustrated that fetal chromosomal aneuploidies could be detected by determining an aberrant proportion of short fragments from an aneuploid chromosome in paired-end sequencing data (Yu et al. *Proc. Natl. Acad Sci. U.S.A.* 2014; 111:8583-8). Such an approach can achieve good NIPT performance when compared with the counting of DNA molecules in maternal plasma (Yu et al. *Proc. Natl. Acad Sci. U.S.A.* 2014; 111:8583-8).

To improve the accuracy of noninvasive detection of fetal chromosomal abnormalities in pregnant women with low fetal DNA fractions (e.g. <4%), one possible method that has been previously explored is the selective analysis of short DNA molecules through in silico size selection or physical size selection (e.g., WO 2009/013496, filed Jul. 23, 2008, which is incorporated herein by reference for all purposes). In these methods, data or molecules from the short plasma DNA molecules form the basis for statistical analyses, disease classification, and case interpretation. As fetal-derived DNA molecules have a shorter size distribution compared with maternal-derived ones, the selective analysis of short DNA fragments could preferentially enrich fetal-derived DNA molecules, resulting in higher fetal DNA fractions.

As fetal DNA fraction is a key factor governing the NIPT performance, this may potentially improve the accuracy of NIPT. However, it was reported that in-silico selection of sequenced reads with lengths <150 bp could increase the effective fetal DNA fraction but would not necessarily increase the sensitivity of aneuploidy detection by single-molecule counting because of a trade-off between the fetal DNA fraction and the number of molecules being counted (Fan et al. *Clin. Chem.* 2010; 56:1279-1286). In other words, as shown in Table 1, the previous approaches with selecting short DNA could not improve the sensitivity without increasing sequencing depth because of the marked reduction in number of plasma DNA fragments that are counted. Reducing the size of the plasma DNA fragments analyzed reduces the number of DNA fragments that are analyzed. For example, if only lengths less than 100 bp are analyzed, the DNA fragments undergo a 48.5 fold reduction. At the same time, by focusing on smaller plasma DNA fragments, the fetal DNA fraction is enriched. For example, for lengths less than 100 bp, the fetal DNA fraction has a 1.78 fold enrichment. However, the 1.78 fold enrichment is small compared to the 48.5 fold reduction in plasma DNA molecules being analyzed.

TABLE 1

| Plasma DNA size (bp) | The fold enrichment in fetal DNA fraction (x) | The fold reduction in plasma DNA molecules being analyzed (x) |
| --- | --- | --- |
| <150 | 1.93 | 4.67 |
| <120 | 2.04 | 21.2 |
| <110 | 1.91 | 32.3 |
| <100 | 1.78 | 48.5 |

On the other hand, we have previously developed another plasma DNA size-based approach (U.S. Pat. No. 8,620,593) to improve diagnostic specificity by taking advantage of DNA molecules below a certain threshold, for example 150 bp in size. In this method, average size of plasma DNA molecules derived from a potential aneuploidy chromosome are compared with the average size of plasma DNA molecules derived from other chromosomes. This approach has been shown to improve the specificity of non-invasive detection of chromosomal aneuploidies because fetal chromosomal aneuploidies would result in shortening of the average size of the plasma DNA molecules from an overrepresented chromosome (e.g. trisomic chromosome) or lengthening of the average size of plasma DNA molecules for an underrepresented chromosome (e.g. monosomic chromosome). However, such an approach could not be expected to enhance the sensitivity because of the reduction in number of plasma DNA molecules counted.

There were some previous efforts attempting to use the in silico selection of particular short DNA molecules to quantify the copy number changes of an aneuploid chromosome (Fan et al. *Clin. Chem.* 2010; 56:1279-1286). However, such a specific size selection would reduce the number of DNA molecules that would contribute to the final clinical classification, therefore increasing the stochastic variations. Analytically, such increase in stochastic variations may be manifested as increase in the coefficient of variation (CV) or standard deviation (SD). According to the Poisson distribution, for every 4-fold reduction in the number of molecules being analyzed, the CV would increase 2-fold. On the other hand, for every 2-fold increase in the fractional concentration of circulating fetal DNA, the number of molecules that one would need to count to arrive at a correct diagnosis of fetal chromosomal aneuploidy would decrease by 4-fold. If one would use the size selection for those molecules below 150 bp, the fetal DNA fraction would increase ~2-fold but the number of plasma DNA molecules would be decreased 4.7-fold. Therefore, the enrichment in fetal DNA fractions through a simple size selection would not be able to effectively offset the detrimental effect of the reduction of plasma DNA molecules, which might be an important reason why there was no consistent improvement in NIPT by a simple in silico size selection (Fan et al. *Clin. Chem.* 2010; 56:1279-1286).

II. Size Patterns

In this study, we developed a new way to incorporate the plasma DNA size information by making use of the detailed changing patterns of molecule counts across a series of different size ranges, which according to the empirical data has surprisingly resulted in an improvement in the test sensitivity. It is counter-intuitive because when fractionating plasma DNA molecules into more size bands, there should be far fewer sequenced DNA molecules per size band, and plasma DNA molecules within each band alone were not able to improve sensitivity. Instead of using one particular band alone, our new approach is to use the relationship across different bands to improve the performance.

We reasoned that the changes of genomic representation (GR) of an aneuploid chromosome would be varied in accordance with the measured fetal DNA fractions present in different sizes of plasma DNA molecules. We hypothesized that the relationship between the GR changes of an affected chromosome would be linked to different size ranges (size bands) in a non-random way because the cell-free fetal and maternal DNA sizes reflect two distinct fragmentation patterns (Lo et al. *Sci. Transl. Med.* 2010; 2:61ra91-61ra91). Therefore, we developed a new approach to analyze the detailed changing shapes of GR values originating from an aberrant chromosome among the different size bands. The schematic principle of this approach is illustrated in FIG. 1.

FIG. 1 shows a schematic illustration 100 of the principle of plasma DNA size-band analysis. Maternal plasma comprises a mixture of fetal DNA molecules (wavy red lines in section 104 and molecule 106) and maternal DNA molecules (wavy black lines in section 108 and molecule 110) originating from fetal and maternal cells, respectively. The fetal DNA molecules are generally shorter than the maternal ones as evidenced by the fetal DNA size profile shifting toward the left relative to that of maternal DNA molecules. Therefore, the measured fetal DNA fraction would be changed according to different size bands, generally enriching in the shorter size ranges. Thus, for a woman pregnant with a trisomic fetus, the measured genomic representations (GRs), whose deviation from reference group can be measured by z-score, would be expected to vary according to different size bands, but in contrast, no specific changes would occur in a pregnancy with a euploid fetus.

FIG. 1 shows the size bands both as discrete bands and as sliding windows. In the graph of frequency versus size, the different colored columns (e.g., column 112) show the size bands as corresponding to discrete size ranges. In graphs 116 and 118 of z-score (chr21) versus size, the colored columns (e.g., column 122 and column 124) show the z-scores for the different size bands. Lines 126 and 128 in graphs of z-score versus size show results for size bands as sliding windows. In the pregnancy with an aneuploid fetus, line 128 indicates the z-score for a size band centered on a particular size. For example, a data point with a given x-coordinate and y-coordinate on the line 128 has a z-score indicated by the y-coordinate for a range of sizes centered around the size indicated by the x-coordinate. Each z-score is a pooled z-score calculated for the entire size band. Hence, in graph 116 of the pregnancy with a euploid fetus, line 126 shows the results for size bands as sliding windows. In graph 118 of the pregnancy with an aneuploid fetus, line 128 shows the results for size bands as sliding windows.

Regardless of whether the size band is based on discrete or sliding windows, the shape or pattern of the z-scores of the size bands is distinctly different between a pregnancy with a euploid fetus and a pregnancy with an aneuploid fetus. For example, as shown in graph 116 and graph 118, the pregnancy with an aneuploid fetus shows a bimodal pattern compared to the more cyclical pattern in the pregnancy with the euploid fetus.

The patterns of counts across the different size bands can be related to fetal DNA fraction, tumor DNA fraction, or other clinically-relevant DNA fraction. Thus, this new approach that concurrently quantifies a series of molecule counts across different size bands and the relationship between different size-band based readouts would not lose plasma DNA molecules when integrating plasma DNA size properties compared to an approach that uses only specific sizes of DNA molecules. Such concurrent quantifications would improve accuracy compared with the use of just single readout below a certain size cutoff. The size-band patterns of copy number changes in plasma can be recognized with the use of, but not limited to, machine learning approaches such as an artificial neural network, k-nearest neighbors algorithm, support vector machine, and mixture Gaussian model, etc.

A. Verifying Size Pattern Data Analysis

The size pattern (i.e., the shape of a fraction or a parameter related to the amount of cell-free DNA at a particular size band) may depend on characteristics of the cell-free DNA. For example, the size pattern may depend on whether the biological sample includes cell-free DNA from an aneuploid fetus, as in graphs 116 and 118 in FIG. 1. First, the fetal DNA fraction for different sizes of DNA is analyzed to show that certain sizes of cell-free DNA are enriched for fetal DNA compared to maternal DNA. Second, data from a pregnant female with an aneuploid fetus is analyzed using size bands against data from pregnant females with euploid fetuses. These analyses confirm that size patterns can be analyzed to distinguish differences in CNAs, including when the CNAs are a result of an aneuploid fetus.

1. Measured Fetal DNA Fractions Vary According to Different Size Bands

To verify the hypothesis that the fetal DNA fraction changes would vary according to fragment sizes in a non-random manner, we reanalyzed the data described in our previous study (Chan et al. *Proc. Natl. Acad. Sci.* 2016; 113:E8159-E8168).

Figure 2B:
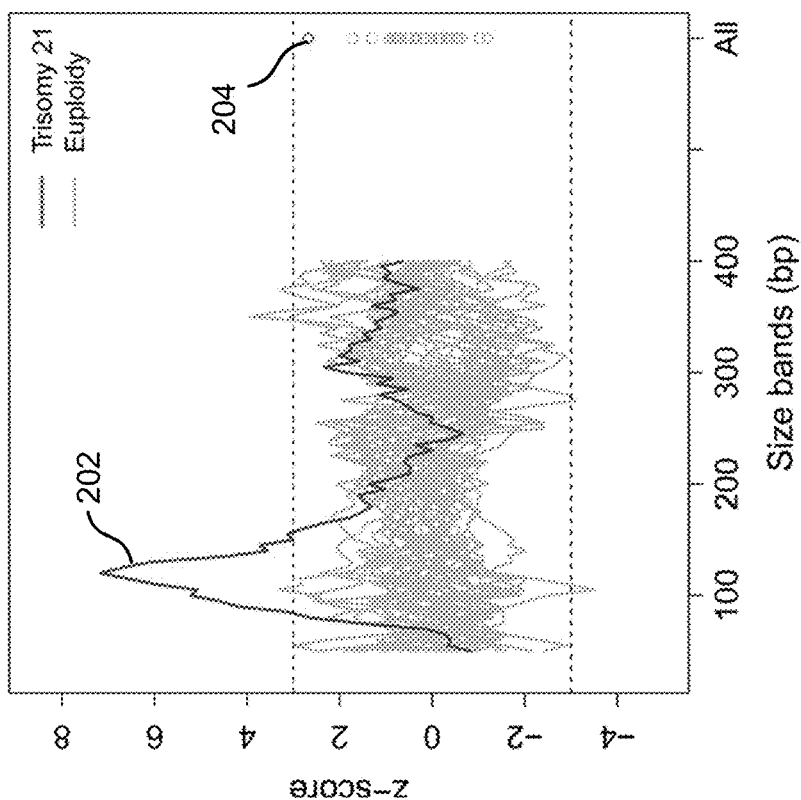
FIG. 2B shows the z-score for size bands for samples including DNA from euploidy and trisomy 21 fetuses according to embodiments of the present invention.
Figure 2A:
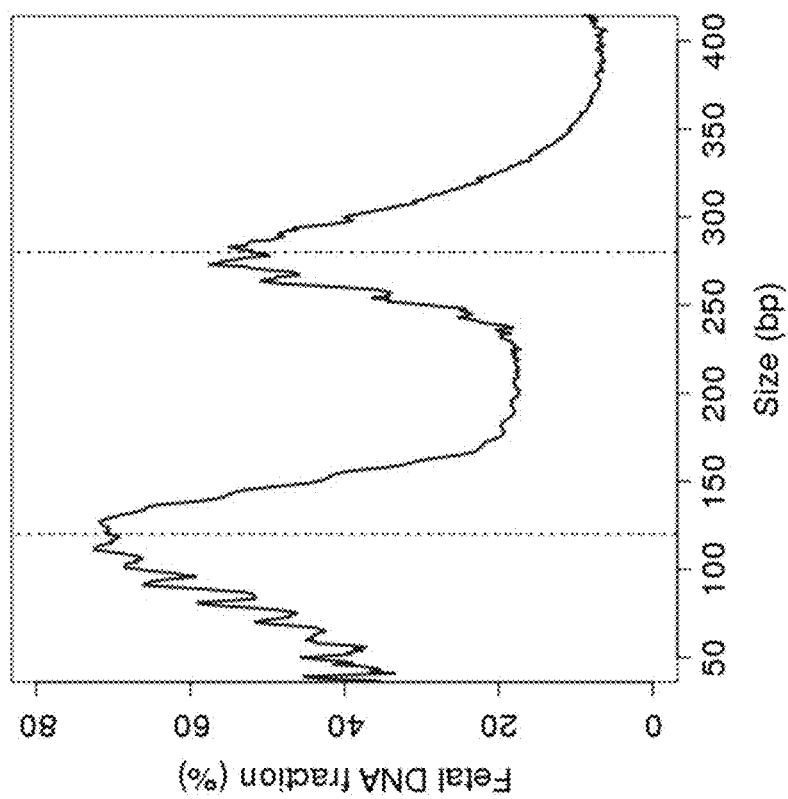
FIG. 2A shows the measured fetal DNA fraction for an aneuploid chromosome for sizes of plasma DNA fragment according to embodiments of the present invention.

FIG. 2A shows the measured fetal DNA fraction for an aneuploid chromosome for sizes of plasma DNA fragment, ranging from 50 to 400 bp. The x-axis is the size of a DNA molecule, and the y-axis is the fraction of DNA molecules at that size that are fetal DNA. For example, at a size of 120 bp, the fetal DNA fraction is 70.5%, which means that of the DNA molecules that have a size of 120 bp, 70.5% are from the fetus and 29.5% of them are from pregnant female. The fetal DNA fraction was determined from the chromosome Y percentage for a sample from a pregnant female with a male fetus. The fetal DNA fraction was found to be enriched at the sizes of 120 bp and 280 bp, respectively. A maximum of fetal DNA fraction of 70.5% was found at a size of 120 bp, which is 4× higher than the lowest one at 200 bp size with a fetal DNA fraction of 17.4%.

2. CNAs in Plasma DNA Vary for Different Size Bands

The changes in fetal DNA fractions exhibiting uneven patterns would impact the presentation of molecular counts originating from an aneuploid chromosome. An aneuploid chromosome has an abnormal number of chromosomes. An abnormal number of chromosomes in the fetus would affect the amount of fetal DNA compared to maternal DNA. For example, trisomy 21 has three chromosome 21s instead of only two. If the fetus has trisomy 21, then fetal DNA have a higher fraction than with a normal euploid fetus. As fetal DNA is often shorter than maternal DNA, a maternal sample of a female pregnant with a fetus with trisomy 21 would likely have a higher concentration of short DNA from chromosome 21 than compared to a maternal sample of a female pregnant with a euploid fetus.

FIG. 2B shows z-score results using size band sliding windows for a pregnancy with a trisomy 21 fetus and for pregnancies with euploid fetuses. The bandwidth of the size band sliding windows was 50 bp. The pregnancy with a trisomy 21 fetus had a fetal DNA fraction of 4%. As seen in FIG. 2B, the 120-bp position for the trisomy 21 fetus had the highest z-score out of all samples analyzed and therefore corresponded to the highest degree of measured copy number aberrations. Different size bands would affect magnitude of the z-score at 120 bp and other sizes. The calculation of the z-score of the affected chromosome is described below.

Assuming that the mid-point of a size band with a 50-bp bandwidth is located at length i (e.g. the mid-point of a size band located at an i of 75 bp and the band would range from 50 to 100 bp), then the percentage of sequencing reads mapping to the targeted chromosome (e.g. chromosome 21) can be calculated using such fragments within a particular size range of interest (e.g. from 50 to 100 bp), denoted as a genomic representation i (i.e. $GR_i$). The z-score for length i is calculated:

$$Z-\text{score}_i = \frac{GR_i - M_i}{SD_i}$$

where $M_i$ and $SD_i$ represent the mean and standard derivation of genomic representation of the targeted chromosome for the size band centered at length i, which was inferred in this study from 50 pregnancies carrying euploid fetuses. The full spectrum of sizes will be interrogated by dynamically changing the location of the mid-point of a size band in the size profile, ranging from 50 to 400 bp.

In FIG. 2B, we can observe regular wave-like patterns in the size-band based z-score curve 202 for a pregnancy with a trisomy 21 fetus. This observation was reminiscent of the changes of fetal DNA fractions in different size bands. However, there were no such patterns shown in the control group with euploid fetuses. The magnitude of such changes in a particular size band appeared to be different from the changes of the fetal DNA fractions. For example the z-score at 120 bp was much higher than that at 280 bp (FIG. 2B), but fetal DNA fractions were comparable between these two sizes (FIG. 2A). The variability may be a result of the molecular counts decreasing more rapidly at lengths longer than 166 bp compared with lengths shorter than 166 bp so that a high sampling variation would be present in long molecules.

FIG. 2B also shows the z-score for all sizes, illustrated as circles corresponding to the value labeled "All" on the x-axis. Red circle 204, which is the highest circle, corresponds to trisomy 21. Red circle 204 has a z-score below 3. Thus, if one would use all fragments and employ a z-score of 3 as a cutoff, this case would mistakenly be classified as a euploid fetus, resulting a false negative result. In contrast, if one would use the distinct shape of changes in z-scores varying against the different size bands, the case can be correctly identified as a trisomy 21 case in comparison with the control group.

B. Applying Size Pattern Analysis

Size pattern data were generated for females pregnant with either a euploid fetus or an aneuploid fetus. The data were then analyzed by different techniques, including using machine learning models, to determine if the size patterns could be used to distinguish between pregnancies with euploid fetuses and pregnancies with aneuploid fetuses.

1. Size-Band Shape of CNAs in Plasma Informs Chromosomal Aneuploidies with Low Fetal Fraction To evaluate whether such size-band based z-score patterns can be generalized to other samples with low fetal DNA fractions, we analyzed an additional 111 maternal plasma DNA samples each with a male fetus, including 48 cases each with a trisomy 21 fetus and 63 cases each with a euploid fetus. The fetal DNA fractions were estimated using Y chromosomal sequences derived from the male fetuses (Hudecova et al. *PLoS One* 2014; 9:e88484; Chiu et al. *BMJ* 2011; 342:c7401). To have enough cases with a low fetal DNA fraction of 4% or below, each paired-end sequencing dataset for 48 pregnancies with trisomic fetuses were mixed in silico with the sequencing dataset from cases with euploid fetuses to achieve the levels of 4% fetal DNA fraction or below.

Figure 3:
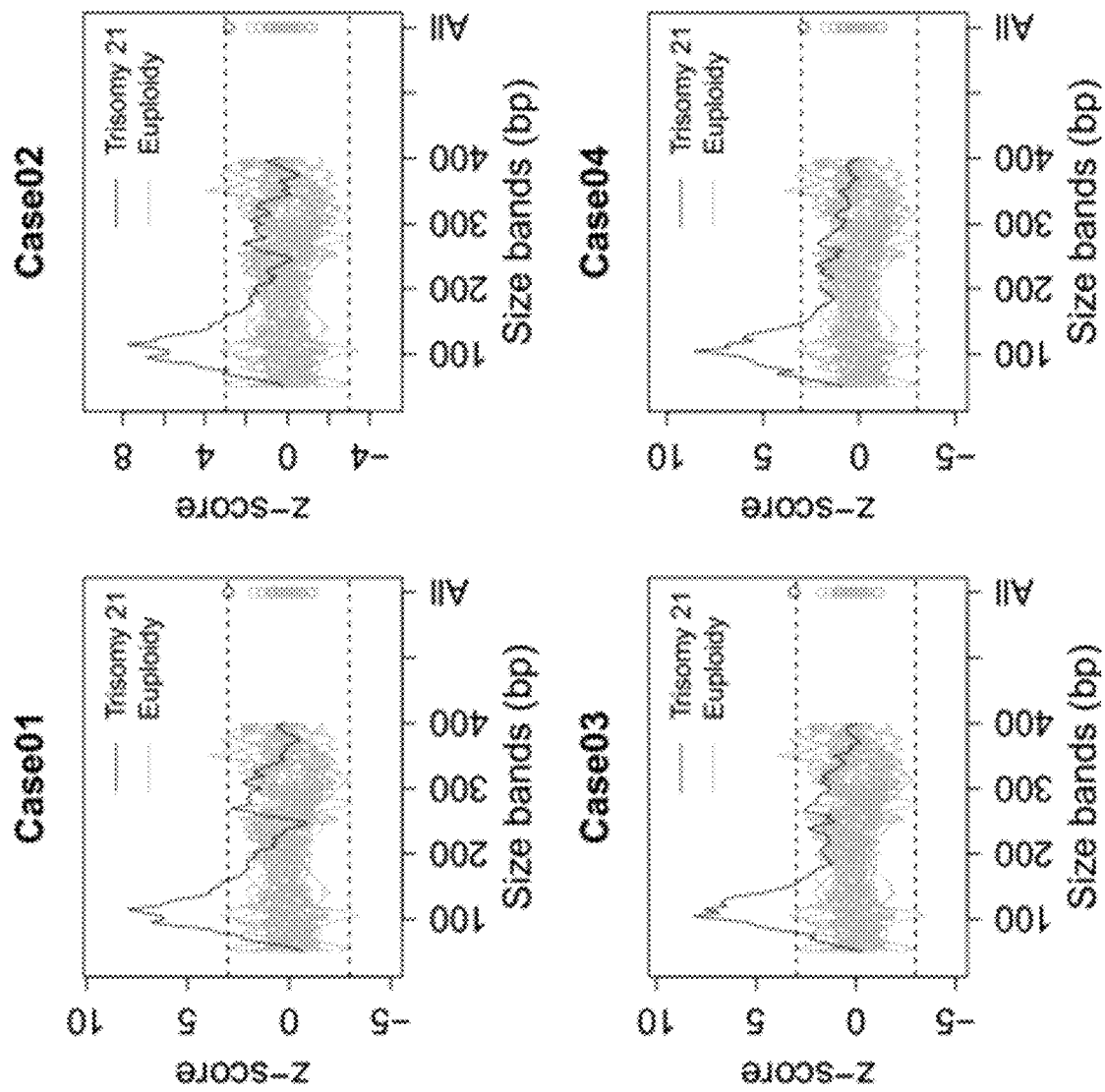
FIG. 3 shows the size-band based changing patterns of the measured genomic representations (GRs) for an aneuploid chromosome across different individual pregnancies with a fetal DNA fraction of 4% according to embodiments of the present invention.
Figure 3:
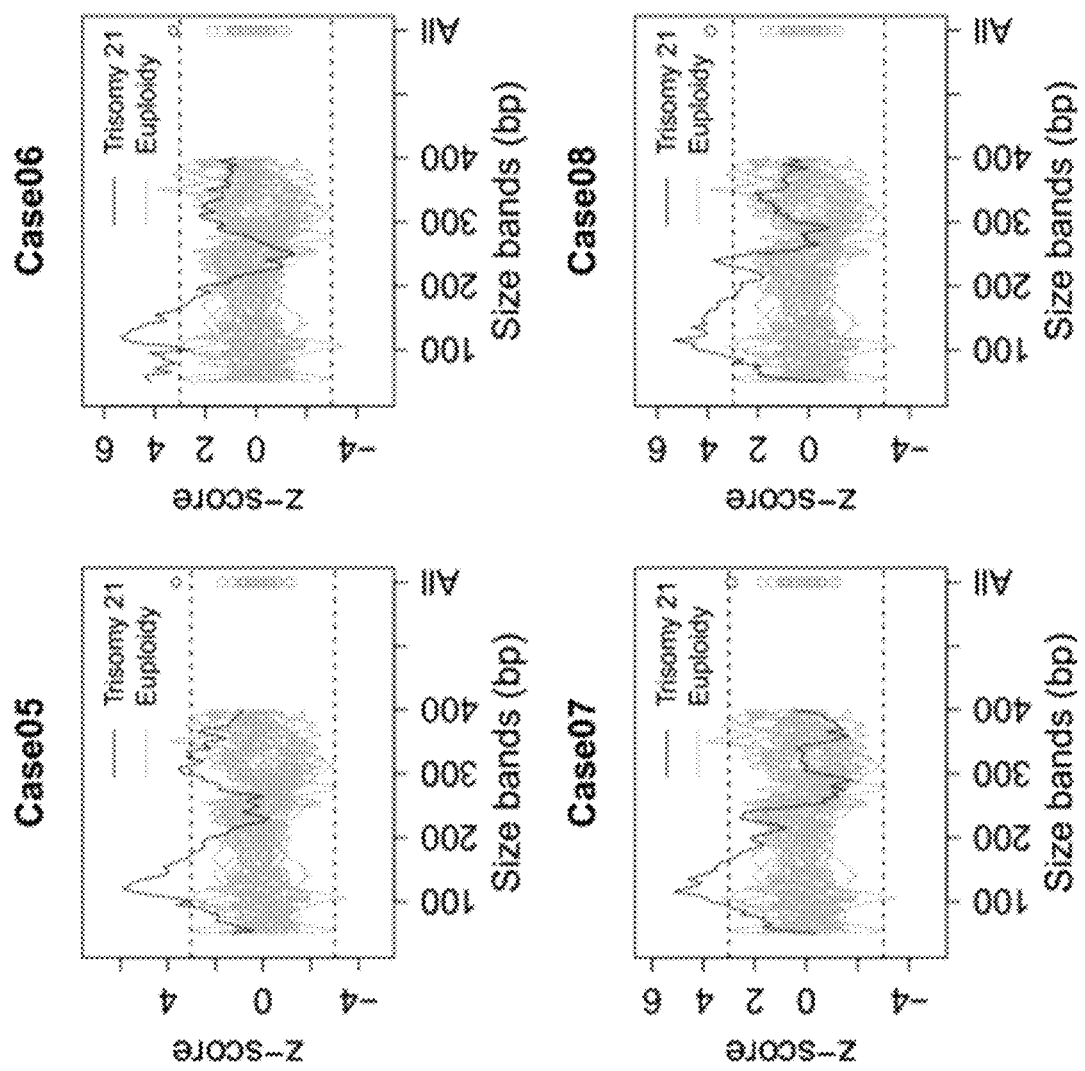
Figure 3:
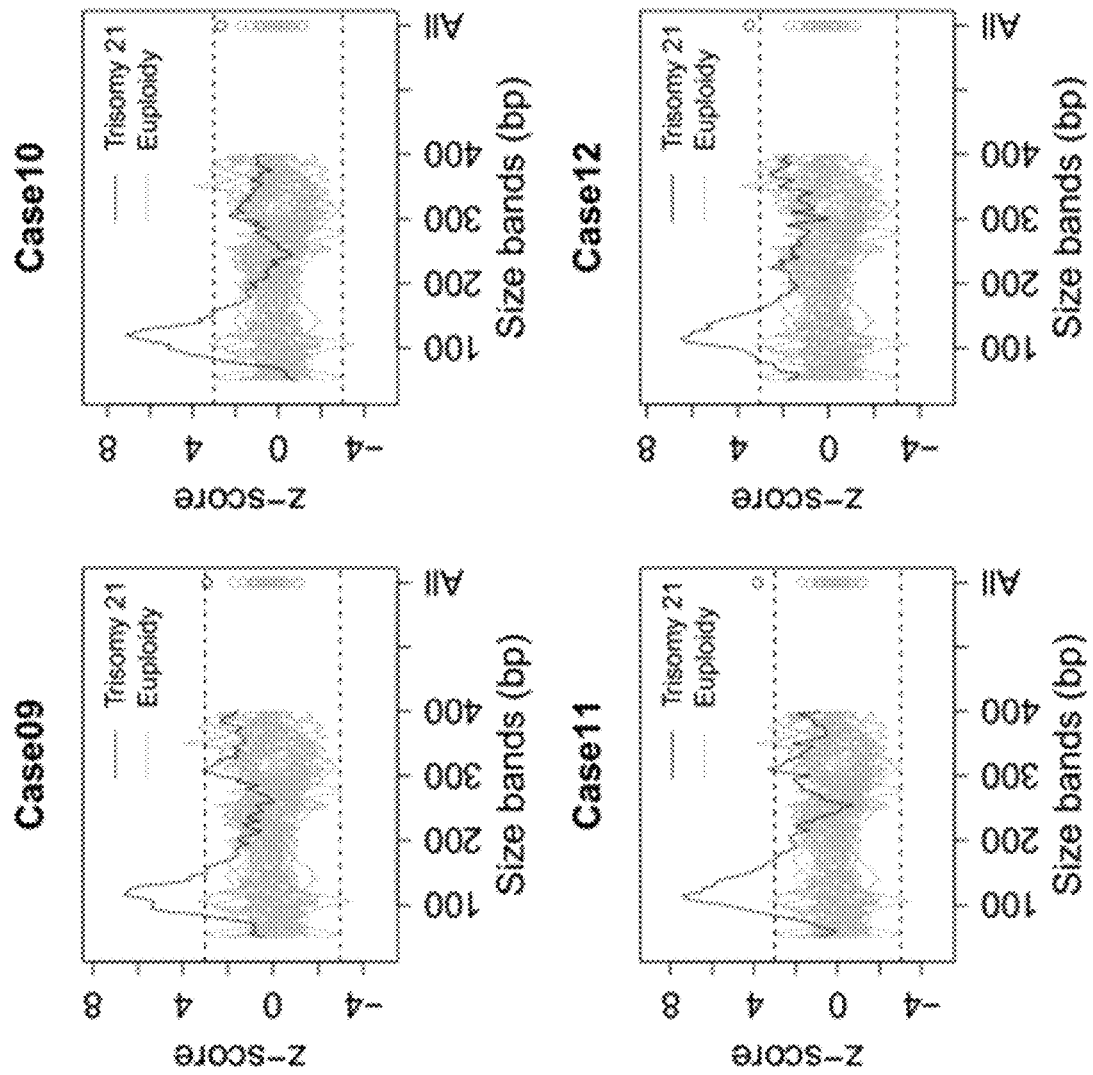
Figure 3:
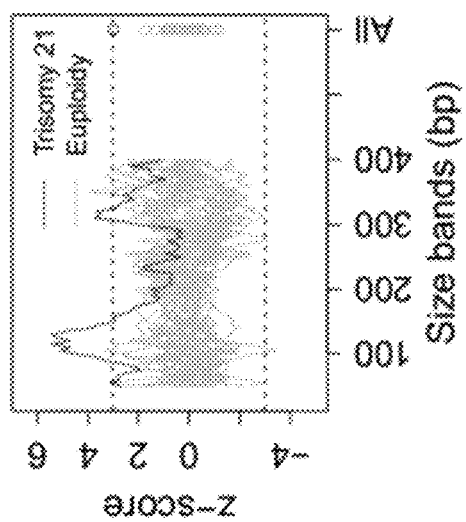
Figure 3:
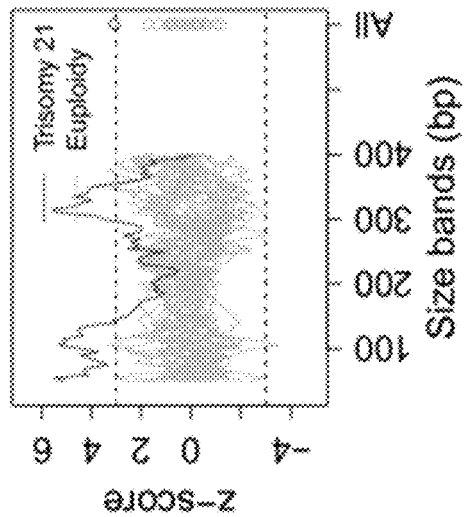
Figure 3:
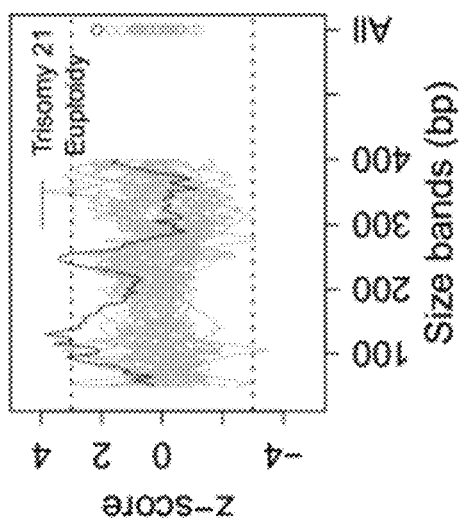
Figure 3:
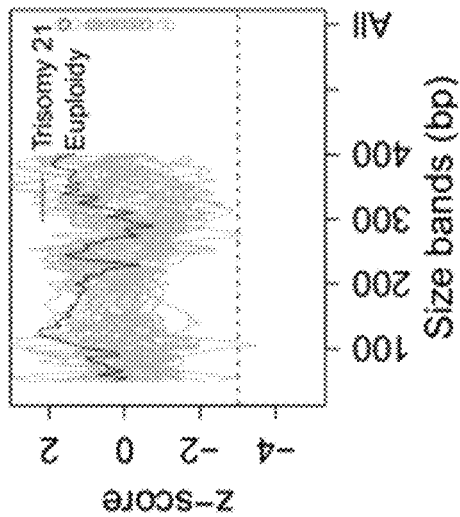
Figure 3:
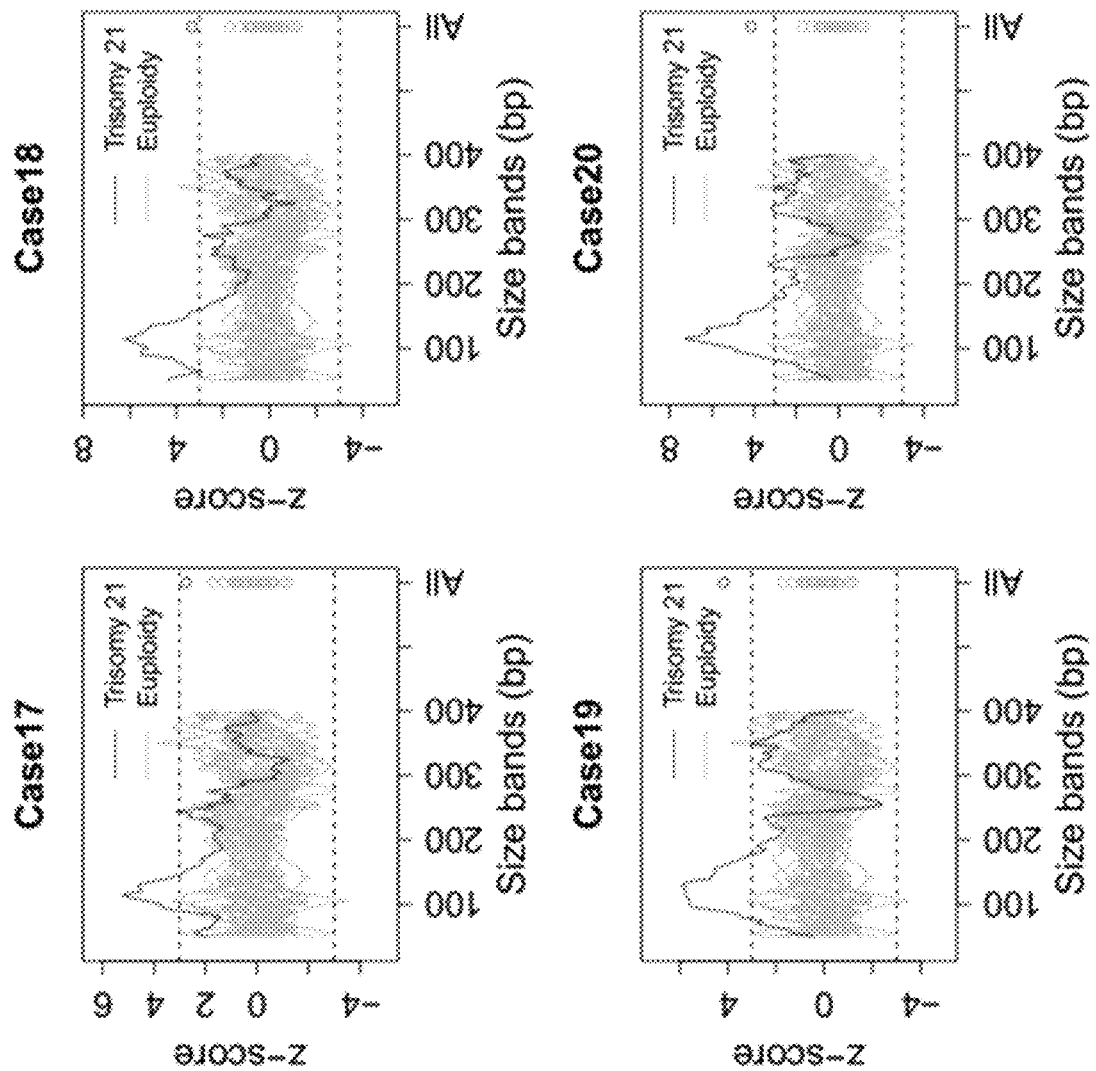
Figure 3:
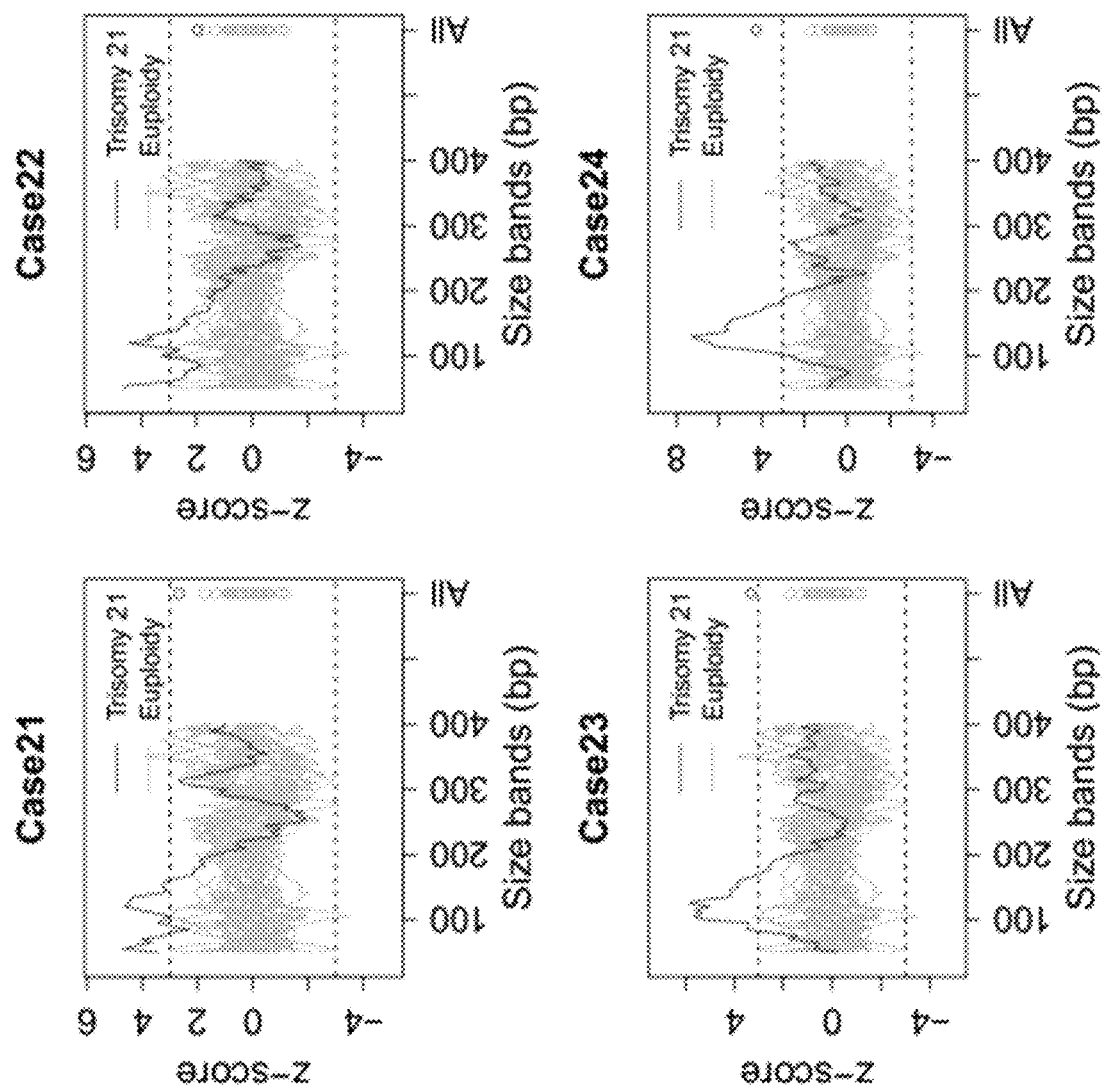
Figure 3:
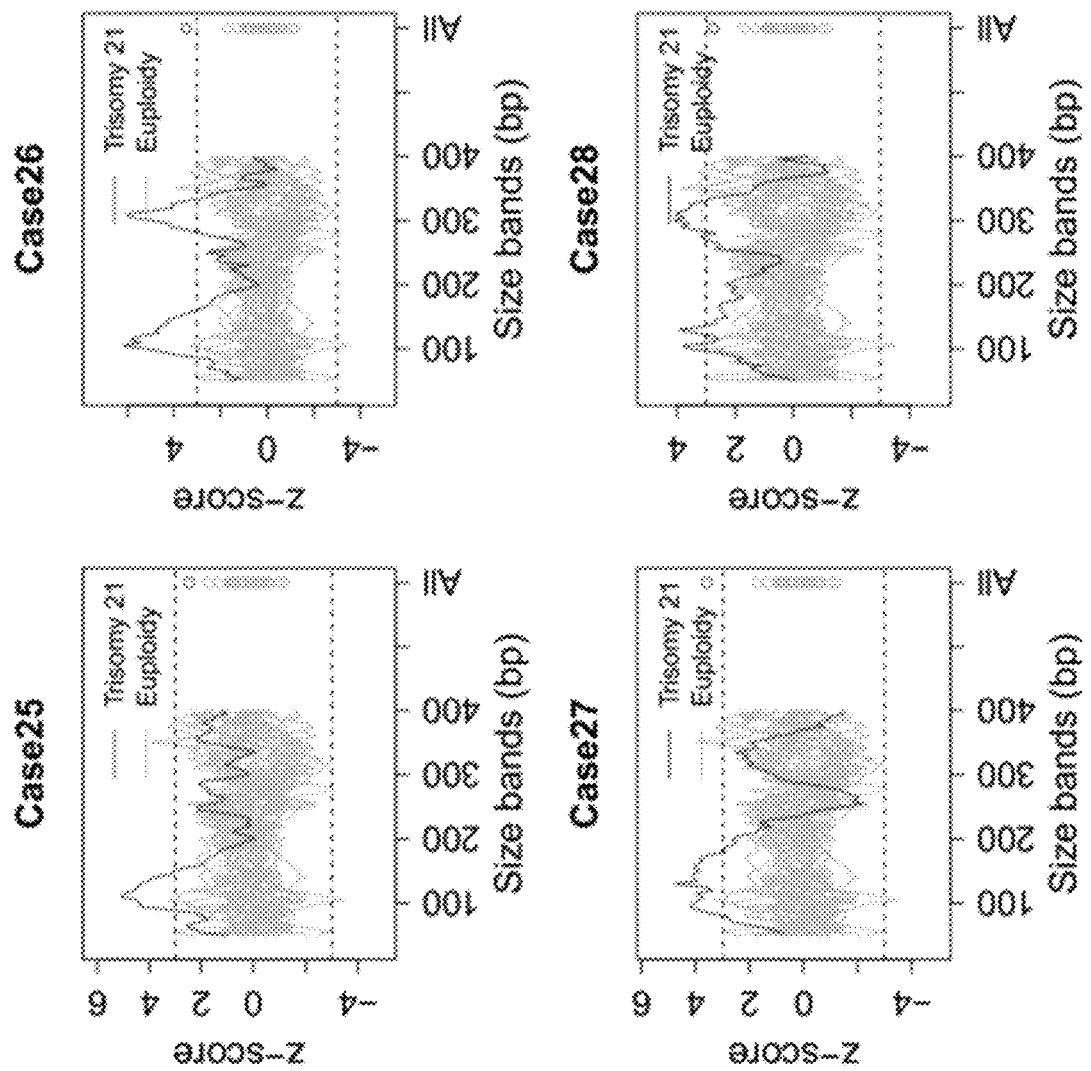
Figure 3:
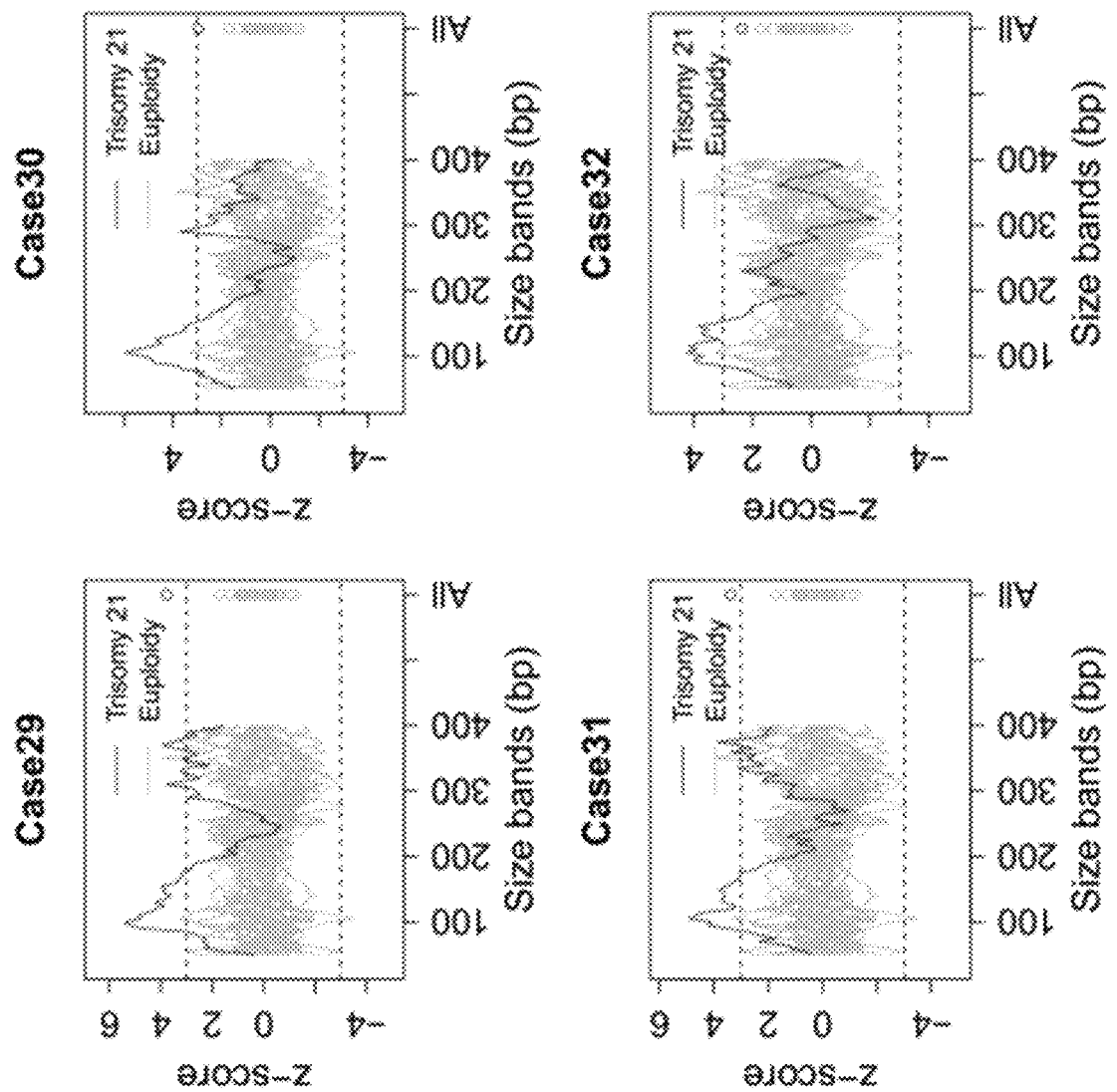
Figure 3:
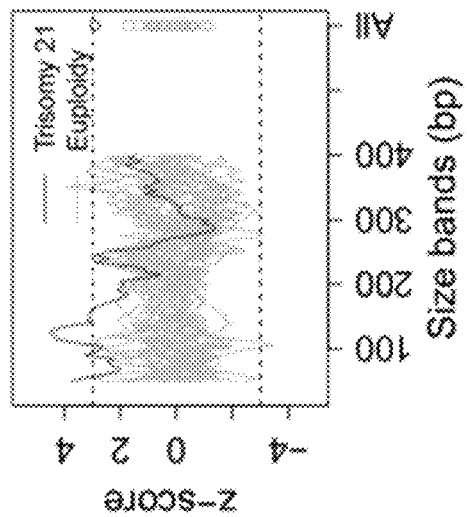
Figure 3:
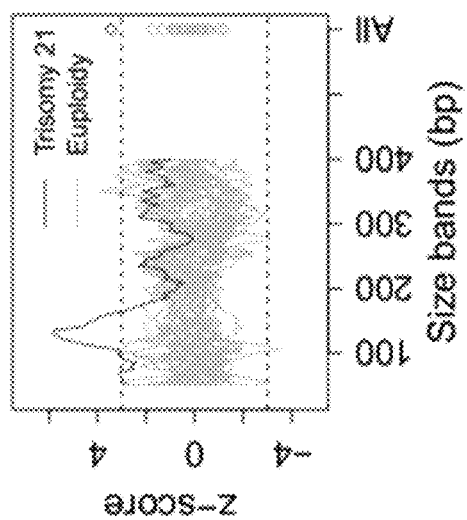
Figure 3:
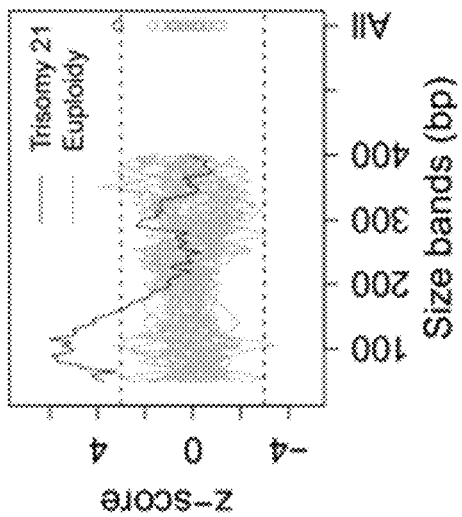
Figure 3:
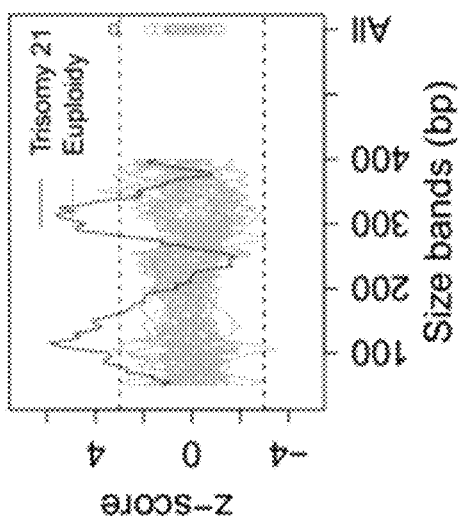
Figure 3:
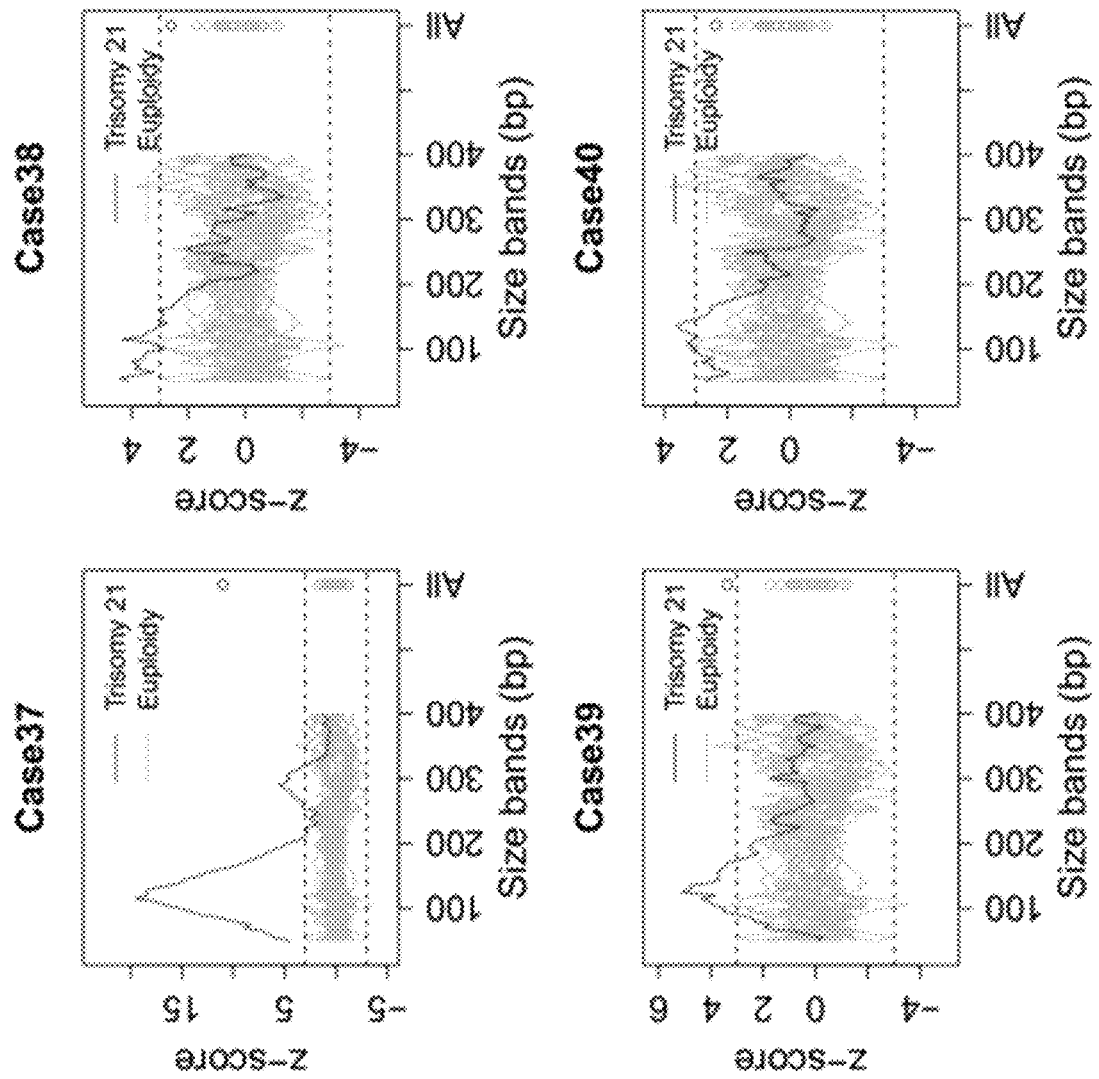
Figure 3:
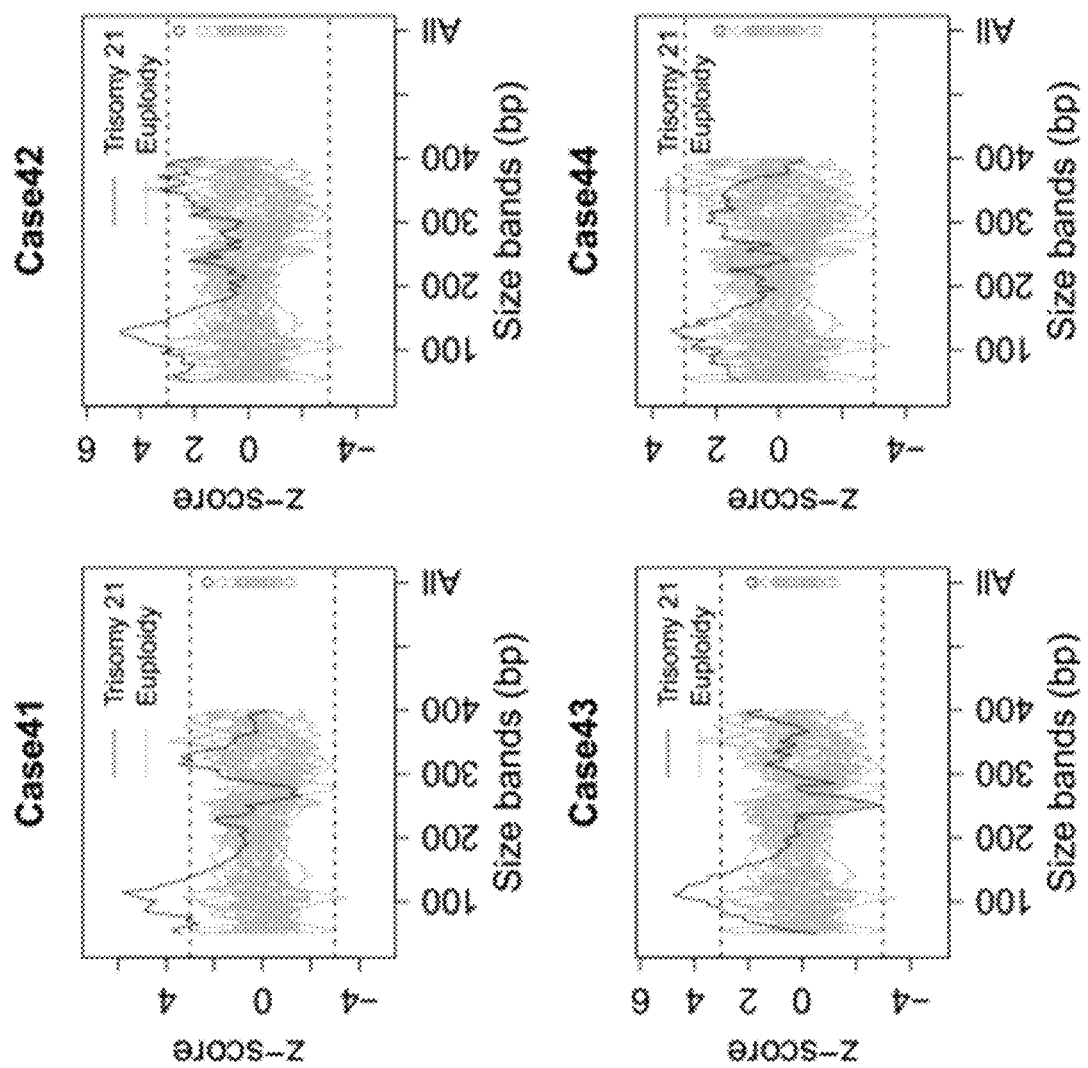
Figure 3:
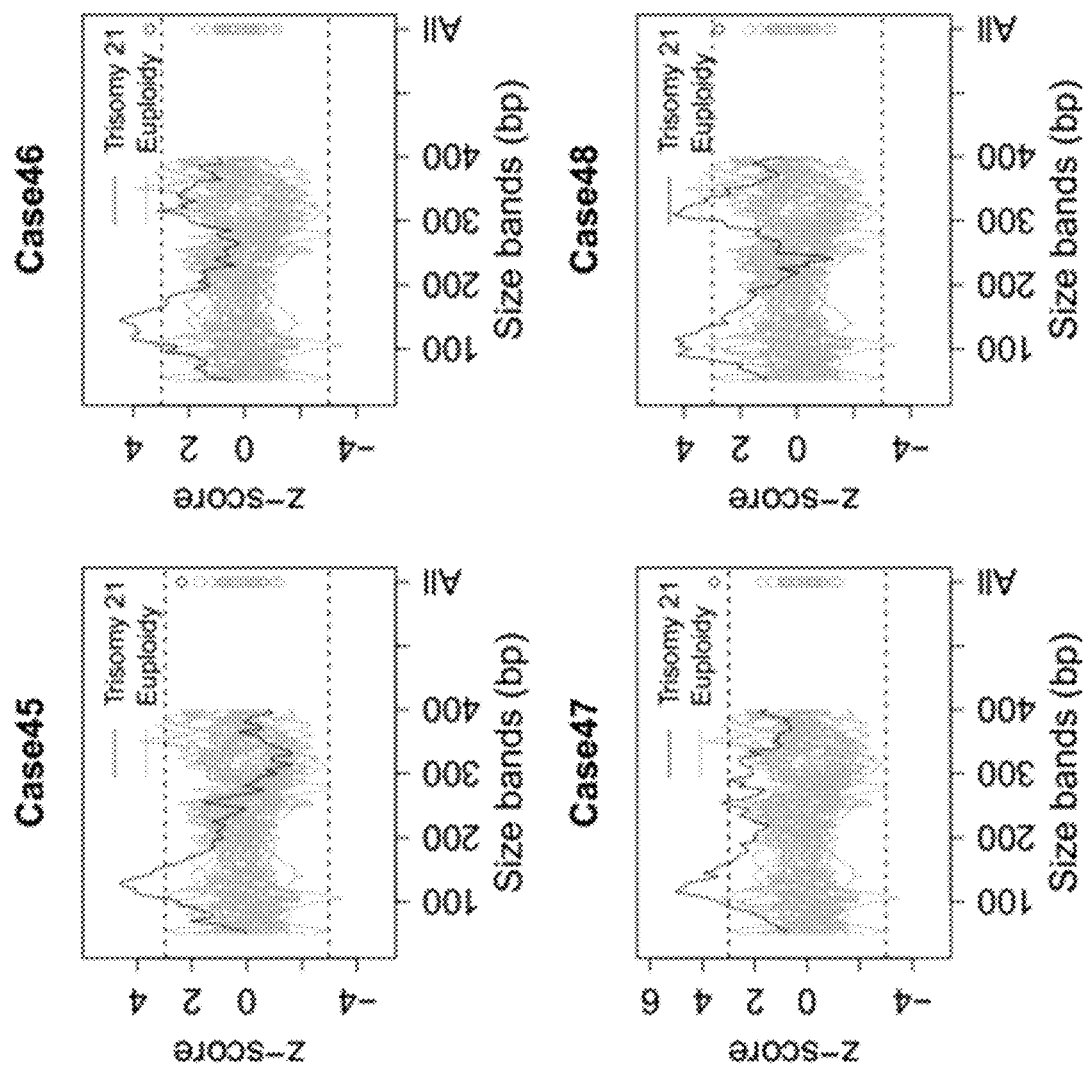

FIG. 3 shows the size-band based changing patterns of the measured genomic representations (GRs) for an aneuploid chromosome across different individual pregnancies with a fetal DNA fraction of 4%. Y-axis indicated z-score values, suggesting the degree of derivation for measured GR in women pregnant with aneuploid fetuses compared with those with euploid fetuses. X-axis indicated different size bands. Red lines (also the darker lines) represented pregnancies with trisomic fetuses; gray lines represented those with euploid fetuses.

FIG. 3 shows that almost all of the cases with trisomic fetuses displayed consistently different size-band based patterns of the measured copy number aberrations compared with those from cases with euploid fetuses. In each case, the line for the size patterns of the trisomy 21 case are distinctly different from the patterns for the euploidy cases, which can allow trisomy 21 to be determined more readily than using the z-score for all size fragments, as shown in FIG. 2B.

We further used heatmap and t-SNE (t-distributed stochastic neighbor embedding) approaches to visualize the data structures between pregnancies carrying trisomic and euploid cases. FIG. 4A shows a heatmap plot of size-band based changing patterns between pregnancies with euploid and trisomy 21 fetuses. Blue (e.g., area 402) is for a feature of a size band that indicates a euploid, while green (e.g., area 404) is for a feature of a size band that indicates trisomy 21. Almost all cases (46/48, 96%) in FIG. 4A involve clustering together trisomy 21 fetus cases. Similarly, almost all cases (62/63, 98%) in FIG. 4A involving a euploid fetus were clustered together.

Figure 4B:
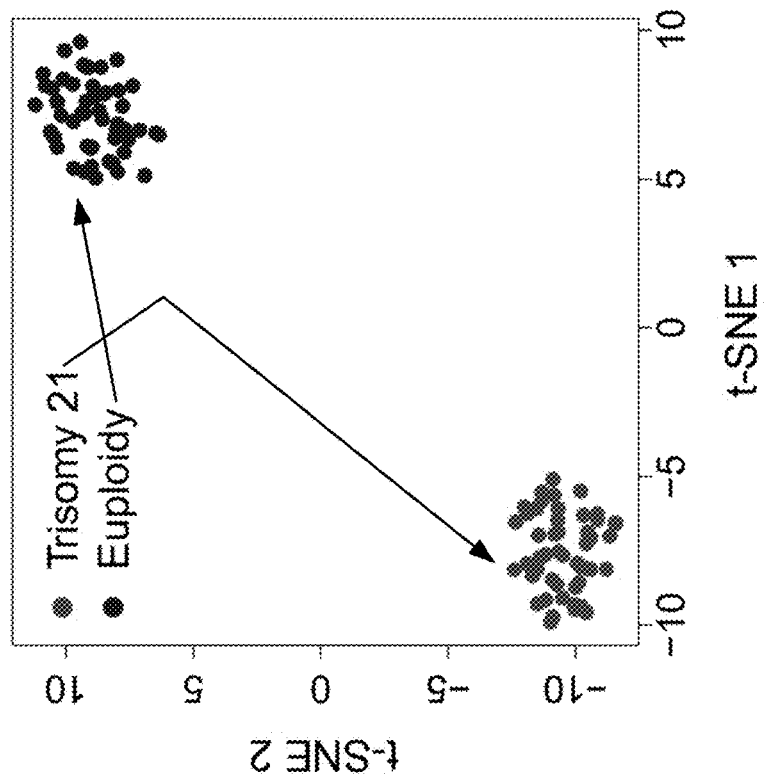
FIG. 4B shows t-SNE (t-distributed stochastic neighbor embedding) plot of size-band based changing patterns between pregnancies with euploid and trisomy 21 fetuses according to embodiments of the present invention.
Figure 4A:
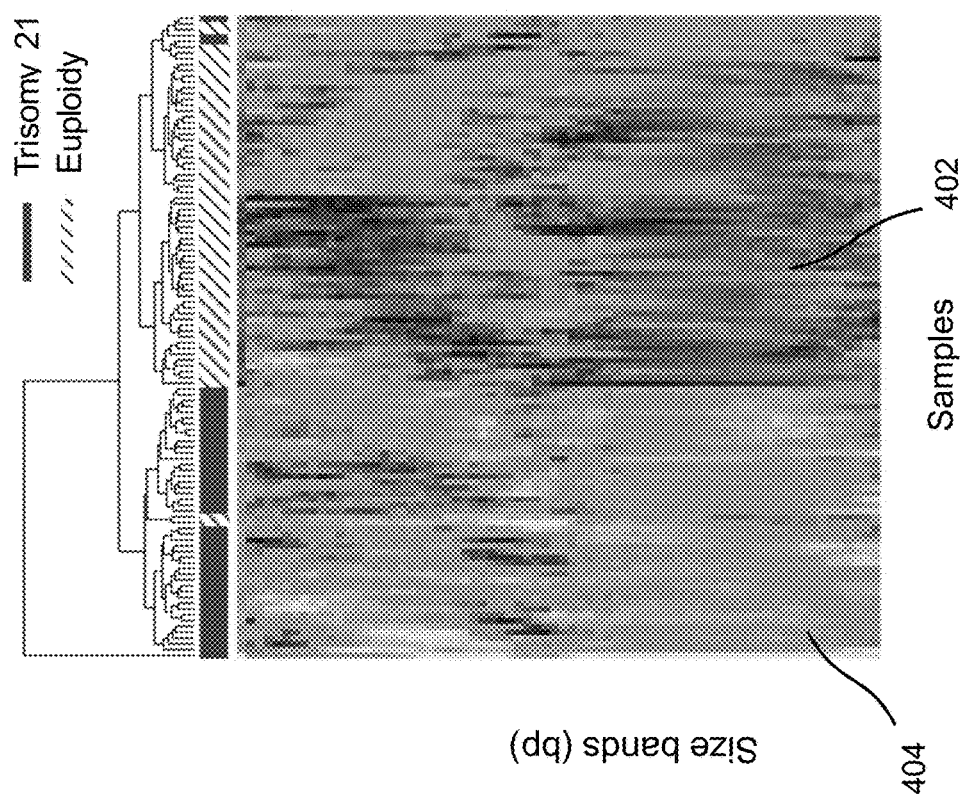
FIG. 4A shows a heatmap plot of size-band based changing patterns between pregnancies with euploid and trisomy 21 fetuses according to embodiments of the present invention.

FIG. 4B shows a t-SNE plot of size-band based changing patterns between pregnancies with euploid and trisomy 21 fetuses. The t-SNE plots are based on two features determined from machine learning. The t-SNE plots gave a consistent result that pregnancies with trisomy 21 cases can be readily differentiated from those with euploid cases (FIG. 4B), suggesting the size-band based shape of measured copy number aberrations in plasma DNA could inform chromosomal aneuploidies for cases with a low fetal DNA fraction such as 4%.

Figure 4C:
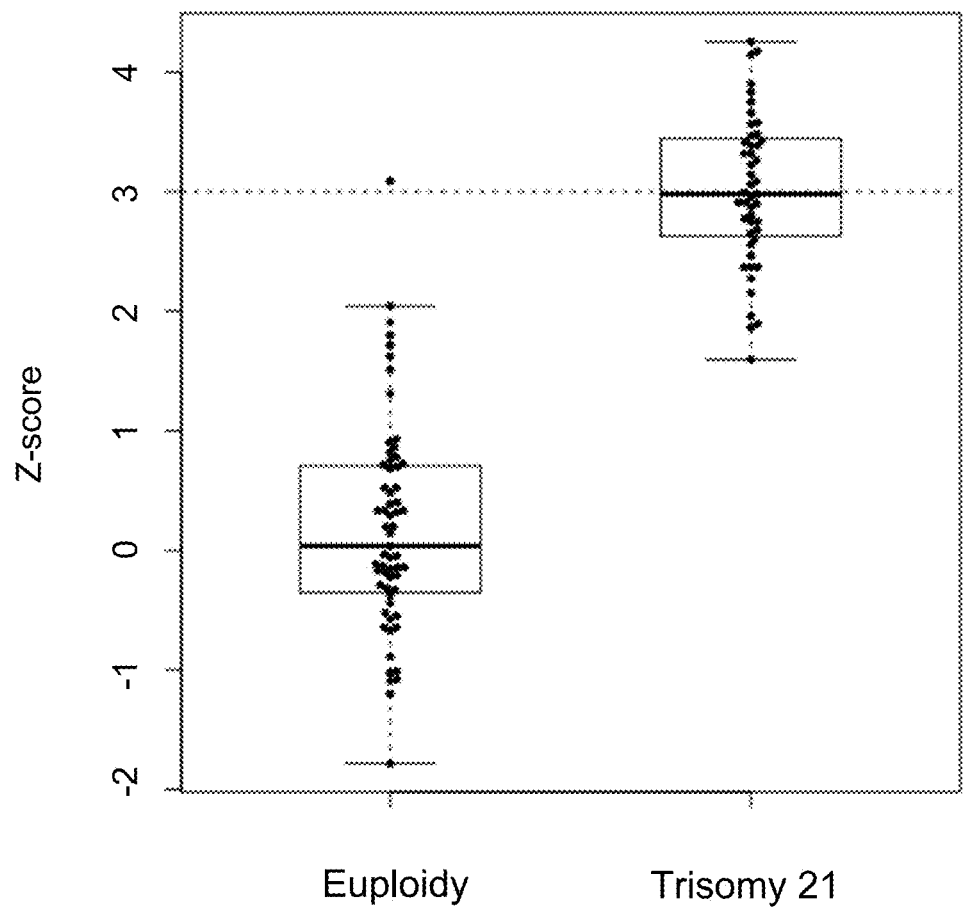
FIG. 4C shows z-score distributions using conventional z-score approach between pregnancies with euploid and trisomy 21 fetuses according to embodiments of the present invention.

FIG. 4C shows z-score distributions using a conventional z-score approach between pregnancies with euploid and trisomy 21 fetuses. The dashed line indicates the z-score threshold of 3. Using a z-score cutoff of 3, the detection rate of trisomy 21 would only be 48%. In other words, 52% of the trisomy 21 would result in a false negative. In addition, FIG. 4C shows that one euploidy pregnancy would result in a false positive for trisomy 21. The conventional z-score approach would result in lower sensitivity and specificity compared to the t-SNE approach in FIG. 4B, which did not generate any false positives or false negatives.

2. Machine Learning Pattern Recognition for Detecting Cases with Low Fetal DNA Fractions.

We utilized a neural network model to further demonstrate the use of a size-band based approach for detecting fetal copy number aberrations. We divided the samples into training and testing dataset. The training dataset included 33 pregnancies with trisomy 21 fetuses and 63 cases with euploid fetuses, and the testing dataset contained 15 trisomy 21 fetuses and 50 euploid fetuses. A neural network constructed with one layer each with 20 neurons was used to learn a model capturing patterns hidden in the size bands. Afterward, we applied this model to the testing dataset.

Figure 5A:
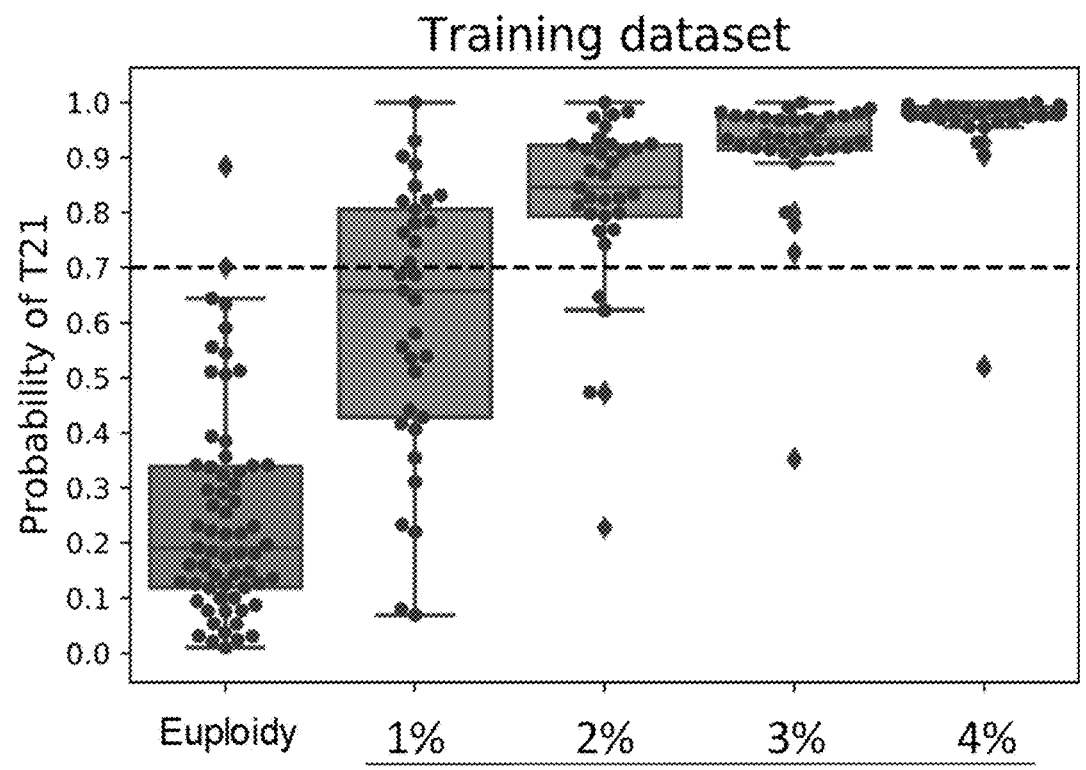
FIGS. 5A and 5B show performance evaluation for neural network based model by learning z-score patterns among different size bands according to embodiments of the present invention.
Figure 5B:
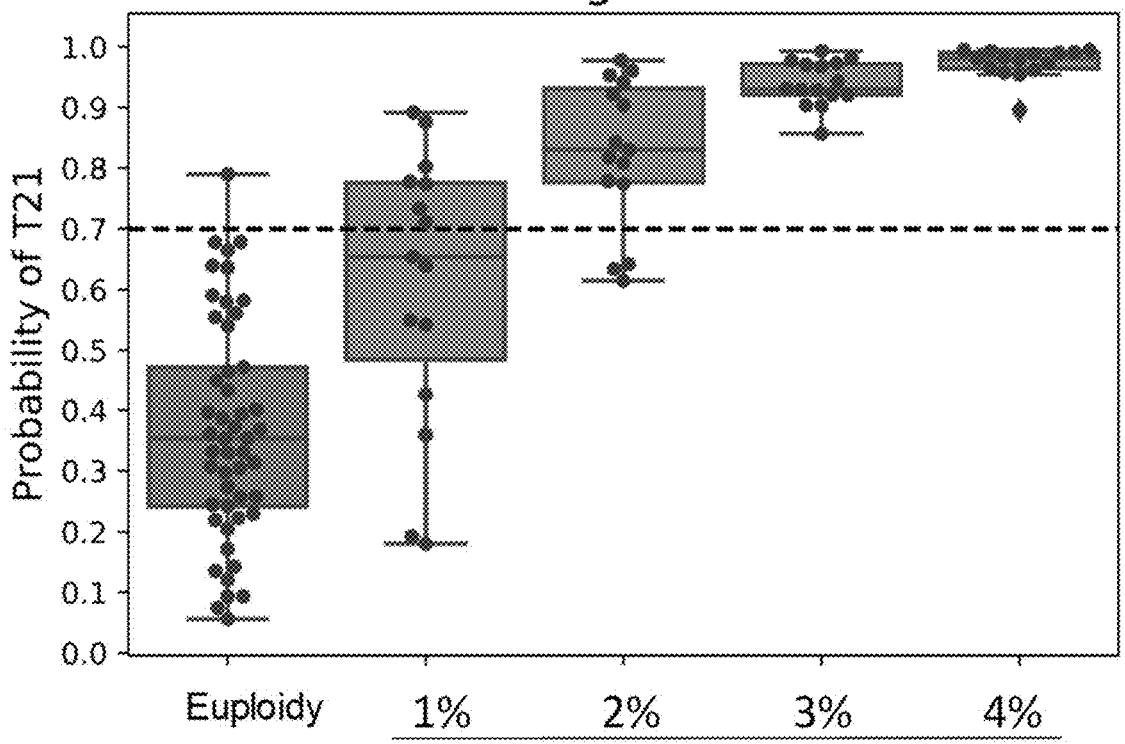

FIG. 5 shows the training dataset and the testing data set for the neural network model. It turned out that with a cutoff of 0.7 for the probability of trisomy 21, we were able to achieve 40%, 80%, 100%, and 100% sensitivities at a specificity of 98% for a fetal DNA fraction of 1%, 2%, 3% and 4%, respectively. Even at a low fetal DNA fraction of 1%, the neural network model shows the ability to identify true positives for trisomy 21.

Machine learning models other than a neural network model may be used to determine patterns and features that can determine a probability of a fetal aneuploidy or cancer in a subject. Training of these machine learning models can use datasets including samples from those affected by a disorder or a clinically-relevant feature and those that are not. Parameters that may be considered for training include bandwidth of the size band, center point of the size band, amounts of DNA molecules, locations of the DNA molecules, epigenomic signals (e.g., methylation), and other variables.

3. Example Method for Detecting a Copy Number Aberration

Figure 6:
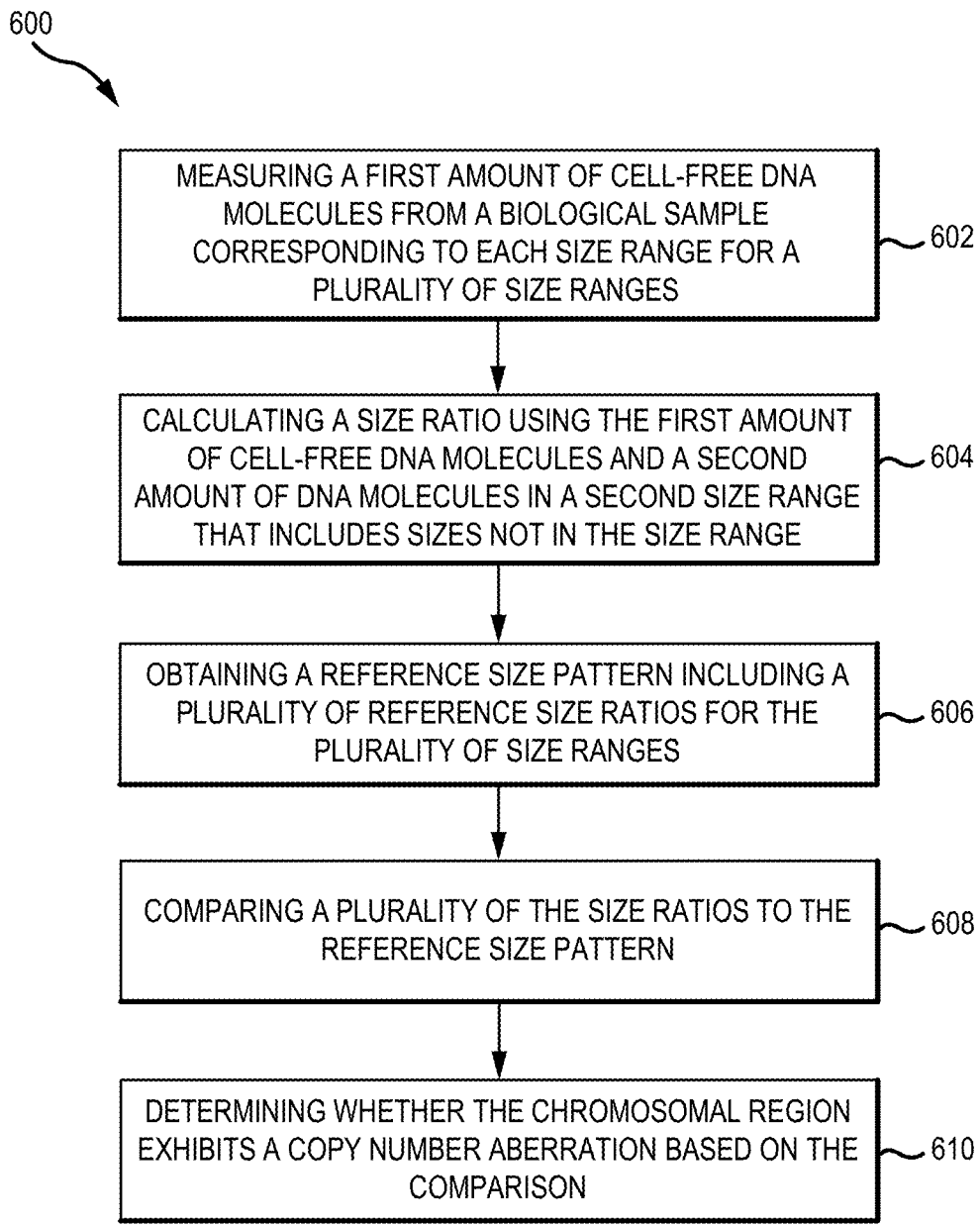
FIG. 6 shows a method of determining whether a chromosomal region exhibits a copy number aberration in a biological sample from a subject according to embodiments of the present invention.

FIG. 6 shows a method 600 of determining whether a chromosomal region exhibits a copy number aberration in a biological sample from a subject. The biological sample may include a mixture of cell-free DNA molecules including clinically-relevant DNA molecules and other DNA molecules. The clinically-relevant DNA molecules may include fetal DNA or maternal DNA. If the clinically-relevant DNA molecules include fetal DNA, then the other DNA may include maternal DNA. If the clinically-relevant DNA molecules include maternal DNA, then the other DNA may include fetal DNA. The clinically-relevant DNA may include tumor DNA, with the other DNA molecules including non-tumor DNA.

At block 602, method 600 may include measuring a first amount of cell-free DNA molecules from the biological sample corresponding to the size range for each size range of a plurality of size ranges. The cell-free DNA molecules may be from a particular genomic region, which may be a chromosome or a portion of a chromosome. For example, the genomic region may be a chromosomal arm. The genomic region may be any region from the genome. In some embodiments, the cell-free DNA molecules may be from multiple disjoint or a continuous genomic region. A size range may be a size band described herein.

The particular size ranges to use may be determined by a machine learning model. Machine learning models can be trained on datasets, and the models can vary which ranges are used (e.g., center point positions and/or the bandwidth of a size range) in order to optimize the sensitivity and specificity for detecting a copy number aberration or a clinical condition. The datasets may include a plurality of reference size patterns. The machine learning model may determine that a certain bandwidth of the size range is advantageous. In addition, the machine learning model may determine that certain size ranges may be more important for a predictive result than others. For example, the size ranges may be determined to be sliding size ranges centered around any size from 100 bp to 150 bp. In other embodiments, the machine learning model may determine that discrete, non-overlapping size ranges may provide improved results over sliding size ranges. A cost function relating to a sensitivity and/or specificity or other accuracy on the training set can be used to update parameters and feature selection (e.g., size ranges to use and specific size ratios) for the machine learning model. A validation data set can also be used to confirm accuracy of the model.

At block 604, method 600 may include calculating for each size range of the plurality of size ranges, by a computer system, a size ratio using the first amount of cell-free DNA molecules corresponding to the size range and a second amount of DNA molecules in a second size range that includes sizes not in the size range. The size ratio may be a z-score or a normalized amount of cell-free DNA molecules (e.g., a fraction, a percentage, or a relative abundance). For example, the size ratio may be a genomic representation (GR). In other embodiments, the size ratio may be a z-score calculated with GR (e.g., the z-score value at a point on curve 202 in FIG. 2B).

Each size range may have a bandwidth, which describes the numerical value of the range of sizes in the size range. For example, the bandwidth may be in a range from 50 bp to 100 bp, 100 bp to 200 bp, 200 bp to 300 bp, or 300 bp to 400 bp. A size range with a bandwidth of 50 bp centered at 100 bp would span from 75 bp to 125 bp. Each size range may be non-overlapping with any other size range of the plurality of size ranges (e.g., discrete size bands such as column 122 and column 124 in FIG. 1). In other embodiments, each size range may overlap with at least one other size range of the plurality of size ranges. In this manner, the size ranges may be considered sliding windows. The sliding windows then result in size ratios values that are continuous over many sizes (e.g., line 126 or line 128 in FIG. 1).

The second size range may be larger than each size range of the plurality of size ranges. The second size range may include all sizes of the cell-free DNA molecules or may include all sizes of the cell-free DNA molecules in the genomic region for the measured cell-free DNA molecules. The second size range may include cell-free DNA molecules from the same genomic regions (e.g., the same chromosome(s) or chromosomal arm(s)) as for the measured cell-free DNA molecules in block 602. The second size range may also include cell-free DNA molecules from genomic regions other than the genomic region for the measured cell-free DNA molecules in block 602. For example, with trisomy 21, cell-free molecules measured at block 602 may be from chromosome 21. In this case, the second size range may include cell-free DNA molecules from other chromosomes (e.g., a different chromosome that serves as a reference or across the entire genome). Method 600 may then also include measuring amounts of cell-free DNA molecules that are in the second size range.

At block 606, method 600 may include obtaining a reference size pattern including a plurality of reference size ratios for the plurality of size ranges. The reference size pattern may be determined from a plurality of reference samples from subjects with a copy number aberration or from subjects without a copy number aberration in the chromosomal region. For example, if the copy number aberration being tested for is related to a fetal aneuploidy, the reference samples may be from subjects known to have a euploid fetus. In other embodiments, the reference samples may be from subjects that are known to have the fetal aneuploidy. Each reference size ratios for the plurality of size ranges may be determined in the same way as the size ratio calculated in block 604, except for a reference sample instead of the biological sample. For example, in FIG. 2B, a size pattern for a reference sample may be any one of the curves in FIG. 2B except for curve 202. The reference size pattern may be a statistical representation of all the size patterns for the reference samples. For example, the reference size pattern may be an average (mean, median, or mode) of all the size patterns. For example, this averaged reference size pattern may be line 126 in FIG. 1.

At block 608, method 600 may include comparing a plurality of the size ratios to the reference size pattern. Comparing the plurality of size ratios to the reference size pattern may include comparing each size ratio of the plurality of size ratios to the reference size ratio at the corresponding size range. For example, the plurality of size ratios may be the points that make up line 128 in FIG. 1. In some cases, the plurality of size ratios may make up only a portion of line 128. Assuming the reference size pattern is line 126 in FIG. 1, comparing the plurality of size ratios to the reference size pattern may include a statistical comparison between the points of line 128 and the reference points of line 126.

Each size ratio for each size range may be determined to be statistically similar to the reference size ratio at the corresponding size range. Statistical similarity may be determined using a threshold. The threshold may indicate how close the size ratio needs to be to the reference size ratio. The threshold may be a certain number of standard deviations (e.g., 1, 2, or 3) from the reference size ratio. In some embodiments, not every size ratio needs to be statistically similar to the reference size ratio. Instead, a minimal number of size ratios may be statistically similar. For example, 80%, 85%, 90%, or 95% of the size ratios may be statistically similar to the corresponding reference size ratio.

Comparing the plurality of the size ratios to the reference size pattern may include comparing the plurality of the size ratios to a plurality of threshold values that are determined from the plurality of reference samples. For example, each size range may have a different threshold value, which may be based on a standard deviation for reference samples. A single size range may also have different threshold values, with each threshold value associated with a different certainty level that the size ratio is different from the reference samples. Comparing may include counting the number of threshold values exceeded and determining if the number exceeds an amount or fraction (e.g., 0.5, 0.6, 0.7, 0.8, or 0.9). If the number exceeds the amount, then a copy number aberration may be determined to be exhibited by the chromosomal region.

In some embodiments, comparing the plurality of the size ratios to the reference size pattern may include determining a size pattern including the plurality of size ratios for the plurality of size ranges. The size pattern may be a graph relating the size ratios to size ranges. For example, the size pattern may be line 128 in FIG. 1, curve 202 in FIG. 2B, or any of the Trisomy 21 lines in FIG. 3. The size pattern may be determined to have a similar shape as the reference size pattern. Determining a similar shape may include determining that the slopes (e.g., first derivatives) and/or the inflection points (e.g., second derivatives) of the size pattern are similar to those in the reference size pattern. The similarity of the slopes or inflection points may be determined using a threshold, which may indicate a statistical significance (e.g., a certain number of standard deviations).

In some embodiments, comparing the plurality of the size ratios to the reference size pattern may include a comparison using machine learning, including a neural network. A machine learning model can be used to determine how to calculate the size ratio, how to compare the size ratio to the reference size pattern, and/or how to determine if a size pattern is similar to the reference size pattern. How to calculate the size ratio may include determining the bandwidth of the size range and the size and bandwidth of the second size range. How to compare the size ratio to the reference size pattern may include determining weightings for different size ranges, and whether to use zeroth, first, or second derivatives of the size pattern. How to determine if a size pattern is similar to the reference pattern may include determining threshold values for similarity.

Obtaining the reference size pattern and comparing the plurality of the size ratios to the reference size pattern may include inputting the plurality of the size ratios to a machine learning model. The machine learning model may be trained using a plurality of training size patterns from the plurality of reference samples. The trained machine learning model (e.g., a neural network) may output a probability of a sample having an aberration in a chromosomal region.

At block 610, method 600 may include determining whether the chromosomal region exhibits a copy number aberration based on the comparison. The copy number aberration may be an aneuploidy, including trisomy 21, trisomy 18, trisomy 13, and sex chromosome aneuploidies. The copy number aberration may be an indication of cancer. Method 600 may also include treating the subject for cancer or developing a plan for an aneuploidy.

If the reference size pattern is determined from the plurality of reference samples from subjects with a copy number aberration and the comparison shows that the size ratios or the size pattern are similar to the reference size pattern, then the chromosomal region may be determined to exhibit a copy number aberration. And if the comparison shows differences between the size ratios or the size pattern and the reference size pattern, then the chromosomal region may be determined to not exhibit a copy number aberration. In some embodiments, a probability of exhibiting the copy number aberration may be determined. The probability may be correlated with how similar or dissimilar the size ratios or the size pattern is to the reference size pattern. The probability may be determined using a machine learning model, including a neural network or any model described herein.

Alternatively, if the reference size pattern is determined from the plurality of reference samples from subjects without a copy number aberration and the comparison shows that the size ratios or the size pattern are similar to the reference size pattern, then the chromosomal region may be determined to not exhibit a copy number aberration. And if the comparison shows differences between the size ratios or the size pattern and the reference size pattern, then the chromosomal region may be determined to exhibit a copy number aberration.

C. Improved Accuracy at Low Fetal Fractions

To benchmark the performance of approach by taking advantage of size-band based patterns of measured copy number aberrations in plasma DNA, we also calculated the specificities and sensitivities across different fetal DNA fractions such as 4%, 3%, 2%, and 1% using the traditional z-score (Chiu et al. *Proc Natl Acad Sci USA* 2008; 105: 20458-20463) and size selection methods. Since the fetal DNA gave a maximum of measured fetal DNA fraction present in maternal plasma DNA at 120 bp (FIG. 2A), we hypothesized that the size band around 120 bp would give a better performance than using all DNA fragments. To this end, we selected a size band from 105 to 155 bp and calculated the corresponding z-scores.

Table 2 shows the performance of size-band based pattern recognition compared with the conventional counting-based methods with and without a size selection. The use of size-band based patterns of measured copy number aberrations in plasma DNA gave a superior performance in comparison with the traditional z-score and size selection approaches. For example, in our study, at the fetal DNA fraction of 3%, the recognition of size-band based patterns of measured copy number aberrations gave a 100% sensitivity with a specificity of 98%. As comparison, conventional counting based approach only gave a sensitivity of 10% and specificity of 98%. Using size selection of fragments below 150 bp, the sensitivity improved to 43%. However, selection of fragments of even shorter size to 120 bp, the sensitivity reduced to 20%. This indicates that the method proposed in this invention provides much better analytical performance over existing approaches using size selection.

TABLE 2

| Fetal DNA fraction | Conventional counting-based approach | | | | | | Size-band based patterns of measured copy number aberrations (new invented approach) | |
|---|---|---|---|---|---|---|---|---|
| | With a size selection (<120 bp) | | With a size selection (<150 bp) | | Without a size selection | | | |
| | Specificity | Sensitivity | Specificity | Sensitivity | Specificity | Sensitivity | Specificity | Sensitivity |
| 4% | 96% | 47% | 100% | 75% | 98% | 48% | 98% | 100% |
| 3% | 96% | 20% | 100% | 43% | 98% | 10% | 98% | 100% |
| 2% | 96% | 16% | 100% | 14% | 98% | 2% | 98% | 80% |
| 1% | 96% | 6% | 100% | 6% | 98% | 2% | 98% | 40% |

In addition to increased accuracy, embodiments of the present invention may allow for a reduced amount of sequencing. Size pattern approaches may not involve discarding sequence reads of certain sizes, and as a result, more sequence reads at a given sequencing depth are used in the analysis. Size pattern approaches then may not require additional sequencing to provide more reads in a certain size range. Moreover, even with higher sequencing depth at certain low levels of fetal fraction, approaches that do not use size bands or size patterns may still not accurately determine trisomy 21. The low fetal fraction may not result in a statistically significant size difference between trisomy 21 and a euploidy case if size bands or size patterns are not analyzed. Moreover, while existing approaches using size selection without size bands or size patterns may be used to complement other techniques, embodiments using size bands or size patterns may be used independently to determine trisomy 21 or a copy number aberration.

In this study, we developed a novel method to allow NIPT to be performed for a pregnant woman with a low fetal DNA fraction, for example extending to 2%. With more samples used to train a neural network model or other machine learning model, we would expect to further lower the limit of detection. We took advantage of the fact that the degree of copy number changes in maternal plasma DNA would exhibit distinct patterns in relation to different size bands between pregnancies with trisomic and euploid fetuses. This is an important step to achieve a broad population coverage by lowering the limit of non-invasive detection of fetal chromosomal aneuploidies extending to a fetal DNA fraction of below 2%. Using conventional approaches, pregnancies involving a fetal DNA fraction of below 4% were not suitable for NIPT and generally would be issued with a non-reportable result or test failure.

Our new approach has potential not only to reduce the false negative rate because of the lower limit of detection, but also to improve actual PPVs because there were a number of reports showing that the risk of carrying aneuploidies would increase in those pregnancies with a fetal DNA fraction below 4% (Norton et al. *N. Engl. J. Med.* 2015; 372:1589-1597). Previously, some workers argue that pregnancies with low fetal DNA fraction should receive genetic counseling and be offered comprehensive ultrasound evaluation and diagnostic testing because of an increased risk of aneuploidy (Yaron *Prenat. Diagn.* 2016; 36:391-396). Since the fetal DNA fraction is generally inversely correlated with maternal weight (Wang et al. *Prenat. Diagn.* 2013; 33:662-666; Hudecova et al. *PLoS One* 2014; 9:e88484), the pregnancies with high body mass index would particularly benefit from the ability of such a size-band based approach to sensitively tackle the scenarios with a low fetal DNA fraction. Another use of our new approach would be to allow NIPT to be performed earlier in gestation (e.g. before 10 weeks of gestation), when the fetal DNA fractions are generally lower.

D. Methylation Level Analysis in Oncology

Copy number aberrations (CNA) are also present with many cancers. As a result, CNAs may be used to determine a level of cancer in a subject. In addition, cancer patients often show higher levels of methylation in certain genomic regions. Methylation markers therefore may also be used in combination with size band analysis to determine the level of cancer.

1. Size Pattern Analysis with Methylation

We reasoned that other types of cancer associated aberrations such as methylation would be also able to be used for constructing the specific size-band based patterns which could be differentiated from the non-cancer subjects. Therefore, we also further analyzed 4 plasma DNA samples from HCC patients as mentioned above. We used, but are not limited to, targeted bisulfite sequencing to quantify the methylation levels for those regions that are supposed to be unmethylated in organs of healthy subjects but that have a much higher chance of being methylated in cancer patients. We applied the size-band based approach described herein to explore the size-band associated patterns in terms of methylomic aberrations in comparison with the healthy subjects. Methylation is described further in U.S. application Ser. No. 13/842,209, filed Mar. 15, 2013 (issued as U.S. Pat. No. 9,732,390 on Aug. 15, 2017) and U.S. application Ser. No. 14/803,692 filed Jul. 20, 2015, the contents of both are incorporated herein by reference for all purposes.

Figure 7:
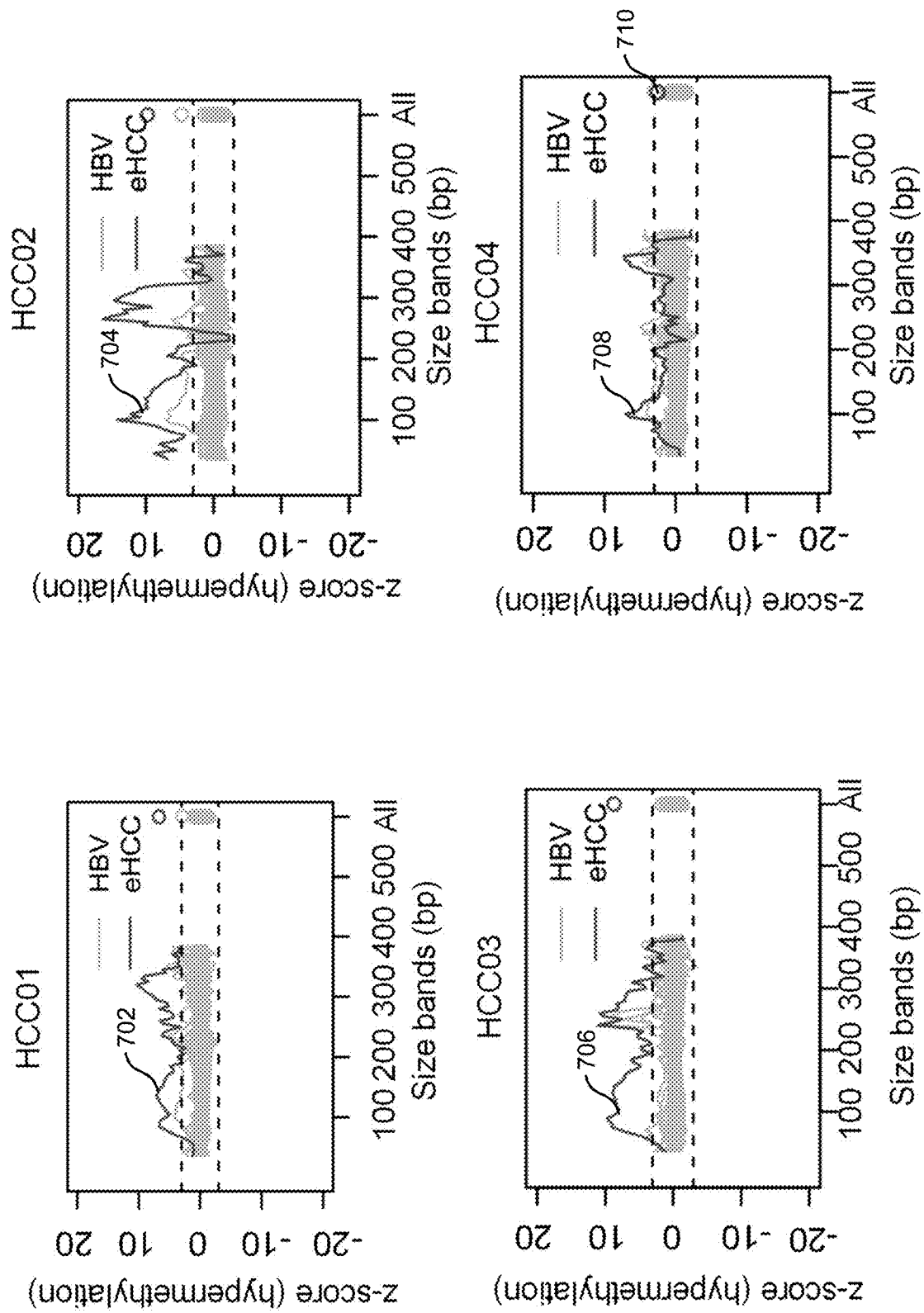
FIG. 7 shows size-band based changing patterns of the measured methylation in plasma DNA of hepatocellular carcinoma (HCC) patients according to embodiments of the present invention.

FIG. 7 shows size-band based changing patterns of the measured methylation in plasma DNA of hepatocellular carcinoma (HCC) patients. The z-scores are calculated by calculating a mean average methylation level for reference samples from healthy subjects known not to have HCC and calculating the standard deviation associated with the average methylation level. The z-score at each size band is calculated as the difference between the methylation level at that size band and the mean average methylation level, and the difference divided by the standard deviation. The dashed lines in FIG. 7 indicate a z-score of +3 or −3, which may be used to show statistical significance from the mean average methylation level.

Red or darker lines 702, 704, 706, and 708 represented early HCC (eHCC) and gray lines represented the chronic hepatitis B virus (HBV) carriers without HCC. In FIG. 7, we could ascertain distinct size-band patterns of methylomic abnormalities associated with HCC patients (lines 702, 704, 706, and 708), which allowed for identifying cancer patients from HBV carriers (gray lines) in HCC01, HCC02 and HCC03. Lines 702, 704, and 706 show patterns that have at least two peaks that appear considerably higher from the gray lines for HBV samples. Line 708 is closer to the gray lines but still has two peaks higher than the gray lines for the HBV samples.

The right-most data in each graph, labeled "All," is the pooled z-score for all data, regardless of size-band. For HCC04, the non-random size-band based curving patterns turned out to be more informative than the overall degree of aberrant methylations with the use of all fragments (represented by circle 710). Different genomic regions were used in the different graphs. Chromosomal arm 1q was used for HCC01 and HCC04, 10p was used for HCC02, and 19q was used for HCC03. In other embodiments, size-band based changing patterns of, for example but not limited to, hypomethylation, point mutations, hydroxymethylation, fragmentation ends, etc. could be also used for detecting cancers.

2. Example Method for Determining a Level of Cancer

Figure 8:
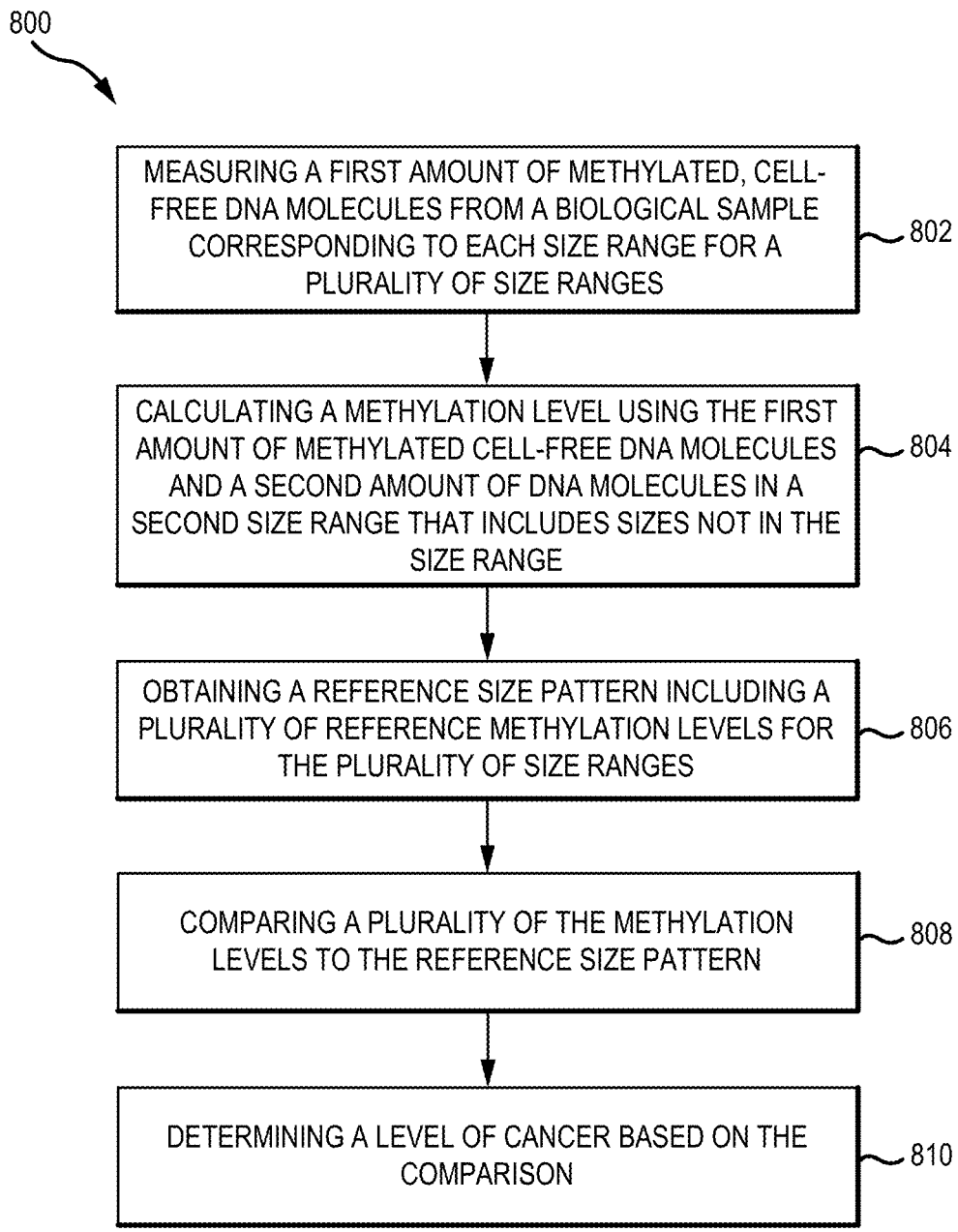
FIG. 8 shows a method of determining a cancer classification in a biological sample from a subject according to embodiments of the present invention.

FIG. 8 shows a method 800 of determining a level of cancer in a biological sample from a subject. The biological sample may include a mixture of cell-free DNA molecules. The cell-free DNA molecules may include tumor DNA molecules and non-tumor DNA molecules.

At block 802, method 800 may include measuring a first amount of methylated cell-free DNA molecules from the biological sample corresponding to a size range for each size range of a plurality of size ranges. The methylated cell-free DNA molecules may be from a chromosomal arm. Measuring amounts of methylated cell-free DNA molecules corresponding to a size range may be performed as described in method 600 or any other method described herein, except that the cell-free DNA molecules are methylated. The first amount of methylated cell-free DNA molecules may be from one or more genomic regions. A genomic region may be a chromosomal arm, e.g., 1p, 1q, 8p, 8q, 13q, or 14p. Various combinations of genomic regions may be used. The particular regions to use can be determined by analyzing accuracy for various combinations of regions for determining a level of cancer on a training set of samples having a known level of cancer.

At block 804, method 800 may include calculating for each size range, by a computer system, a methylation level using the first amount of methylated cell-free DNA molecules corresponding to the size range and a second amount of DNA molecules in a second size range that includes sizes not in the size range. The second amount may be of methylated cell-free DNA molecules. In these or other embodiments, the second amount may include non-methylated cell-free DNA molecules.

The methylation level may be a z-score or a normalized amount of DNA molecules (e.g., a fraction, a percentage, or a relative abundance) of DNA molecules that are methylated or unmethylated at one or more sites. For example, the methylation level may be a ratio of the first amount to the second amount. In other embodiments, the methylation level may be a z-score. The z-score may be calculated using a ratio of the amount of cell-free DNA molecules corresponding to the size range to the second amount. The difference between the calculated ratio and a mean average ratio is then divided by the standard deviation to determine the z-score. The mean average ratio may be an average methylation level for a control group (e.g., non-cancer patients, reference samples, or genomic region not associated with cancer). If the methylation level is a z-score, a methylation level for a size range may be any point on lines 702, 704, 706, and 708 in FIG. 7.

At block 806, method 800 may include obtaining a reference size pattern including a plurality of reference methylation levels for the plurality of size ranges. The plurality of size ranges may be determined by a machine learning algorithm and may be determined in the same way as described for method 600. The reference size pattern may be determined from a plurality of reference samples from subjects with cancer or from subjects without cancer. For example, the reference samples may be from patients known not to have HCC or any type of cancer. The reference size pattern may be based on data from chronic HBV carriers without HCC. For example, the reference size pattern may be any of the gray lines for HBV in FIG. 7. In some embodiments, the reference size pattern may be a statistical representation of all the size patterns for the reference samples, as explained with method 600.

At block 808, method 800 may include comparing a plurality of the methylation levels to the reference size pattern. Method 800 may include comparing each methylation level of the plurality of size ratios to the reference methylation level at the corresponding size range. Comparing the methylation levels to the reference size pattern may be performed in the way the size ratios are compared to the reference size pattern in method 600, except with methylation levels in place of size. Method 800 may include determining that each methylation level is statistically similar to the reference methylation level at the corresponding size range. In some embodiments, method 800 may include determining that each methylation level or some methylation levels are statistically different to the reference methylation level at the corresponding size range.

In some embodiments, comparing the plurality of methylation levels to the reference size pattern may include determining a size pattern including the plurality of methylation levels for the plurality of size ranges. The size pattern may be compared to the reference size pattern. The size pattern may be determined to have a similar shape as the reference size pattern. Comparisons to a reference size pattern in method 800 may be analogous to comparisons to the reference size pattern in method 600.

If the first amount of methylated cell-free DNA molecules are from more than one genomic region, the methylation levels may be analyzed based on their location in the genome. The plurality of methylation levels may include a multi-dimensional vector. The multi-dimensional vector may be N×M with N being the number of size ranges and M being the number of genomic regions. A genomic region may be a chromosome, a chromosomal arm, or a portion of a chromosomal arm. The reference size pattern may similarly be a multi-dimensional vector (e.g., size N×M). The plurality of methylation levels may be compared to the reference size pattern using machine learning models or other techniques. The use of multi-dimensional vectors and methylation levels is described below (e.g., FIGS. 13, 14A, 14B, and 14C).

At block 810, method 800 may include determining a level of cancer based on the comparison. The level of cancer may include whether the subject has or does not have cancer, a likelihood of cancer, or a tumor size.

If the reference size pattern is determined from the plurality of reference samples from subjects with cancer and the comparison includes a determination of similar methylation levels or a similar shape, then the subject may be determined to have cancer. With this reference size pattern, if the comparison includes a determination of different methylation levels or a different shape, then the subject may be determined to not have cancer. If the reference size pattern is determined from a plurality of reference samples without cancer and the comparison includes a determination of different methylation levels or shape, then the subject may be determined to have cancer. And if the reference size pattern is determined from a plurality of reference samples without cancer and the comparison includes a determination of similar methylation levels or shape, then the subject may be determined to not have cancer.

E. Pattern Analysis with Size-Banded Matrix

With various cancers, certain genomic regions, including chromosomal arms, may be more likely to have copy number aberrations. Analyzing the size ranges by chromosomal arm for possible copy number aberrations may then be used to help determine a probability of cancer or detect cancer. Machine learning models can be used to determine a cancer classifier based on a pattern of size characteristics at different chromosomal regions (e.g., arms).

1. Size Pattern Analysis

Because the size profile of tumor-derived DNA in the plasma of cancer patients has been shown to be different from nontumor-derived DNA molecules, with the former generally comprising of more short DNA molecules (Jiang et al. *Proc. Natl. Acad. Sci.* 2015; 112:E1317-E1325), we reasoned that the size-band based approach described in this invention would be useful for detecting cancer-associated aberrations, such as copy number aberrations (CNA) and methylomic aberrations. As an example, we applied size-band based pattern recognition to 4 plasma DNA samples of early hepatocellular carcinoma (HCC) patients and 67 chronic hepatitis B (HBV) carriers without HCC cancers (HBV carriers). Thirty plasma DNA samples of healthy controls were used to build the normal reference range of copy number changes which was used to call the CNAs and methylomic aberrations in HCC patients and HBV carriers.

Figure 9:
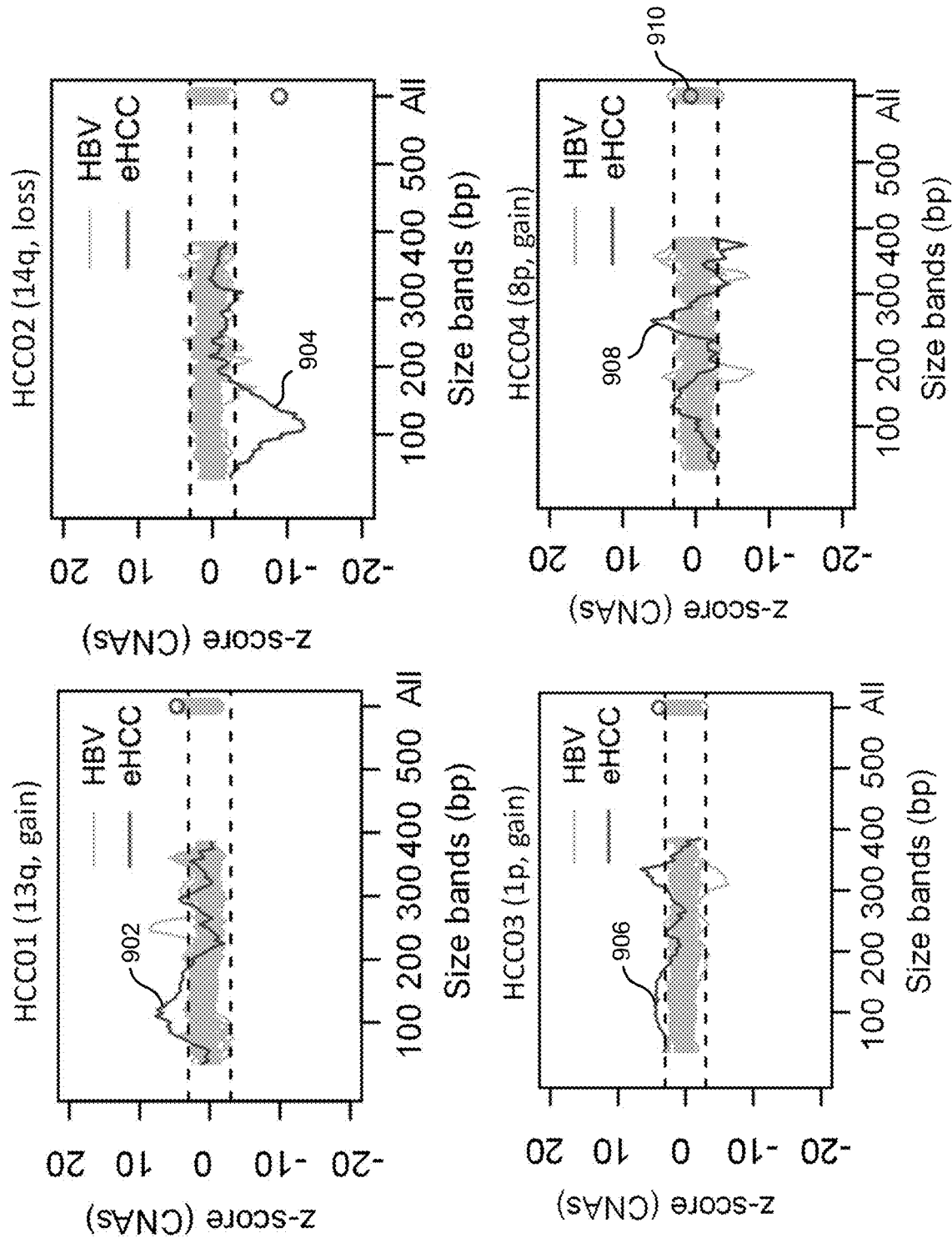
FIG. 9 shows size-band based changing patterns of the measured copy number aberrations in plasma DNA of hepatocellular carcinoma (HCC) patients according to embodiments of the present invention.

FIG. 9 shows size-band based changing patterns of the measured copy number aberrations in plasma DNA of hepatocellular carcinoma (HCC) patients. Red lines represented early HCC (eHCC) and gray lines represented the chronic hepatitis B virus (HBV) carriers without HCC. We observe that the curve (red or darker lines 902, 904, 906, and 908) of size-band patterns of measured CNAs in patients with HCC cancers were distinct from those curves (gray lines) for patients with HBV carriers. For example, HCC01 and HCC03 cases had copy gains on 13q and 1p chromosomal arms, respectively.

In HCC01 and HCC03, we could consistently detect the non-random wave-like size-band based patterns in which size bands with the mid-point at 210 bp tended to a turning point relative to its left and right sides showing copy number changes and the size-band patterns around 120 bp showed a tendency of "bell curve." For the HCC02 case that subjected to 14q deletions, an inverted "bell curve" were present. For the HCC04 case, if we used a z-score for all the fragments, we could not detect the cancer, as shown by circle 910 having a z-score below 3 and well within the range of z-scores for the non-cancer patients. However, if we utilized the size-band based approach, we could distinguish HCC04 from the non-cancer patients showing a random size-band based patterns (gray lines). In contrast, such non-random distinct size-band based patterns were not present in the control group. Different chromosomal arms show different size patterns. A size pattern may need to be referenced to a size pattern specific to a chromosomal arm.

2. Cancer Classifier with Size-Banded GR Matrix

Cancer cells generally bear the copy number aberrations that would occur in any chromosomal arms, which would be reflected in blood plasma when tumor cells shed DNA into the blood circulation of a cancer patient. Because the tumor-derived cell-free DNA molecules are shown to have distinct size properties in comparison to background normal cell-free DNA (e.g., tumor cell-free DNA molecules are shorter than background cell-free DNA derived from normal cells), the relative tumor DNA fraction across different size ranges would be varied. Thus, the measured degree of copy number aberrations across different size ranges present in plasma of a cancer patient would be a function of the relative tumor DNA fraction across different size ranges.

We proposed that to capture the detailed patterns of the measured copy number aberrations across different size ranges would improve the performance in differentiating cancer and non-cancer patients. The patterns can include multiple regions as well.

Figure 10:
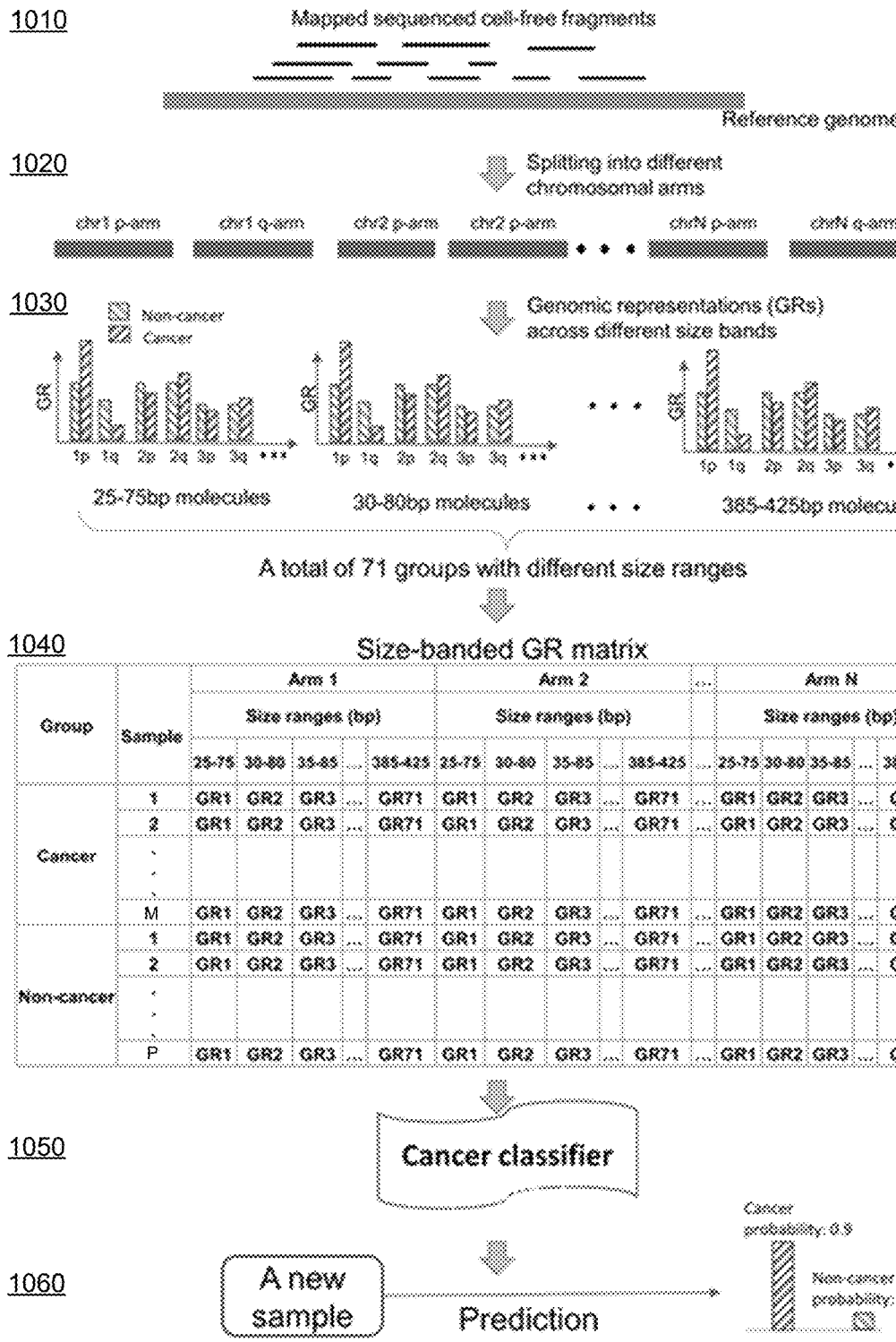
FIG. 10 illustrates a workflow for a size-banded genomic representation (GR) approach for cancer detection according to embodiments of the present invention.

FIG. 10 illustrates a workflow for a size-banded genomic representation (GR) approach for cancer detection according to embodiments of the present invention. At stage 1010, we mapped the sequenced cell-free DNA fragments to reference genome. At stage 1020, the sequenced fragments are mapped to different chromosomal arms.

At stage 1030, the sequenced fragments are further classified into different size ranges (size bands). For example, the size ranges may include, but are not limited to, 35-75 bp, 40-80 bp, 45-85 bp, 50-90 bp, 55-95 bp, 60-100 bp, 65-105 bp, 70-110 bp, 75-115 bp, 80-120 bp, 85-125 bp, 90-130 bp, 95-135 bp, 100-140 bp, 105-145 bp, 110-150 bp, 115-155 bp, 120-160 bp, 125-165 bp, 130-170 bp, 135-175 bp, 140-180 bp, 145-185 bp, 150-190 bp, 155-195 bp, 160-200 bp, 165-205 bp, 170-210 bp, 175-215 bp, 180-220 bp, 185-225 bp, 190-230 bp, 195-235 bp, 200-240 bp, 205-245 bp, 210-250 bp, 215-255 bp, 220-260 bp, 225-265 bp, 230-270 bp, 235-275 bp, 240-280 bp, 245-285 bp, 250-290 bp, 255-295 bp, 260-300 bp, 265-305 bp, 270-310 bp, 275-315 bp, 280-320 bp, 285-325 bp, 290-330 bp, 295-335 bp, 300-340 bp, 305-345 bp, 310-350 bp, 315-355 bp, 320-360 bp, 325-365 bp, 330-370 bp, 335-375 bp, 340-380 bp, 345-385 bp, 350-390 bp, 355-395 bp, 360-400 bp, 365-405 bp, 370-410 bp, 375-415 bp, 380-420 bp, and 385-425 bp. Such size ranges may be used for all other embodiments as well.

For a group of molecules within a particular size range, the proportion of sequenced fragments mapped to each chromosomal arm would be calculated, herein being referred to as genomic representation (GR). GR is the proportion of all the DNA fragments that correspond to a particular region (or entire genome) within the size range. Stage 1030 shows GR for different size ranges, for different chromosomal arms, for samples known to have cancer and for samples known to not have cancer.

As an example, if each chromosomal arm includes 71 size ranges and autosomes have a total of 39 chromosomal arms, then the size ranges and the chromosomal arms result in a 2,769-dimensional vector. Stage 1040 shows a table ("Size-banded GR matrix") that shows possible multidimensional vectors. First row 1042 corresponds to Cancer Sample 1 and shows a 71×N dimensional vector, where N is the number of chromosomal arms. The table shows M samples for cancer and P samples for non-cancer.

At stage 1050, the multi-dimensional vectors and a size-banded GR matrix formed from the multi-dimensional vectors can be used to train a cancer classification model. The machine learning algorithms or deep learning algorithms could be used for training the cancer classifier, including but not limited to support vector machines (SVM), decision tree, naive Bayes classification, logistic regression, clustering algorithm, principal component analysis (PCA), singular value decomposition (SVD), t-distributed stochastic neighbor embedding (tSNE), artificial neural network, as well as ensemble methods which construct a set of classifiers and then classify new data points by taking a weighted vote of their predictions. Once the cancer classifier is trained, the probability of cancer for a new patient can be predicted.

The training data can include cancer and non-cancer subjects. Machine learning algorithms modeling the cell-free DNA measurements (size-banded GR, methylation, and so on) can be used to construct a classifying boundary (e.g., using a set of trained weights and coefficients organized in linear or non-linear formula, such as logistic regression formula) which give a best separation between cancer and non-cancer subjects. The deviation of an input vector of a new sample including the cell-free DNA measurements from an optimal classifying boundary toward cancer-associated data points would indicate the likelihood of being cancer. Such deviation could be normalized or translated into probability of cancer within a scale of from 0 to 1. The higher the probability, the higher likelihood of being cancer. The probability of cancer above a certain threshold (e.g. >0.6) can be considered as a positive test with cancer.

For hepatocellular carcinoma, it was reported that 1p, 1q, 8p, and 8q were commonly aberrant in terms of copy numbers (Proc Natl Acad Sci USA. 2015 Mar. 17; 112(11): E1317-25). Thus, to illustrate the performance of size-banded cancer detection, we used massively parallel sequencing platform to sequence a number of healthy controls (CTR), HBV carriers (HBV), cirrhotic subjects (cirrhosis), early-stage HCC (eHCC), intermediate-stage HCC (iHCC), and advanced-stage HCC (aHCC). For the training dataset, we sequenced a limited number of advanced stage HCC patients, and then artificially admixed the sequencing results of advanced-stage HCC patients with those of non-HCC subjects to form the training dataset containing enough HCC positive patients with the wide coverage of tumor DNA fractions ranged from 0.01% and 50% and non-HCC subjects. To this end, 401 HCC patients were created by randomly repeatedly mixing 34 HBV, 10 CTR and 9 aHCC subjects by varying the proportion of sequencing reads being used, and 175 non-HCC patients were created by randomly repeatedly mixing 34 HBV, 15 Cirrhosis, and 10 CTR subjects. SVM algorithm was used to train the cancer classifier using such 401 HCC patients and 175 in-HCC patients.

At stage 1060, the trained cancer classification model can be used to predict whether a new sample has cancer or does not have cancer. A probability of cancer may be determined by the model, with a probability above the threshold considered as a positive test for cancer.

The size-banded approach for detecting cancer and the conventional z-score approach were applied to a testing dataset including 30 CTR, 19 HBV, 14 cirrhosis, 36 eHCC, and 11 iHCC subjects.

Figure 11A:
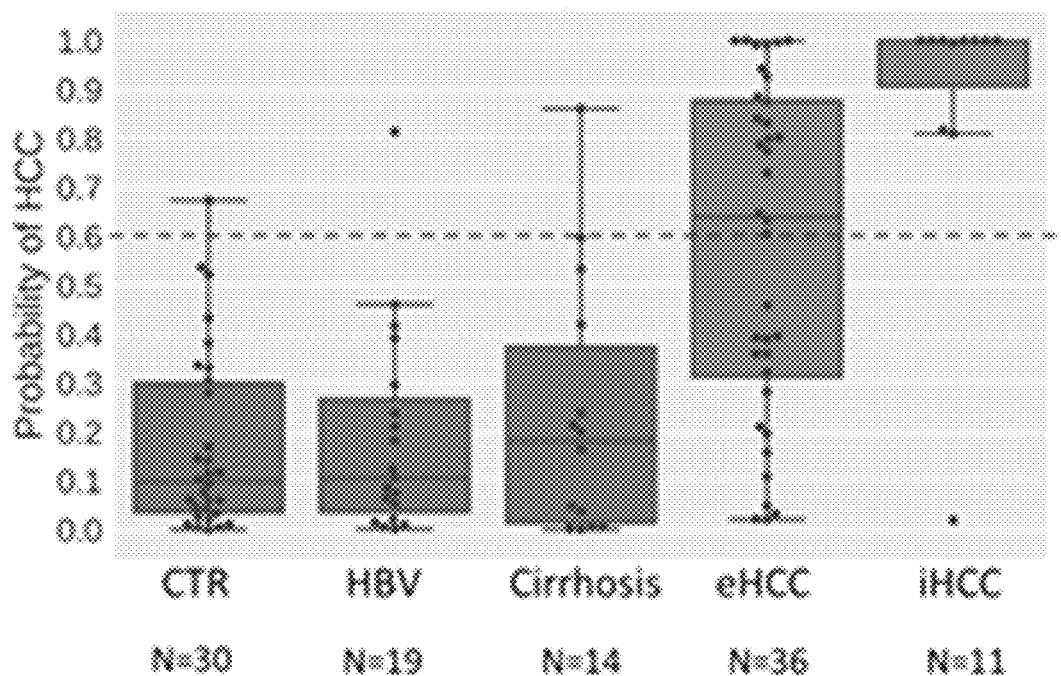
FIGS. 11A, 11B, and 11C show a comparison between size-banded GR and conventional z-score approaches according to embodiments of the present invention.

FIG. 11A shows the results of the size-banded approach for detecting cancer. SVM was used to train the cancer classifier. Both eHCC and iHCC subjects had median values above a 0.60 probability of cancer, with iHCC having a higher probability than eHCC. CTR, HBV, and cirrhosis subjects showed median probabilities below 0.20. The size-banded approach for detecting cancer had 64% sensitivity at the specificity of 95%. The dotted red line corresponds to 95% specificity.

Figure 11B:
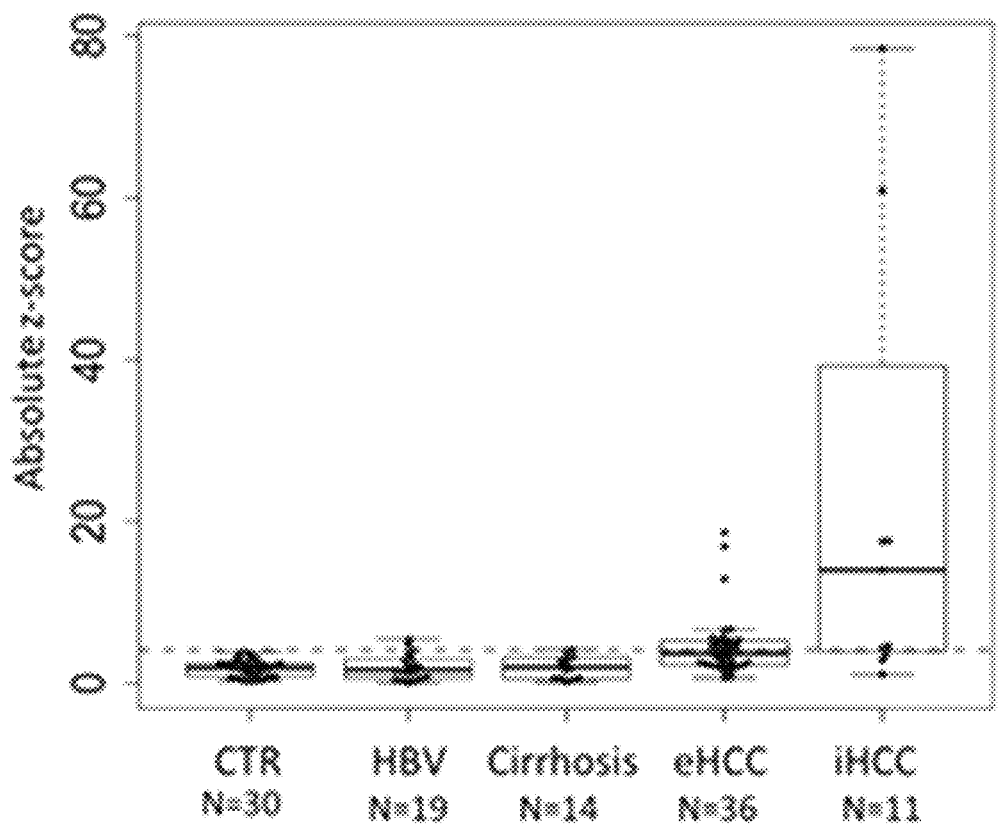

FIG. 11B shows the results of the conventional z-score approach for detecting cancer. The dotted red line corresponds to 95% specificity, which was at a z-score around 4.2. Chromosomal arms 1p, 1q, 8p, and 8q were used as examples. The GR for each arm of a test sample was calculated. The corresponding mean and standard deviation was also calculated. Each arm z-score would be calculated as (GR−mean)/standard deviation. The absolute z-score equaled the sum of the four absolute z-scores corresponding to the four chromosomal arms. The iHCC subjects had a median absolute z-score of cancer noticeably higher than CTR, HBV, cirrhosis, and eHCC subjects. While the median absolute z-score for iHCC was higher than absolute z-scores for the other subjects, the z-scores of several iHCC subjects were fairly similar to the other subjects. However, the median absolute z-score for eHCC was only slightly higher than those of CTR, HBV, and cirrhosis subjects and was about the same as a z-score threshold level of 3. The conventional z-score approach had 51% sensitivity at the specificity of 95%. Thus, the size-banded approach shows superior sensitivity over the conventional z-score approach.

Figure 11C:
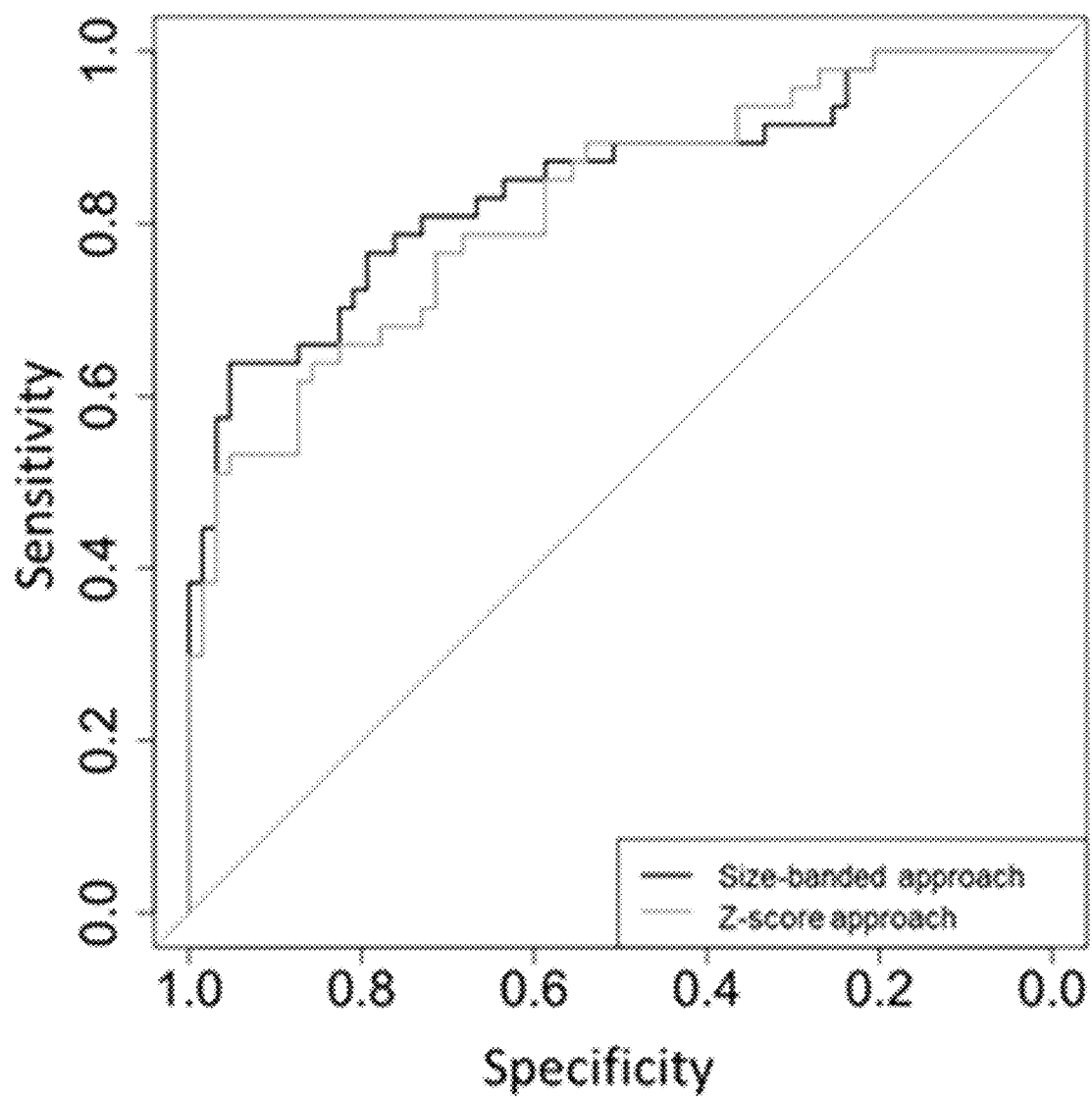
Figure 12:
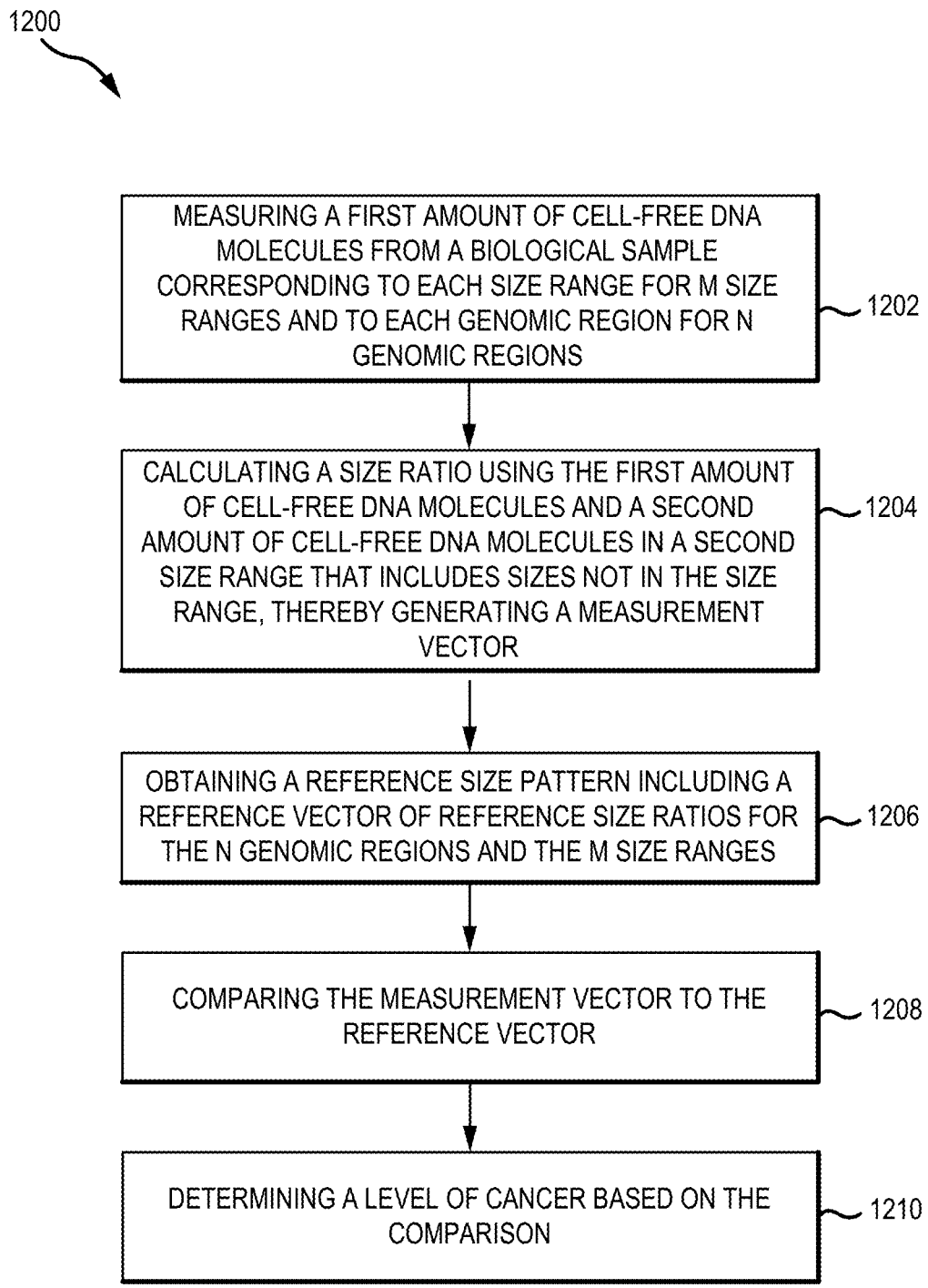
FIG. 12 shows a method of determining a cancer classification according to embodiments of the present invention.

FIG. 11C shows the superiority of the size-banded approach over the conventional z-score approach with a receiver operating characteristic curve (ROC) analysis (0.84 vs. 0.82). 3. Example method with size-banded genomic representation (GR) matrix FIG. 12 shows an example method 1200 of determining a cancer classification in a biological sample from a subject. The biological sample may include a mixture of cell-free DNA molecules including tumor DNA molecules and non-tumor DNA molecules.

At block 1202, a first amount of cell-free DNA molecules from a biological sample may be measured. The first amount of cell-free DNA molecules may correspond to each size range for M ranges and to each genomic region for N genomic regions. The plurality of size ranges may be determined as described with method 600 or method 800. Each genomic region may be a chromosomal arm.

At block 1204, a size ratio may be calculated using the first amount of cell-free DNA molecules and a second amount of cell-free DNA molecules in a second size range that includes sizes not in the size range. The size ratio may be calculated as in method 600, but the size ratio may be for a particular genomic region (e.g., chromosomal arm). As an example, the size ratio may be any of genomic representations GR1, GR2, GR3, . . . GR 71 in row 1004 in FIG. 10. Calculating the size ratio may generate a measurement vector of N×M size ratios. N may be an integer greater than equal to 1. N and M may be integers greater than 1, including greater than 2, 3, 4, 5, or 6.

At block 1206, a reference size pattern may be obtained. The reference size pattern may include a reference vector of reference size ratios for the N genomic regions and the M size ranges. The reference size pattern may be determined from a plurality of reference samples from subjects with cancer or from subjects without cancer. The reference size pattern may be determined using a machine learning model.

The machine learning model may be determined using a training set of size ratios including size ratios at each of the plurality of genomic regions from an individual having cancer. The cancer classifier may be determined using a machine learning algorithm or deep learning algorithm. The machine learning model or deep learning algorithm may include support vector machines (SVM), decision tree, naive Bayes classification, logistic regression, clustering algorithm, principal component analysis (PCA), singular value decomposition (SVD), t-distributed stochastic neighbor embedding (tSNE), artificial neural network, or any algorithm described herein. The training set may include size ratios at different genomic regions for individuals determined to have cancer and for individuals determined not to have cancer. The machine learning model may be the cancer classifier in FIG. 10.

At block 1208, the measurement vector may be compared to the reference vector. The comparison may be compared using a machine learning model. The comparison may result in a value based on the similarity of the measurement vector to the reference vector.

Comparing the measurement vector to the reference vector may include comparing the N×M size ratios to a plurality of threshold values that are determined from the plurality of reference samples. For example, each size range may have a different threshold value, which may be based on a standard deviation for reference samples. Accordingly, there may be N×M threshold values. A single size range may also have different threshold values, with each threshold value associated with a different certainty level that the size ratio is different from the reference samples. Comparing may include counting the number of threshold values exceeded and determining the level of cancer based on the comparison. A higher level of threshold values exceeded may indicate a larger difference between the measurement vector and the reference vector.

At block 1210, a level of cancer may be determined based on the comparison. The cancer may include hepatocellular carcinoma. The cancer may include colorectal cancers, lung cancers, nasopharyngeal cancers, ovarian cancers, stomach cancers, and blood cancers. Method 1200 may allow for differentiation between cancers and non-cancer subjects. The subject may be classified as having cancer or having a high likelihood of cancer based on the value based on the similarity of the measurement vector to the reference vector. The value based on the similarity may be compared to the cutoff value. A value based on the similarity that more greatly exceeds the cutoff value may indicate a higher likelihood or severity of cancer. The method may further comprising treating cancer when the subject is classified as having cancer or having a high likelihood of cancer.

Method 1200 may be adapted to determine a level of an autoimmune disorder instead of cancer. An autoimmune disorder may include systemic lupus erythematosus (SLE). The sizes DNA fragments have been found to be related to SLE, as described in US Patent Publication No. 2015/0087529 A1, filed Sep. 19, 2014, the contents of which are incorporated herein by reference for all purposes. A level of the autoimmune disorder may be determined by comparing measurement vectors to a reference vector. The reference vector may be from a reference size pattern. The reference size pattern may be determined from samples from healthy subjects or subjects with known levels of the autoimmune disorder. Method 1200 may allow for differentiation between subjects with and without autoimmune disorders.

4. Cancer Classifier with Size-Banded Methylation Density (MD) Matrix

Cancer cells generally bear the specific methylation patterns which would occur in any genomic regions. For example, in cancer cells, Alu repeat regions may be preferentially less methylated compared with non-malignant cells, and CpG island regions may be preferentially more methylated compared with non-malignant cells. Such cancer-associated aberrant methylation signals can be reflected in blood plasma of cancer patients when tumor cells shed DNA into the blood circulation. As explained above, the relative tumor DNA fraction across different size ranges varies. Thus, the measured degree of cancer-associated methylation levels across different size ranges present in plasma of a cancer patient would be a function of the relative tumor DNA fraction across different size ranges.

We proposed that to capture the detailed patterns of the measured methylation aberrations across different size ranges would improve the performance in differentiating cancer and non-cancer patients.

Figure 13:
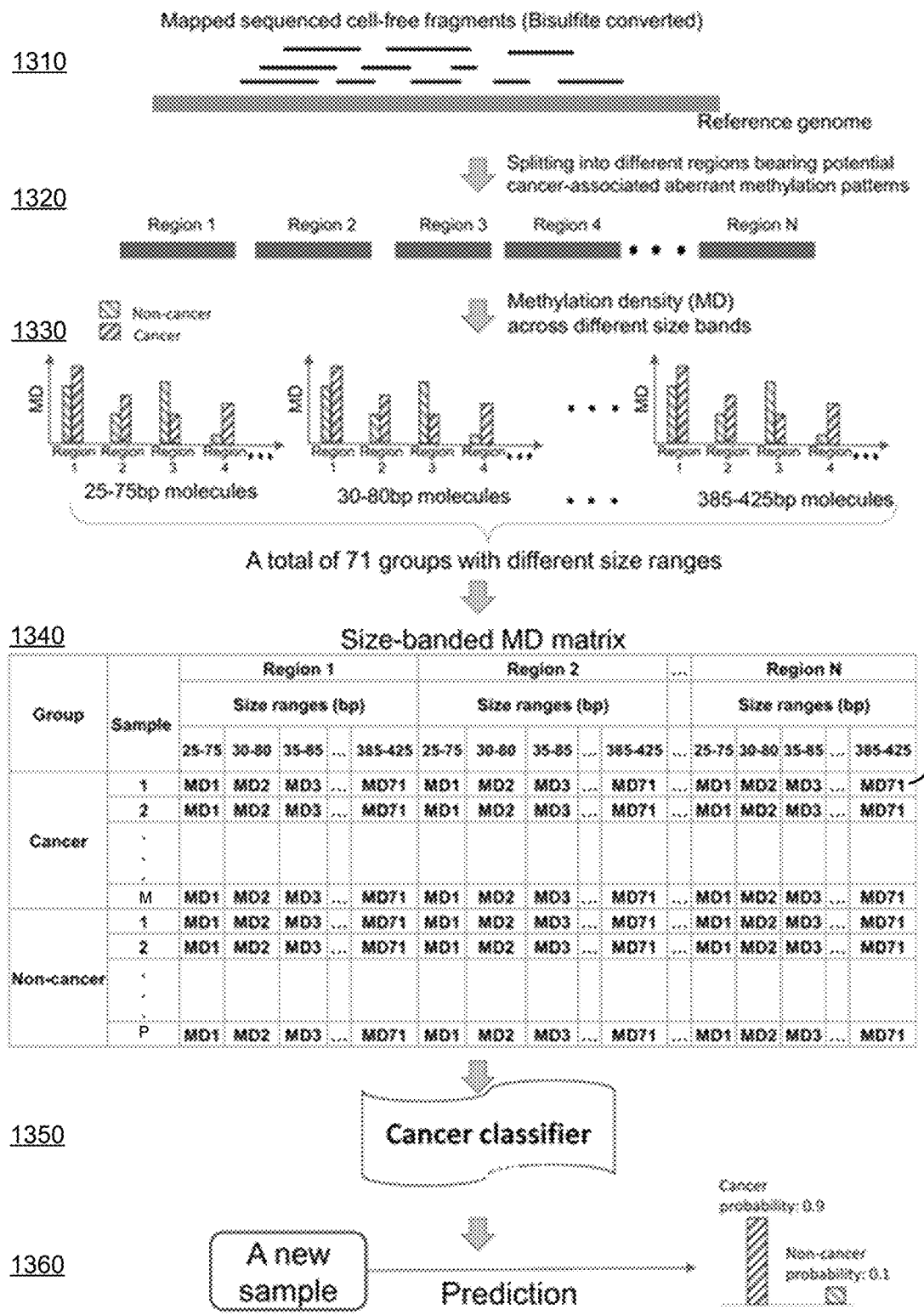
FIG. 13 illustrates a workflow for a size-banded methylation density (MD) approach for cancer detection according to embodiments of the present invention.

FIG. 13 illustrates a workflow for a size-banded methylation density (MD) approach for cancer detection according to embodiments of the present invention. At stage 1310, we mapped the sequenced bisulfite-converted cell-free DNA fragments to a reference genome using Methy-Pipe (Jiang et al., PLoS One. 2014; 9(6):e100360) or other methylation-aware aligners. At stage 1320, the sequenced fragments mapped to different differentially methylated regions are located.

At stage 1330, the sequenced fragments are further classified into different size ranges (size bands). For example, the size ranges may include any size ranges described herein, including those size ranges described in stage 1030 for FIG. 10.

For a group of molecules within a particular size range, the proportion of sequenced CpG on a region of interest (e.g., Alu repeat or CpG islands) would be calculated, resulting in the methylation density (MD). which reflects the methylation level. Regions may show different methylation levels between liver cancer cells and other normal cells, including hematopoietic cells (e.g. T cells, B cells, neutrophils, macrophages, erythroblast cells, and so on), liver cells, and colon cells. Stage 1330 shows MD for different size ranges, for different genomic regions, and for samples known to have cancer and for samples known to not have cancer.

As an example, if each region includes 71 size ranges and there are a total of 32,450 regions showing differentially methylated in between liver cancer cells and other normal cells, then the size ranges and the genomic regions result in a 2,303,950-dimensional vector. Stage 1340 shows a table ("Size-banded MD matrix") that shows possible multidimensional vectors. First row 1342 of the table corresponds to Cancer Sample 1 shows a 71×N dimensional vector, where N is the number of genomic regions. The table shows M samples for cancer and P samples for non-cancer.

At stage 1350, the multi-dimensional vectors and a size-banded MD matrix formed from the multi-dimensional vectors can be used to train a cancer classification model. Training can be by any suitable machine learning model that performs a classification, e.g., as described herein, including for stage 1050 of FIG. 10. Once the cancer classifier is trained, the probability of a sample indicating cancer for a new patient can be predicted. The probability of cancer being above a certain threshold (e.g. >0.6) can be considered as a positive test with cancer.

To illustrate the performance of cancer detection with the use of size-banded methylation levels, we used massively parallel sequencing platform to sequence a number of healthy controls (CTR), HBV carriers (HBV), cirrhotic subjects (cirrhosis), early-stage HCC (eHCC), intermediate-stage HCC (iHCC), and advanced-stage HCC (aHCC). For the training dataset, we sequenced a limited number of advanced stage HCC patients, and then artificially admixed the sequencing results of advanced-stage HCC patients with those of non-HCC subjects to form the training dataset containing enough HCC positive patients with the wide coverage of tumor DNA fractions ranged from 0.01% and 50% and non-HCC subjects. To this end, 140 HCC patients were created by randomly repeatedly mixing 27 HBV and 7 aHCC subjects by varying the proportion of sequencing reads being used, and 140 non-HCC patients was created by randomly repeatedly mixing 7 HBV and 20 CTR subjects. SVM algorithm was used to train the cancer classifier using such 140 HCC patients and 140 non-HCC patients.

At stage 1360, the trained cancer classification model can be used to predict whether a new sample has cancer or does not have cancer. A probability of cancer may be determined by the model, with a probability above the threshold considered as a positive test for cancer.

Figure 14A:
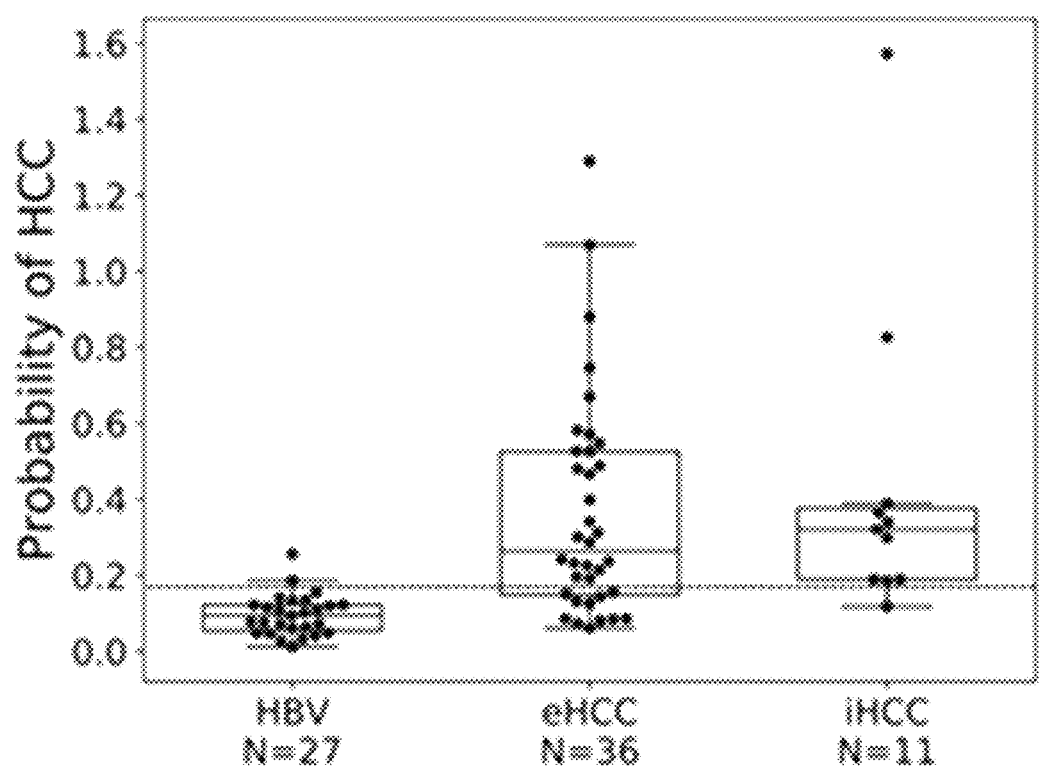
FIGS. 14A, 14B, and 14C show a comparison between size-banded MD and conventional z-score approaches according to embodiments of the present invention.
Figure 14B:
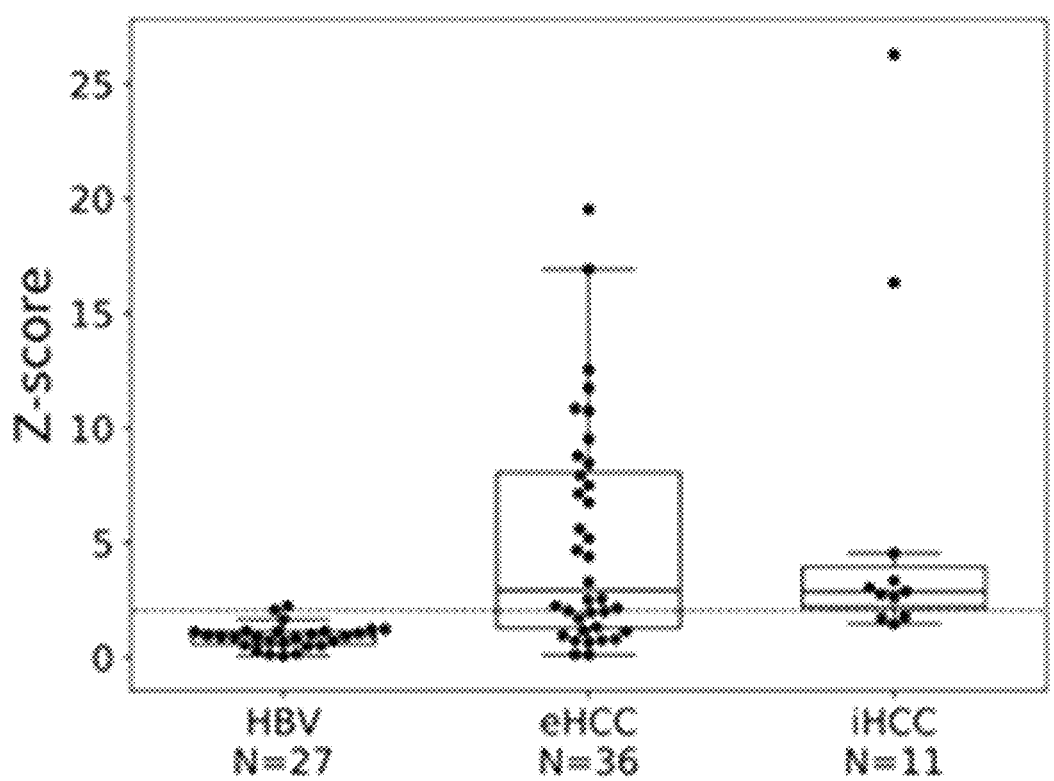
Figure 14C:
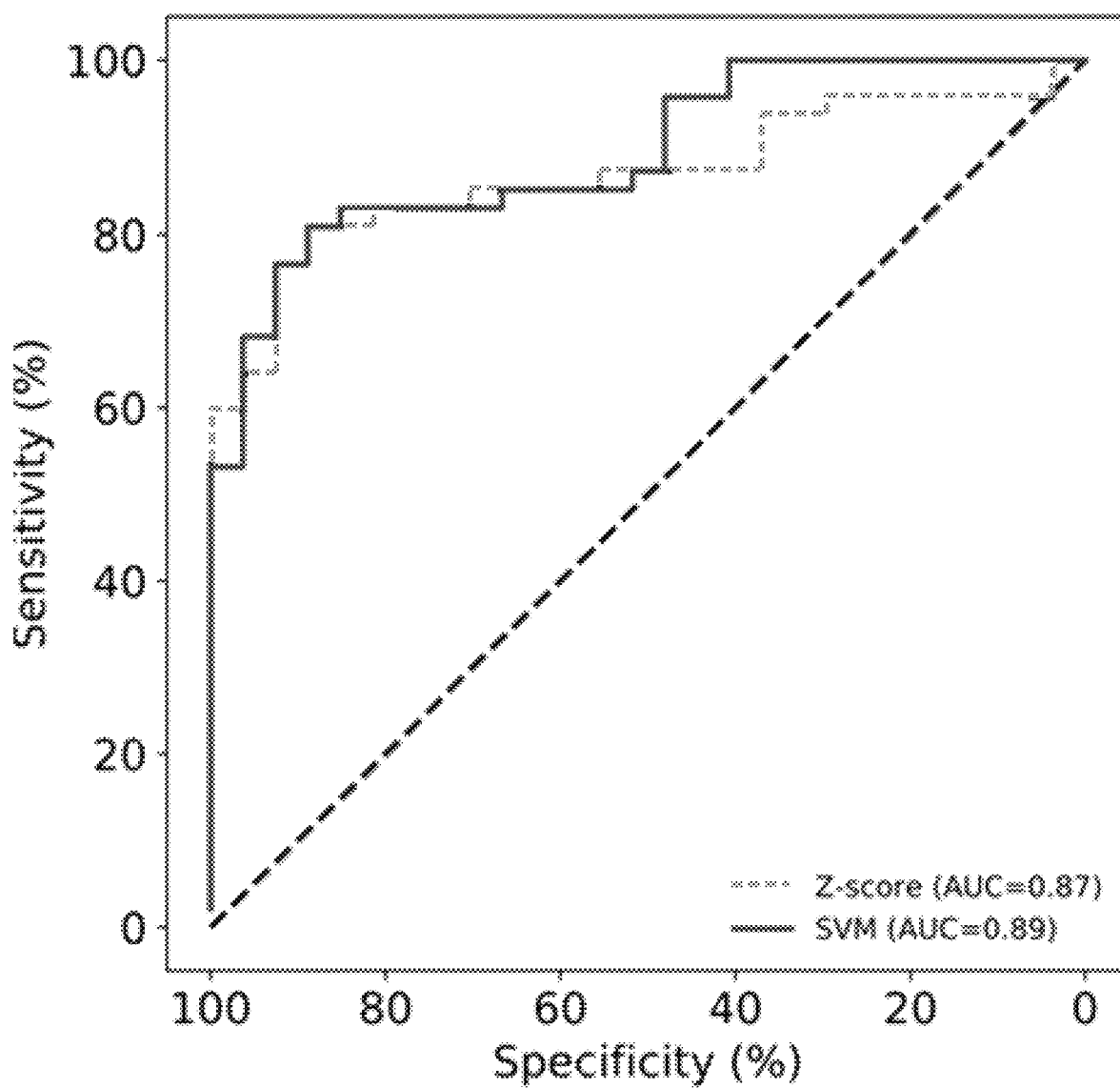

FIGS. 14A, 14B, and 14C show a comparison between size-banded MD and conventional z-score approaches according to embodiments of the present invention. FIG. 14A shows results for the size-banded MD approach. FIG. 14B shows results for the conventional z-score approach.

FIGS. 14A and 14B show that in a testing dataset including 27 HBV, 36 eHCC, and 11 iHCC subjects, the size-banded methylation approach for detecting cancer was superior to the conventional z-score approach. The conventional z-score approach was conducted in the following way: (1) the pooled methylation level (denoted by "X") for total fragments derived from all regions of interest are calculated; (2) the mean of the pooled methylation levels (M), and the standard deviation of the pooled methylation levels (SD) in a non-cancer group are calculated; (3) then the conventional methylation z-score is defined by: z-score=(X−M)/SD. SVM was used to train the cancer classifier. The size-banded methylation approach in FIG. 14A had a 74.5% sensitivity at the specificity of 92.5%. By contrast, the conventional z-score approach in FIG. 14B had lower sensitivity, 65.9% sensitivity at the specificity of 92.5%. The increased sensitivity may lead to important benefits. Early detection of early cancers is generally associated with better treatment outcomes. Both the eHCC and iHCC groups are considered to be treatable stages. Therefore, any increase in sensitivity in the treatable cases has a clinical impact and may translate to very different survival profiles for the patients.

FIG. 14C shows the superiority of size-banded methylation approach in the receiver operating characteristic curve (ROC) analysis (SVM: 0.89 AUC vs. z-score: 0.87 AUC).

Accordingly, the use of multi-dimensional vectors with genomic representation (GR) (e.g., FIGS. 10-12) can be adapted for analysis using methylation densities in place of GR.

F. Additional Size Pattern Applications

Size-band based patterns would inform the origin for those aberrations seen in plasma DNA. As an example, in a pregnancy context, if the copy number aberrations derived from the mother, the size-band patterns would occur in a reverse direction compared with those originating from the fetus because maternal DNA fragments are longer than fetal DNA (Yu et al. *Clin. Chem.* 2017; 63:495-502). Size-band based molecular diagnostics could also be applied to the analysis of cell-free DNA in other clinical conditions, such as cancer (Jiang et al. *Proc. Natl. Acad. Sci.* 2015; 112: E1317-E1325), including enhancing the detection of point mutations, sub-chromosomal aberrations and epigenetic abnormalities. A clinical condition may include determining the presence of an immuno-response to a transplanted tissue or organ.

Besides, it would also allow us to distinguish the plasma DNA confounding aberrations present in plasma DNA such as systemic lupus erythematosus (SLE) because the apparent copy number changes present in plasma DNA of SLE patients (Chan et al. *Proc. Natl. Acad. Sci.* 2014; 111:E5302-E5311) would be likely due to preferential binding of anti-DNA antibody to particular DNA sequences rather than a true copy number changes in particular cells. Thus, size-band based analysis would be expected to see random shape changes in relation to different size bands for measured copy number aberrations present in plasma of SLE patients.

Embodiments may include treating the disease or condition in the patient after determining the level or probability of the disease or condition in the patient. Treatment may include any suitable therapy, drug, or surgery, including any treatment described in a reference mentioned herein. Information on treatments in the references are incorporated herein by reference.

II. Materials and Methods

Sample Collection and Processing

The anonymized data analyzed for this retrospective study were obtained from existing patient data in the University Pathology Service (UPS) of The Chinese University of Hong Kong. Patient data consisting of 161 samples were generated as a result of the UPS laboratory-developed test. Anonymized patients with HCC admitted to the Department of Surgery of the Prince Wales Hospital, Hong Kong, for tumor resection were recruited. All blood was collected before surgery. Anonymized HBV carriers and cirrhosis subjects were recruited from the Department of Medicine and Therapeutics of the Prince of Wales Hospital, Hong Kong. The samples were obtained by centrifuging blood to obtain plasma. Briefly, peripheral blood samples were collected into EDTA-containing tubes, which were subsequently centrifuged at 1,600 g for 10 min at 4° C. The plasma portion was recentrifugated at 16,000 g for 10 min at 4° C. to obtain cell-free plasma that were stored at −80° C. until further analysis. DNA was extracted from 4-10 mL of plasma using the QIAamp DSP DNA Blood Mini Kit (Qiagen). The plasma DNA was concentrated with a Speed-Vac Concentrator (Savant DNA120; Thermo Scientific) into a 75-µL final volume per sample.

Sequencing Library Preparation and DNA Sequencing

Using the extracted plasma DNA, indexed DNA libraries were constructed with the Paired-end Sequencing Sample Preparation Kit according to the manufacturer's instructions. In this step, plasma double-stranded DNA molecules would be end-repaired to form the blunt ends and simultaneously were added an extra A base. The adaptors, which can aid PCR amplification, be annealed to flowcell, and facilitate sequencing, were ligated to A-tagged double-stranded plasma DNA molecules to form the sequencing library. The library can be sequenced in a paired-end mode with the use of 36 or 50 or 75 cycles for each end as previously described (Yu et al. *Proc. Natl. Acad. Sci. U.S.A.* 2014; 111:8583-8).

Sequence Alignment

Sequences from each samples were aligned to the human reference genome (hg19) using the Short Oligonucleotide Alignment Program 2 (SOAP2) (Li et al. *Bioinformatics* 2009; 25:1966-1967) as previously described (Yu et al. *Proc. Natl. Acad. Sci. U.S.A.* 2014; 111:8583-8). On average, each sample obtained 12 million uniquely mapped paired-end reads (range: 10-15 million).

Methylation Levels

The methylation status of sites of the sequence read can be obtained as described herein. For example, the DNA molecules can be analyzed using sequence reads of the DNA molecules, where the sequencing is methylation-aware. For example, methylation-aware sequencing can include, but not limited to bisulfite sequencing, or sequencing preceded by methylation-sensitive restriction enzyme digestion, immunoprecipitation using anti-methylcytosine antibody or methylation binding protein, or single molecule sequencing that allows elucidation of the methylation status. Other methylation-aware assays can also be used.

The sequence reads can each include a methylation status of cell-free DNA molecules from the biological sample. The methylation status can include whether a particular cytosine residue is 5-methylcytosine or 5-hydroxymethylcytosine. The sequence reads can be obtained in various ways, each as various sequencing techniques, PCR techniques (e.g., real-time or digital), arrays, and other suitable techniques for identifying sequences of fragments. Real-time PCR is an example of analyzing a group of DNA collectively, e.g., as an intensity signal proportional to the number of DNA methylated at a site. A sequence read can cover more than one site depending on the proximity of the two sites to each other and the length of the sequence read.

The analysis can be performed by receiving sequence reads from a methylation-aware sequencing, and thus the analysis can be performed just on data previously obtained from the DNA. In other embodiments, the analysis can include the actual sequencing or other active steps for performing the measurements of the properties of the DNA molecules. The sequencing may be performed in a variety of ways, e.g., using massively parallel sequencing or next-generation sequencing, using single molecule sequencing, and/or using double- or single-stranded DNA sequencing library preparation protocols, and other techniques described herein. As part of the sequencing, it is possible that some of the sequence reads may correspond to cellular nucleic acids.

The sequencing may be targeted sequencing, e.g., as described herein. For example, biological sample can be enriched for nucleic acid molecules from the virus. The enriching of the biological sample for nucleic acid molecules from the virus can include using capture probes that bind to a portion of, or an entire genome of, the virus. Other embodiments can use primers specific to a particular locus of the virus. The biological sample can be enriched for nucleic acid molecules from a portion of a human genome, e.g., regions of autosomes. FIG. 1 provides examples of such capture probes. In other embodiments, the sequencing can include random sequencing.

After sequencing by a sequencing device, the sequence reads may be received by a computer system, which may be communicably coupled to a sequencing device that performed the sequencing, e.g., via wired or wireless communications or via a detachable memory device. In some embodiments, one or more sequence reads that include both ends of the nucleic acid fragment can be received. The location of a DNA molecule can be determined by mapping (aligning) the one or more sequence reads of the DNA molecule to respective parts of the human genome, e.g., to specific regions, such as differentially methylation regions (DMRs). In one implementation, if a read does not map to a region of interest, then the read can be ignored. In other embodiments, a particular probe (e.g., following PCR or other amplification) can indicate a location, such as via a particular fluorescent color. The identification can be that the cell-free DNA molecule corresponds to one of the set of one or more sites, i.e., the particular site may not be known, as the amount of DNA methylated at one or more sites is all that is needed.

After sequencing and alignment, the methylation status of an individual CpG site could thus be inferred from the count of methylated sequence reads "M" (methylated) and the count of unmethylated sequence reads "U" (unmethylated) at the cytosine residue in CpG context. Using the bisulfite sequencing data, the entire methylomes of maternal blood, placenta and maternal plasma were constructed. The mean methylated CpG density (also called methylation density MD) of specific loci in the maternal plasma can be calculated using the equation:

$$MD = \frac{M}{M+U}$$

where M is the count of methylated reads and U is the count of unmethylated reads at the CpG sites within the genetic locus. If there is more than one CpG site within a locus, then M and U correspond to the counts across the sites.

As an alternative, a methylation assay can be performed on bisulfite-converted genomic DNA according to an Infinium HD Methylation Assay protocol. The hybridized beadchip can be scanned on an Illumina iScan instrument. DNA methylation data were analyzed by the GenomeStudio (v2011.1) Methylation Module (v1.9.0) software, with normalization to internal controls and background subtraction. The methylation index for individual CpG site can be represented by a beta value (p), which may be calculated using the ratio of fluorescent intensities between methylated and unmethylated alleles:

$$\beta = \frac{\text{Intensity of methylated allele}}{\text{Intensity of unmethylated allele} + \text{Intensity of methylated allele} + \text{Intensity of methylated allele} + 100}$$

Calculation of Fetal DNA Fractions

In pregnancies carrying a male fetus, the fetal DNA fraction (f) in a maternal plasma sample can be determined from the proportion of reads aligned to chromosome Y (% chrY). In a previous study, it was shown that a small number of sequences in the plasma of pregnant women carrying a female fetus were wrongly aligned to chromosome Y (Chiu et al. *Proc Natl Acad Sci USA* 2008; 105:20458-20463). Therefore, the % chrY in the plasma of pregnant women carrying a male fetus was a mixture of the chromosome Y reads derived from the male fetus and the maternal reads that were misaligned to chromosome Y (Chiu et al. *BMJ* 2011; 342:c7401). The relationship between % chrY and f in pregnancies carrying a male fetus can be expressed using the following equation:

$$\% \text{chr}Y = \% \text{chr}Y_{male} \times f - \% \text{chr}Y_{female} \times (1-f)$$

where % chrY$_{male}$ is the proportion of reads aligned chromosome Y in a plasma sample containing 100% male DNA, and % chrY$_{female}$ is the proportion of reads aligned to chromosome Y in a plasma sample containing 100% female DNA.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

IV. Example Systems

Figure 15:
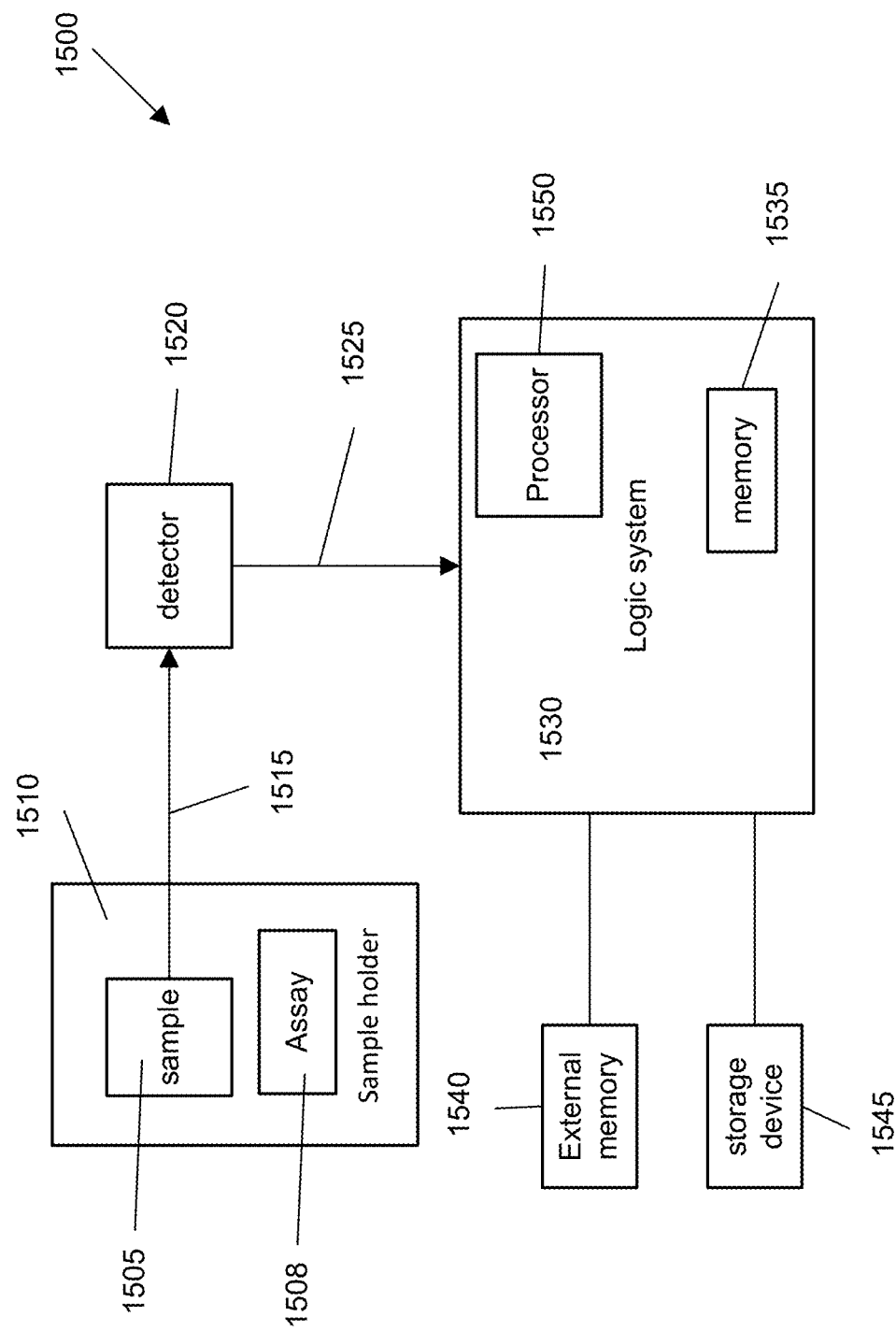
FIG. 15 illustrates a system according to embodiments of the present invention.

FIG. 15 illustrates a system 1500 according to an embodiment of the present invention. The system as shown includes a sample 1505, such as cell-free DNA molecules within a sample holder 1510, where sample 1505 can be contacted with an assay 1508 to provide a signal of a physical characteristic 1515. An example of a sample holder can be a flow cell that includes probes and/or primers of an assay or a tube through which a droplet moves (with the droplet including the assay). Physical characteristic 1515, such as a fluorescence intensity value, from the sample is detected by detector 1520. Detector can take a measurement at intervals (e.g., periodic intervals) to obtain data points that make up a data signal. In one embodiment, an analog to digital converter converts an analog signal from the detector into digital form at a plurality of times. Sample holder 1510 and detector 1520 can form an assay device, e.g., a sequencing device that performs sequencing according to embodiments described herein. A data signal 1525 is sent from detector 1520 to logic system 1530. Data signal 1525 may be stored in a local memory 1535, an external memory 1540, or a storage device 1545.

Logic system 1530 may be, or may include, a computer system, ASIC, microprocessor, etc. It may also include or be coupled with a display (e.g., monitor, LED display, etc.) and a user input device (e.g., mouse, keyboard, buttons, etc.). Logic system 1530 and the other components may be part of a stand-alone or network connected computer system, or they may be directly attached to or incorporated in a device (e.g., a sequencing device) that includes detector 1520 and/or sample holder 1510. Logic system 1530 may also include software that executes in a processor 1550. Logic system 1530 may include a computer readable medium storing instructions for controlling system 1500 to perform any of the methods described herein. For example, logic system 1530 can provide commands to a system that includes sample holder 1510 such that sequencing or other physical operations are performed. Such physical operations can be performed in a particular order, e.g., with reagents being added and removed in a particular order. Such physical operations may be performed by a robotics system, e.g., including a robotic arm, as may be used to obtain a sample and perform an assay.

Figure 16:
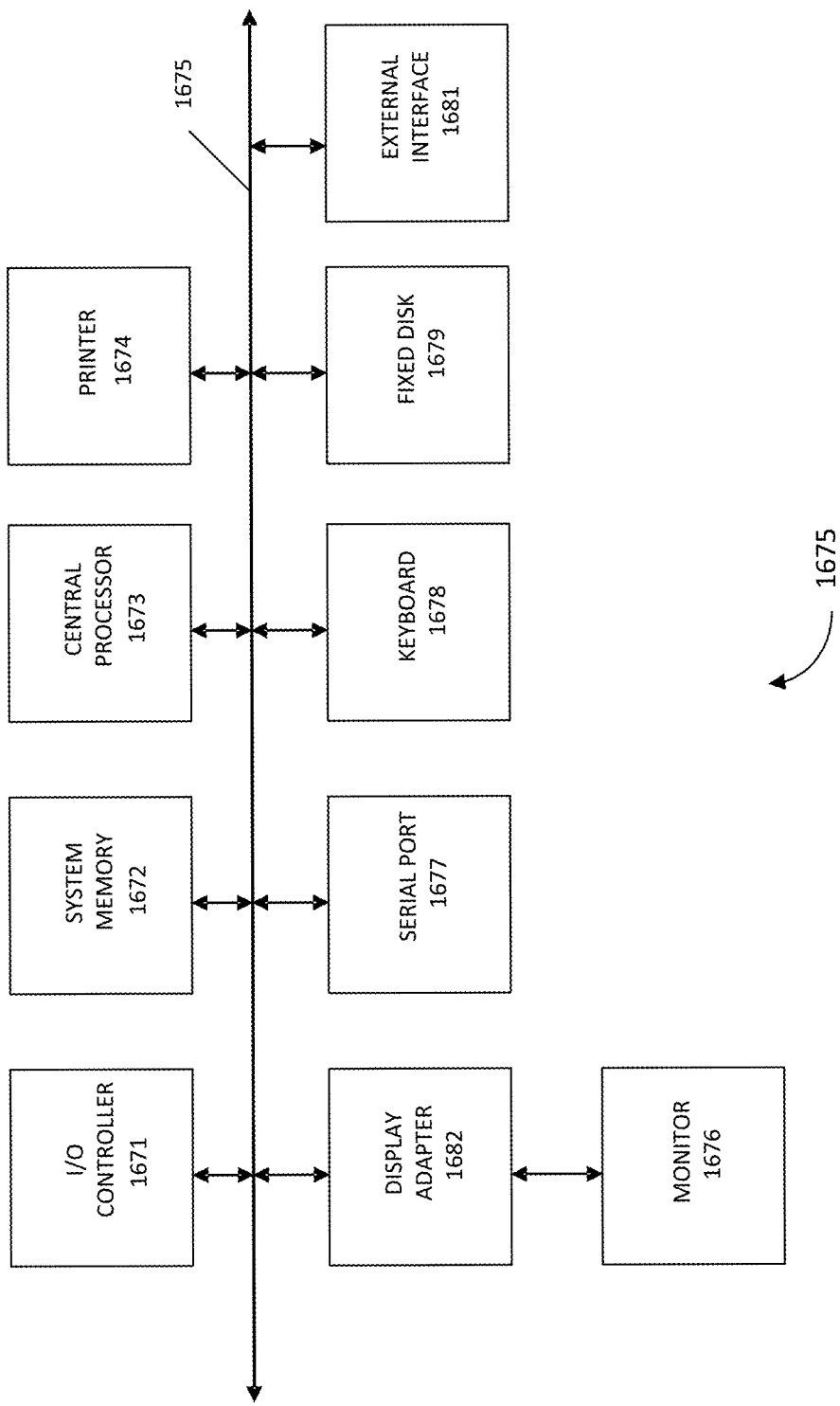
FIG. 16 shows a computer system according to embodiments of the present invention.

Any of the computer systems mentioned herein may utilize any suitable number of subsystems. Examples of such subsystems are shown in FIG. 16 in computer apparatus 1600. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 16 are interconnected via a system bus 1675. Additional subsystems such as a printer 1674, keyboard 1678, fixed disk 1679, monitor 1676, which is coupled to display adapter 1682, and others are shown. Peripherals and input/output (I/O) devices, which couple to I/O controller 1671, can be connected to the computer system by any number of means known in the art, such as serial port 1677. For example, serial port 1677 or external interface 1681 (e.g. Ethernet, Wi-Fi, etc.) can be used to connect computer apparatus 1600 to a wide area network such as the Internet, a mouse input device, or a scanner. The interconnection via system bus 1675 allows the central processor 1673 to communicate with each subsystem and to control the execution of instructions from system memory 1672 or the fixed disk 1679, as well as the exchange of information between subsystems. The system memory 1672 and/or the fixed disk 1679 may embody a computer readable medium. Any of the values mentioned herein can be output from one component to another component and can be output to the user.

A computer system can include a plurality of the same components or subsystems, e.g., connected together by external interface 1681 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++, Python, or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The above description of example embodiments of the invention has been presented for the purposes of illustration and description. It is not intended to be exhaustive or to limit the invention to the precise form described, and many modifications and variations are possible in light of the teaching above.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the particle" includes reference to one or more particles and equivalents thereof known to those skilled in the art, and so forth. The invention has now been described in detail for the purposes of clarity and understanding. However, it will be appreciated that certain changes and modifications may be practice within the scope of the appended claims.

All publications, patents, and patent applications cited herein are hereby incorporated by reference in their entirety for all purposes. None is admitted to be prior art.

What is claimed is:

1. A method of determining a cancer classification in a biological sample from a subject, wherein the biological sample includes a mixture of cell-free DNA molecules including tumor DNA molecules and non-tumor DNA molecules, wherein the biological sample comprises plasma or serum, the method comprising:

performing a physical size separation of the biological sample for a range of sizes of the cell-free DNA molecules to form an enriched biological sample;

performing methylation-aware sequencing to identify methylated cell-free DNA molecules in the enriched biological sample;

for each size range of a plurality of size ranges:
measuring a first amount of the methylated cell-free DNA molecules from the enriched biological sample corresponding to the size range, and
determining, by a computer system, a methylation level using the first amount of the methylated cell-free DNA molecules corresponding to the size range and a second amount of DNA molecules in a second size range that includes sizes not in the size range;

obtaining, by the computer system, a reference size pattern including a reference methylation level for each size range of the plurality of size ranges, wherein the reference size pattern is determined from a plurality of reference samples from subjects with cancer or from subjects without cancer;

comparing, by the computer system, a plurality of the methylation levels to the reference size pattern; and determining a level of cancer based on the comparison.

2. The method of claim 1, wherein the second amount is of methylated cell-free DNA molecules.

3. The method of claim 1, wherein the methylated cell-free DNA molecules are from a chromosomal arm.

4. The method of claim 1, wherein:
comparing the plurality of the methylation levels to the reference size pattern comprises:
comparing each methylation level of the plurality of size ranges to the reference methylation level at the corresponding size range,
determining that each methylation level is statistically similar to the reference methylation level at the corresponding size range.

5. The method of claim 1, wherein:
comparing the plurality of the methylation levels to the reference size pattern comprises:
determining a size pattern including the plurality of the methylation levels for the plurality of size ranges;
comparing a slope or an inflection point of the size pattern with a threshold value for a reference slope or a reference inflection point of the reference size pattern, wherein the threshold value indicates a statistically significant difference between the slope and the reference slope or the inflection point with the reference inflection point,
based on the comparing, determining the size pattern has a similar shape as the reference size pattern when the slope or the inflection point is not statistically different than the reference slope or the reference inflection point of the reference size pattern.

6. The method of claim 4, wherein:
the reference size pattern is determined from the plurality of reference samples from subjects with cancer,
the method further comprising:
determining that the subject has cancer.

7. The method of claim 1, wherein the first amount of the methylated cell-free DNA molecules is from a genomic region.

8. The method of claim 7, wherein the genomic region is a chromosomal arm, the chromosomal arm selected from the group consisting of 1p, 1q, 8p, 8q, 13q, and 14q.

9. The method of claim 1, wherein comparing the plurality of the methylation levels to the reference size pattern comprises comparing the plurality of the methylation levels to a plurality of threshold values that are determined from the plurality of reference samples.

10. The method of claim 1, wherein:
the plurality of size ranges comprises M size ranges,
measuring the first amount of the methylated cell-free DNA molecules comprises measuring the first amount of the methylated cell-free DNA molecules corresponding to the size range and corresponding to each genomic region for N genomic regions,
calculating the methylation level using the first amount of the methylated cell-free DNA molecules corresponding to the size range and corresponding to the genomic region and the second amount generates a measurement vector of N×M methylation levels, wherein N is an integer greater than or equal to 1, and M is an integer greater than 1,
the reference size pattern includes a reference vector of reference methylation levels for the N genomic regions and the M size ranges, and
comparing the plurality of the methylation levels to the reference size pattern comprises comparing the measurement vector to the reference vector.

11. The method of claim 1, further comprising:
measuring a size of each methylated cell-free DNA molecule of the methylated cell-free DNA molecules by:
obtaining sequence reads from both ends of the methylated cell-free DNA molecule,
aligning the sequence reads to a reference genome to obtain genomic coordinates of the ends of the methylated cell-free DNA molecule, and
subtracting the genomic coordinate of one end from the genomic coordinate of the other end.

12. The method of claim 1, further comprising:
measuring a size of each methylated cell-free DNA molecule of the methylated cell-free DNA molecules using sequence reads, wherein the sequence reads are obtained by massively parallel sequencing.

13. The method of claim 1, wherein the methylated cell-free DNA molecules comprise 1,000 molecules.

14. The method of claim 1, wherein the methylation-aware sequencing includes bisulfite sequencing, sequencing preceded by methylation-sensitive restriction enzyme digestion, immunoprecipitation using anti-methylcytosine antibody or methylation binding protein, or single molecule sequencing.

15. The method of claim 1, wherein determining the methylation level comprises:
calculating a ratio of the first amount to the second amount,
determining a difference between the ratio and an average value for a control group, and
dividing the difference by a standard deviation for the control group.

16. The method of claim 1, wherein the plurality of size ranges comprises at least 71 size ranges.

17. The method of claim 1, wherein the comparing, by the computer system, the plurality of the methylation levels to the reference size pattern comprises using a machine learning model trained using datasets including samples from subjects with cancer and subjects without cancer.

18. The method of claim 10, wherein N is at least 4 and M is at least 71.

19. The method of claim 1, wherein the range of sizes comprises sizes including 100 bp to 140 bp.

20. The method of claim 1, wherein the range of sizes comprises sizes including 50 bp to 400 bp.

21. The method of claim 1, wherein the range of sizes comprises sizes including 385 bp to 425 bp.

22. The method of claim 1, further comprising training the machine learning model, wherein training the machine learning model comprises:
- collecting the datasets including the samples from the subjects with cancer and the subjects without cancer, and
- training the machine learning model using the datasets.

23. The method of claim 1, wherein the physical size separation includes gel electrophoresis, filtration, selective-size precipitation, or hybridization.

* * * * *